(12) United States Patent
Zaborsky

(10) Patent No.: US 12,214,097 B2
(45) Date of Patent: Feb. 4, 2025

(54) DISINFECTING METHODS AND APPARATUS

(71) Applicant: Inikoa Medical, Inc., Newark, CA (US)

(72) Inventor: Brett Zaborsky, Newark, CA (US)

(73) Assignee: INIKOA MEDICAL, INC., Newark, CA (US)

( * ) Notice: Subject to any disclaimer, the term of this patent is extended or adjusted under 35 U.S.C. 154(b) by 52 days.

(21) Appl. No.: 18/208,054

(22) Filed: Jun. 9, 2023

(65) Prior Publication Data
US 2023/0330286 A1    Oct. 19, 2023

Related U.S. Application Data

(60) Division of application No. 16/678,429, filed on Nov. 8, 2019, now abandoned, which is a division of
(Continued)

(51) Int. Cl.
*A61L 2/10* (2006.01)
*A61B 90/70* (2016.01)
(Continued)

(52) U.S. Cl.
CPC ............... *A61L 2/10* (2013.01); *A61B 90/70* (2016.02); *A61L 2/0047* (2013.01);
(Continued)

(58) Field of Classification Search
CPC ........ A61L 2/10; A61L 2/0047; A61L 2/0052; A61L 2/24; A61L 2/26; A61L 2/18;
(Continued)

(56) References Cited

U.S. PATENT DOCUMENTS 2,259,910 A   10/1941   Rylsky
4,172,631 A   10/1979   Yevick
(Continued)

FOREIGN PATENT DOCUMENTS

WO    2014159874 A1    10/2014

OTHER PUBLICATIONS

International Search Report and Written Opinion in corresponding PCT Application No. PCT/US2018/067211, mailed on Mar. 8, 2019, 9 pages.

*Primary Examiner* — Sean M Luck
(74) *Attorney, Agent, or Firm* — Edell, Shapiro & Finnan, LLC

(57) ABSTRACT

Light disinfecting systems are provided in which light emanating from an end or side of optical fibers is used to disinfect a target site. According to one implementation a light beam emanating from an end emitting optical fiber is directed into a body that includes a plurality of optical surfaces that are configured to direct at least a portion of the end emitted beam of bacterial disinfecting light to the target site. The assembly may further include a substrate coupled to the body, the substrate including one or more channels in which reside one or more radially emitting optical fibers that are configured to radially emit bacterial disinfecting light towards the target site, the substrate being at least partially transparent to the bacterial disinfecting light.

20 Claims, 54 Drawing Sheets

Related U.S. Application Data application No. 15/853,099, filed on Dec. 22, 2017, now abandoned, which is a continuation of application No. 15/852,742, filed on Dec. 22, 2017, now abandoned.

(51) Int. Cl.

| | |
|---|---|
| *A61L 2/00* | (2006.01) |
| *A61L 2/24* | (2006.01) |
| *A61L 2/26* | (2006.01) |
| *A61N 5/06* | (2006.01) |
| *F21V 8/00* | (2006.01) |
| *G02B 6/36* | (2006.01) |
| *A61L 2/18* | (2006.01) |
| *G02B 6/02* | (2006.01) |
| *G02B 6/24* | (2006.01) |

(52) U.S. Cl.
CPC ............... *A61L 2/0052* (2013.01); *A61L 2/24* (2013.01); *A61L 2/26* (2013.01); *A61N 5/0624* (2013.01); *G02B 6/0006* (2013.01); *G02B 6/3624* (2013.01); *A61L 2/18* (2013.01); *A61L 2202/14* (2013.01); *A61L 2202/24* (2013.01); *A61N 5/0616* (2013.01); *A61N 2005/063* (2013.01); *A61N 2005/0661* (2013.01); *A61N 2005/0662* (2013.01); *A61N 2005/0663* (2013.01); *G02B 6/001* (2013.01); *G02B 6/0229* (2013.01); *G02B 6/241* (2013.01)

(58) Field of Classification Search
CPC ............. A61L 2202/14; A61L 2202/24; A61N 5/0624; A61N 5/0616; A61N 2005/063; A61N 2005/0661; A61N 2005/0662; A61N 2005/0663; A61B 90/70; G02B 6/0006; G02B 6/3624; G02B 6/001; G02B 6/0229; G02B 6/241
See application file for complete search history.

(56) References Cited

U.S. PATENT DOCUMENTS

| | | | |
|---|---|---|---|
| 4,412,834 A | 11/1983 | Kulin et al. | |
| 4,842,356 A | 6/1989 | Mori | |
| 4,959,759 A | 9/1990 | Kohler | |
| 5,260,020 A | 11/1993 | Wilk et al. | |
| 5,353,786 A | 10/1994 | Wilk | |
| 5,381,506 A | 1/1995 | Amick et al. | |
| 5,496,305 A | 3/1996 | Kittrell et al. | |
| 5,594,825 A | 1/1997 | Kawasaki et al. | |
| 5,637,877 A | 6/1997 | Sinofsky | |
| 5,695,482 A | 12/1997 | Kaldany | |
| 5,890,796 A | 4/1999 | Marinelli et al. | |
| 5,905,837 A | 5/1999 | Wang et al. | |
| 6,102,559 A | 8/2000 | Nold et al. | |
| 6,272,269 B1 | 8/2001 | Naum | |
| 6,461,569 B1 | 10/2002 | Boudreaux | |
| 6,524,529 B1 | 2/2003 | Horton, III | |
| 6,551,346 B2 | 4/2003 | Crossley | |
| 6,564,087 B1 | 5/2003 | Pitris et al. | |
| 6,565,248 B2 | 5/2003 | Honguh et al. | |
| 6,697,666 B1 | 2/2004 | Richards-Kortum et al. | |
| 6,742,916 B1 | 6/2004 | Dunn | |
| 6,948,840 B2 | 9/2005 | Grenda | |
| 7,178,941 B2 | 2/2007 | Roberge et al. | |
| 7,226,470 B2 | 6/2007 | Kemeny et al. | |
| 7,252,677 B2 | 8/2007 | Burwell et al. | |
| 7,274,844 B2 | 9/2007 | Walt et al. | |
| 7,305,163 B2 | 12/2007 | Williams | |
| 7,686,839 B2 | 3/2010 | Parker | |
| 7,712,907 B2 | 5/2010 | Zyka | |
| 7,717,598 B2 | 5/2010 | Kakizaki et al. | |
| 7,721,672 B2 | 5/2010 | Nakano et al. | |
| 7,826,698 B1 | 11/2010 | Meir et al. | |
| 8,047,987 B2 | 11/2011 | Grey et al. | |
| 8,197,087 B2 | 6/2012 | Sobue et al. | |
| 8,417,323 B2 | 4/2013 | Uzunbajakava et al. | |
| 8,431,910 B1 | 4/2013 | Perry | |
| 8,556,950 B2 | 10/2013 | Rioux et al. | |
| 8,574,490 B2 | 11/2013 | Haytman et al. | |
| 8,632,576 B2 | 1/2014 | Quisenberry | |
| 8,702,640 B2 | 4/2014 | Dacey, Jr. et al. | |
| 8,706,211 B2 | 4/2014 | Dacey, Jr. et al. | |
| 8,740,780 B2 | 6/2014 | Honda et al. | |
| 8,953,914 B2 | 2/2015 | Genier | |
| 8,980,174 B2 | 3/2015 | Haytman et al. | |
| 9,033,961 B2 | 5/2015 | Melsky et al. | |
| 9,259,513 B2 | 2/2016 | Bedwell et al. | |
| 9,278,148 B2 | 3/2016 | Fewkes et al. | |
| 9,295,742 B2 | 3/2016 | Rasooly et al. | |
| 9,615,884 B2 | 4/2017 | Armour et al. | |
| 2002/0025097 A1 | 2/2002 | Cooper et al. | |
| 2002/0037133 A1 | 3/2002 | Unsworth | |
| 2003/0017073 A1 | 1/2003 | Eckhardt et al. | |
| 2003/0232303 A1 | 12/2003 | Black | |
| 2004/0091195 A1 | 5/2004 | Bischel et al. | |
| 2005/0175658 A1 | 8/2005 | Dimauro et al. | |
| 2005/0270796 A1 | 12/2005 | Ichikawa et al. | |
| 2005/0279354 A1 | 12/2005 | Deutsch et al. | |
| 2006/0140562 A1 | 6/2006 | Joseph et al. | |
| 2006/0167532 A1 | 6/2006 | Parker et al. | |
| 2006/0206997 A1 | 9/2006 | Chiang et al. | |
| 2006/0256575 A1 | 11/2006 | Vayser | |
| 2007/0133224 A1 | 6/2007 | Parker | |
| 2007/0133932 A1* | 6/2007 | Kingsford | G02B 6/001 385/114 |
| 2007/0147059 A1 | 6/2007 | Gebauer et al. | |
| 2007/0208395 A1 | 9/2007 | Leclerc et al. | |
| 2007/0211487 A1 | 9/2007 | Sormani | |
| 2007/0225695 A1 | 9/2007 | Mayer et al. | |
| 2007/0233208 A1 | 10/2007 | Kurtz et al. | |
| 2007/0239232 A1 | 10/2007 | Kurtz et al. | |
| 2007/0263975 A1 | 11/2007 | Boutoussov et al. | |
| 2008/0058629 A1 | 3/2008 | Seibel et al. | |
| 2009/0112295 A1 | 4/2009 | Hyde et al. | |
| 2010/0220492 A1 | 9/2010 | Richardson et al. | |
| 2010/0265551 A1 | 10/2010 | Endoh | |
| 2010/0324505 A1 | 12/2010 | Levenson et al. | |
| 2011/0160713 A1 | 6/2011 | Neuberger | |
| 2011/0255828 A1 | 10/2011 | Sudarshanam | |
| 2011/0291995 A1 | 12/2011 | Shr et al. | |
| 2012/0165716 A1 | 6/2012 | Reuben | |
| 2012/0265120 A1 | 10/2012 | Beisang et al. | |
| 2012/0287668 A1 | 11/2012 | Richardson et al. | |
| 2012/0321509 A1 | 12/2012 | Bak | |
| 2013/0035629 A1 | 2/2013 | Soltz et al. | |
| 2013/0070312 A1 | 3/2013 | Saiga | |
| 2013/0088888 A1 | 4/2013 | Fewkes et al. | |
| 2013/0115131 A1 | 5/2013 | Hegg et al. | |
| 2013/0267888 A1 | 10/2013 | Rhodes et al. | |
| 2014/0277294 A1 | 9/2014 | Jones et al. | |
| 2015/0037201 A1 | 2/2015 | Armour et al. | |
| 2015/0043875 A1 | 2/2015 | Bookbinder et al. | |
| 2015/0057504 A1 | 2/2015 | Vayser et al. | |
| 2015/0117814 A1 | 4/2015 | Hung | |
| 2015/0126976 A1 | 5/2015 | Tang et al. | |
| 2015/0148734 A1 | 5/2015 | Fewkew et al. | |
| 2015/0231287 A1 | 8/2015 | Lin et al. | |
| 2015/0335773 A1 | 11/2015 | Bauco | |
| 2015/0335911 A1 | 11/2015 | Rogers et al. | |
| 2016/0001038 A1 | 1/2016 | Romo et al. | |
| 2016/0082281 A1 | 3/2016 | Gerber et al. | |
| 2016/0106873 A1 | 4/2016 | Dorbinsky et al. | |
| 2016/0114186 A1 | 4/2016 | Dobrinsky | |
| 2016/0128816 A1 | 5/2016 | Khangura | |
| 2019/0192706 A1 | 6/2019 | Zaborsky | |

\* cited by examiner

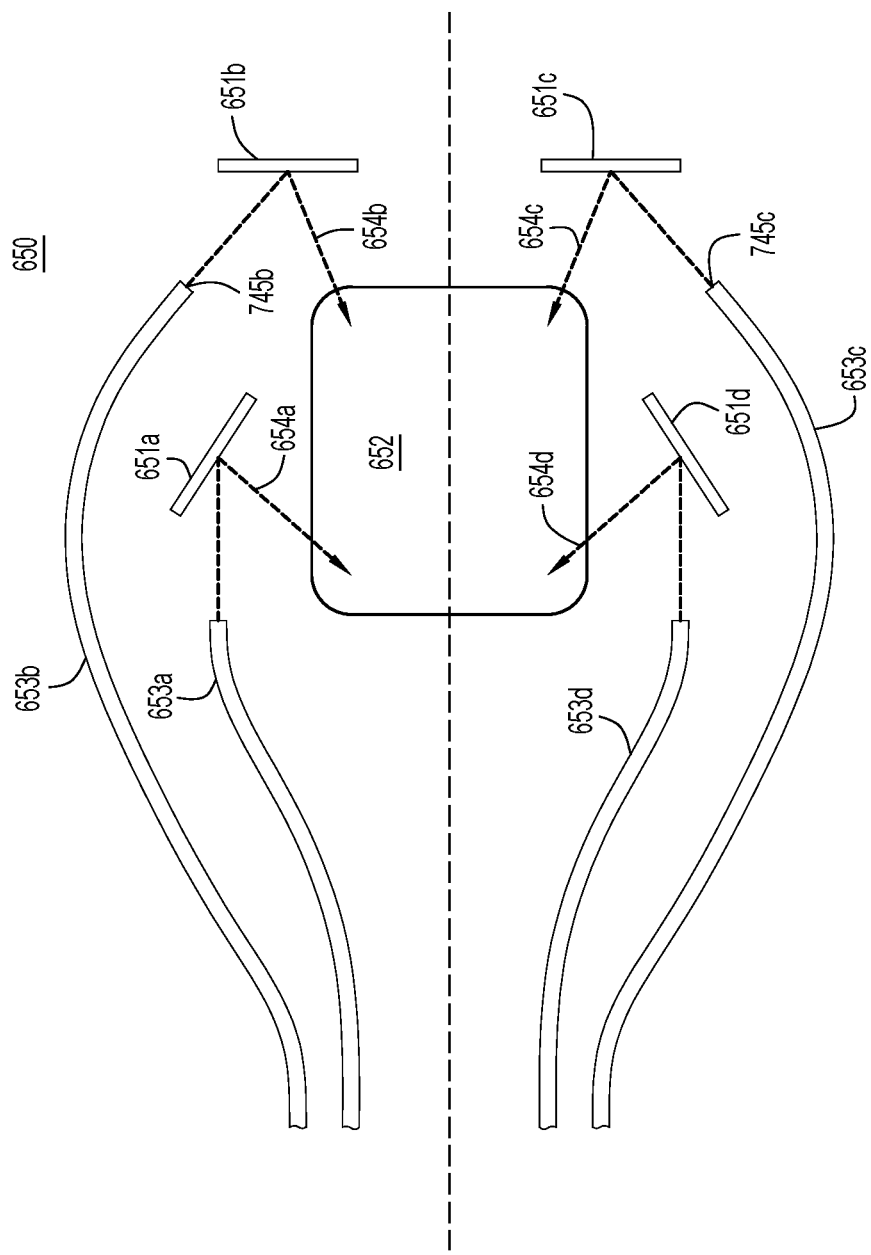

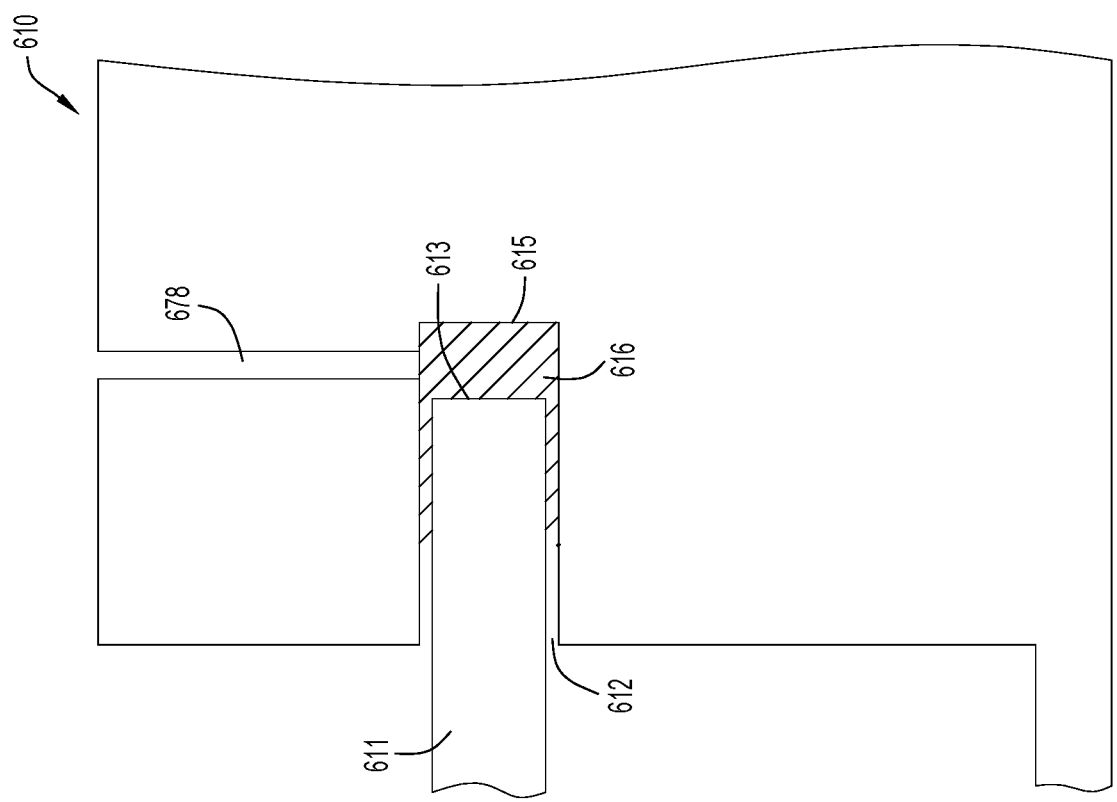

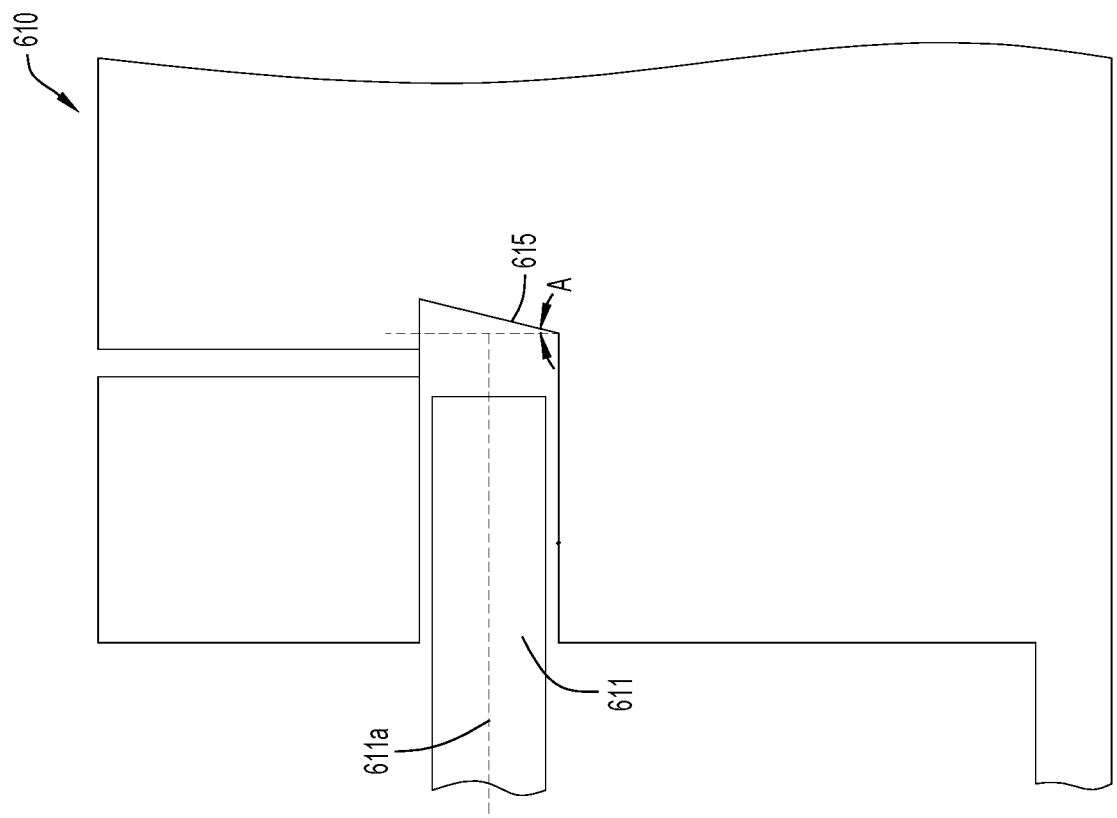

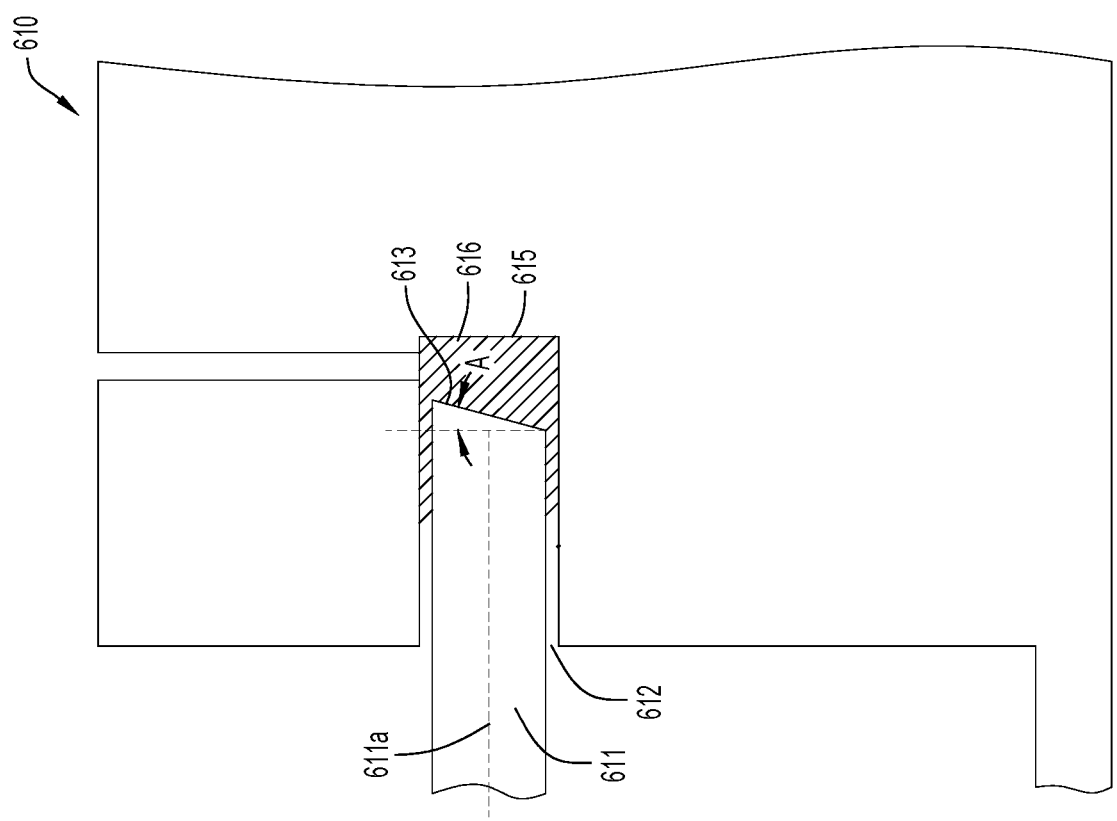

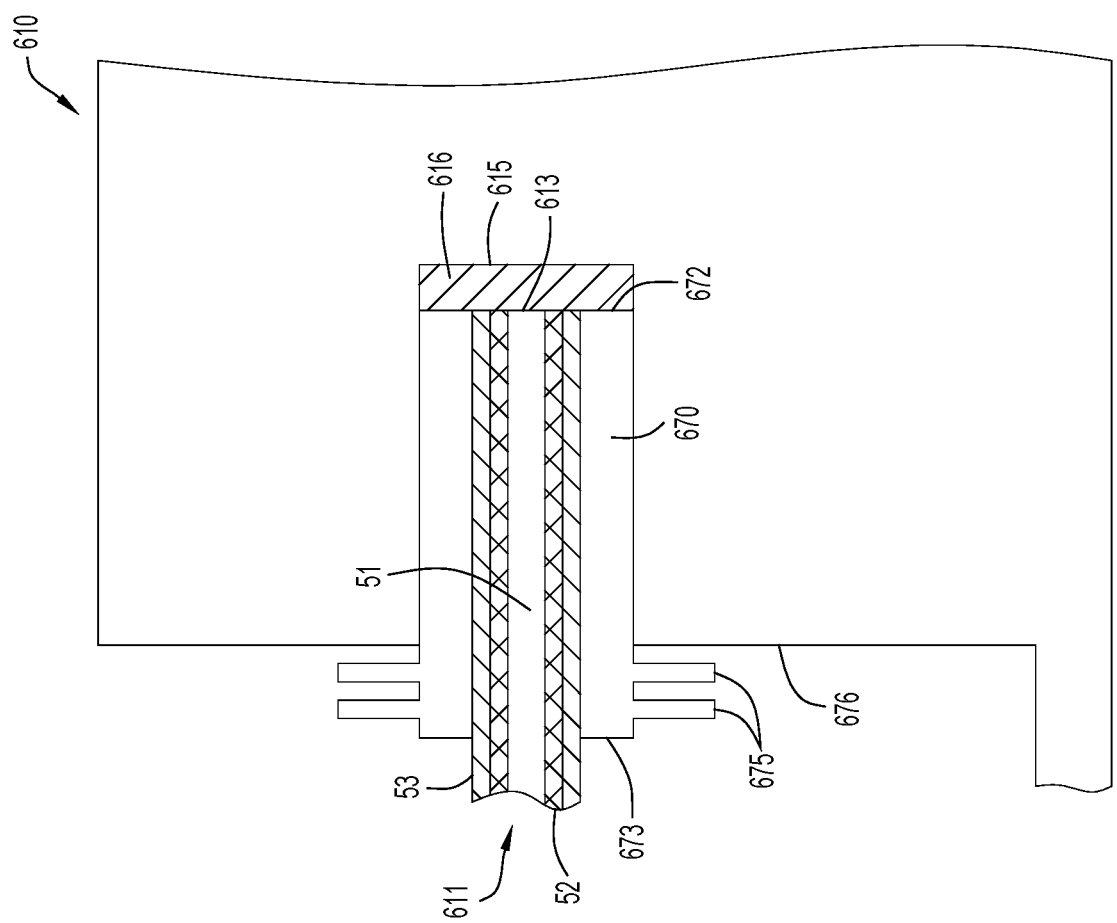

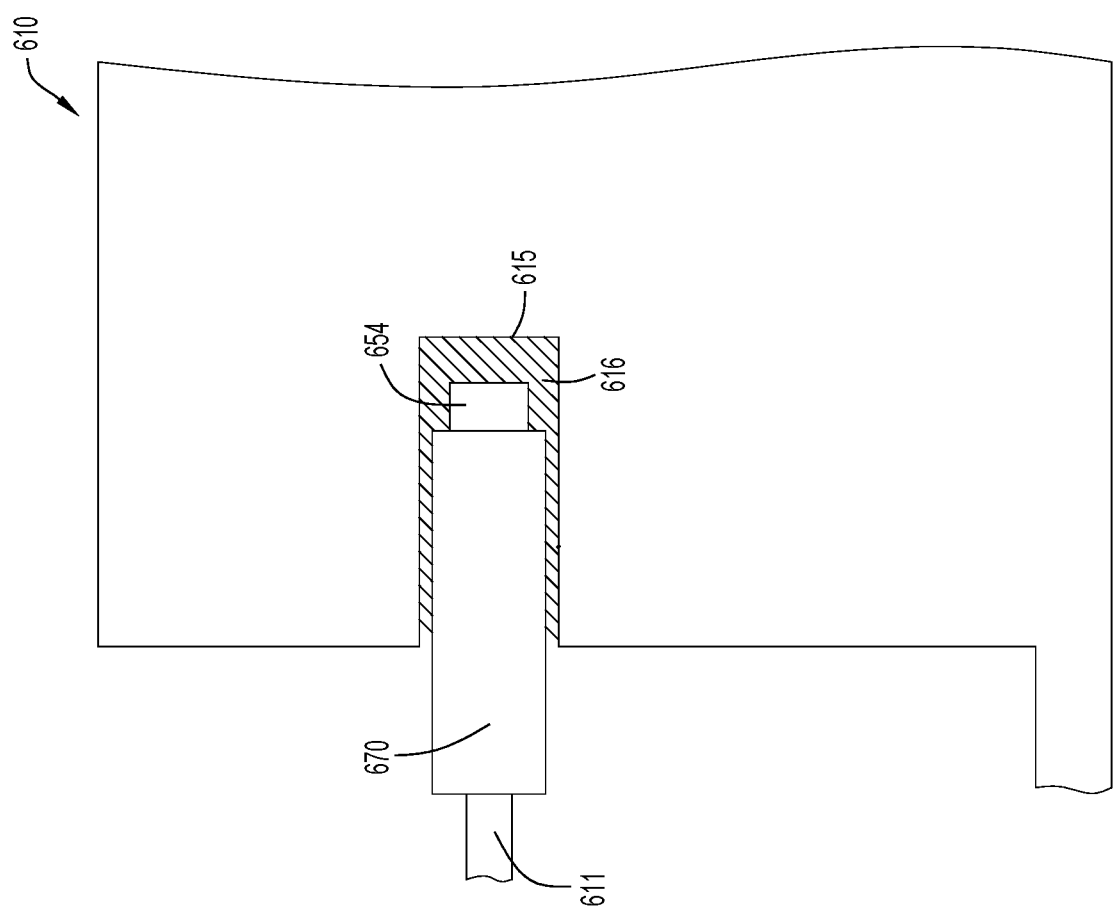

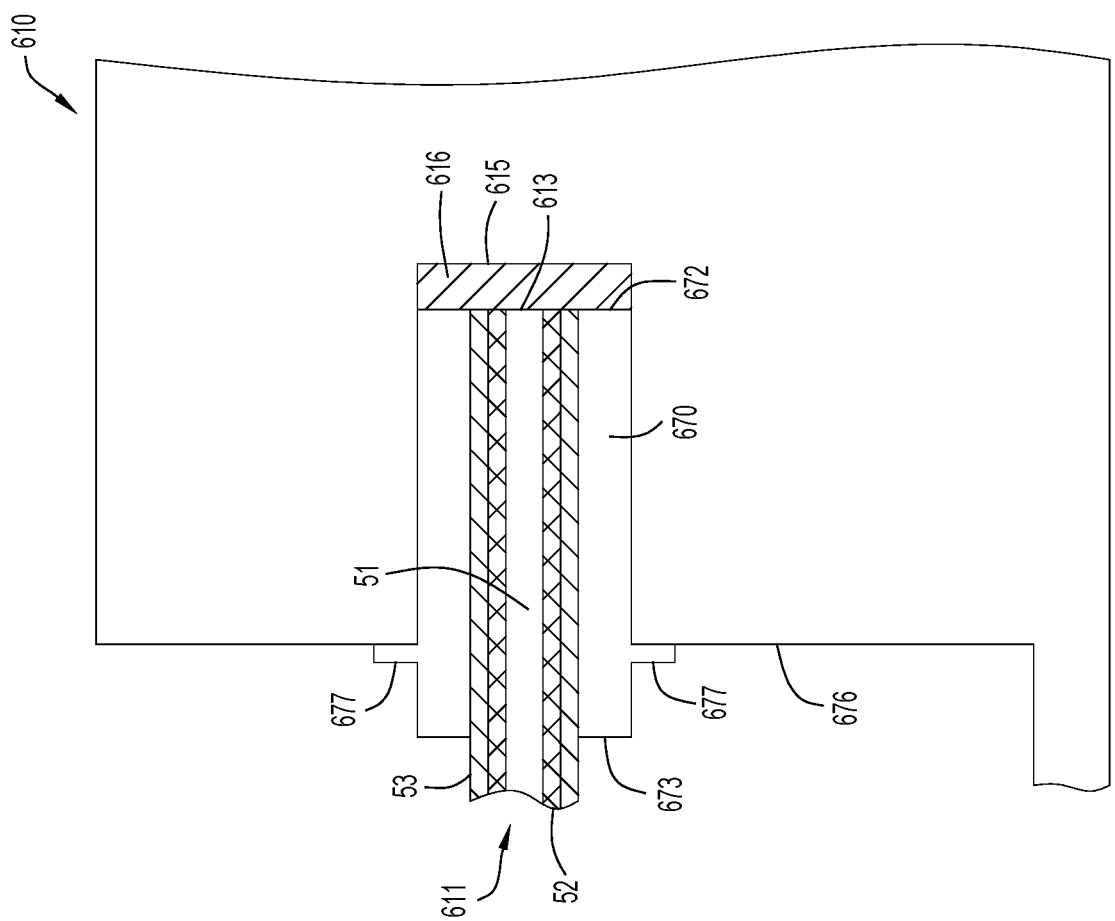

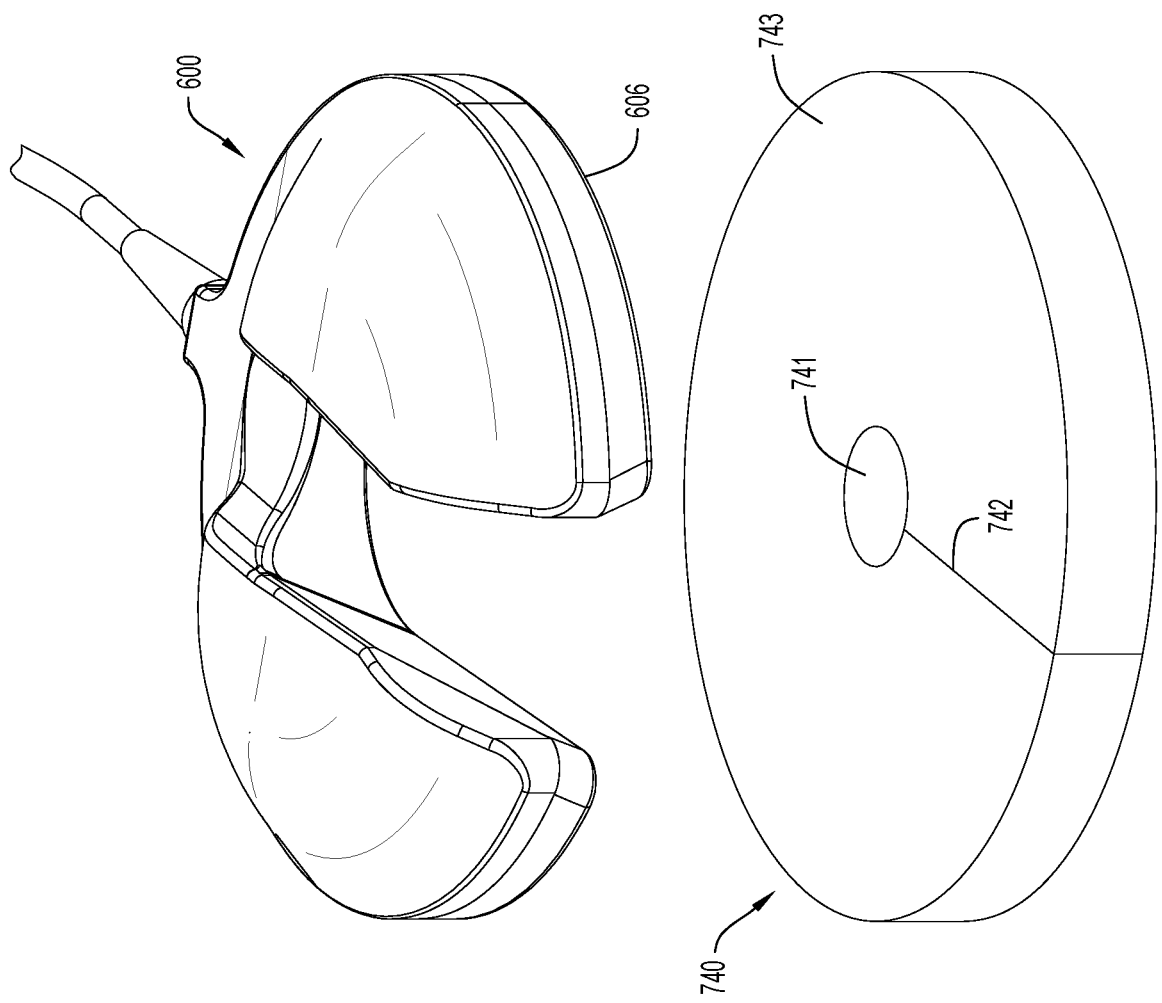

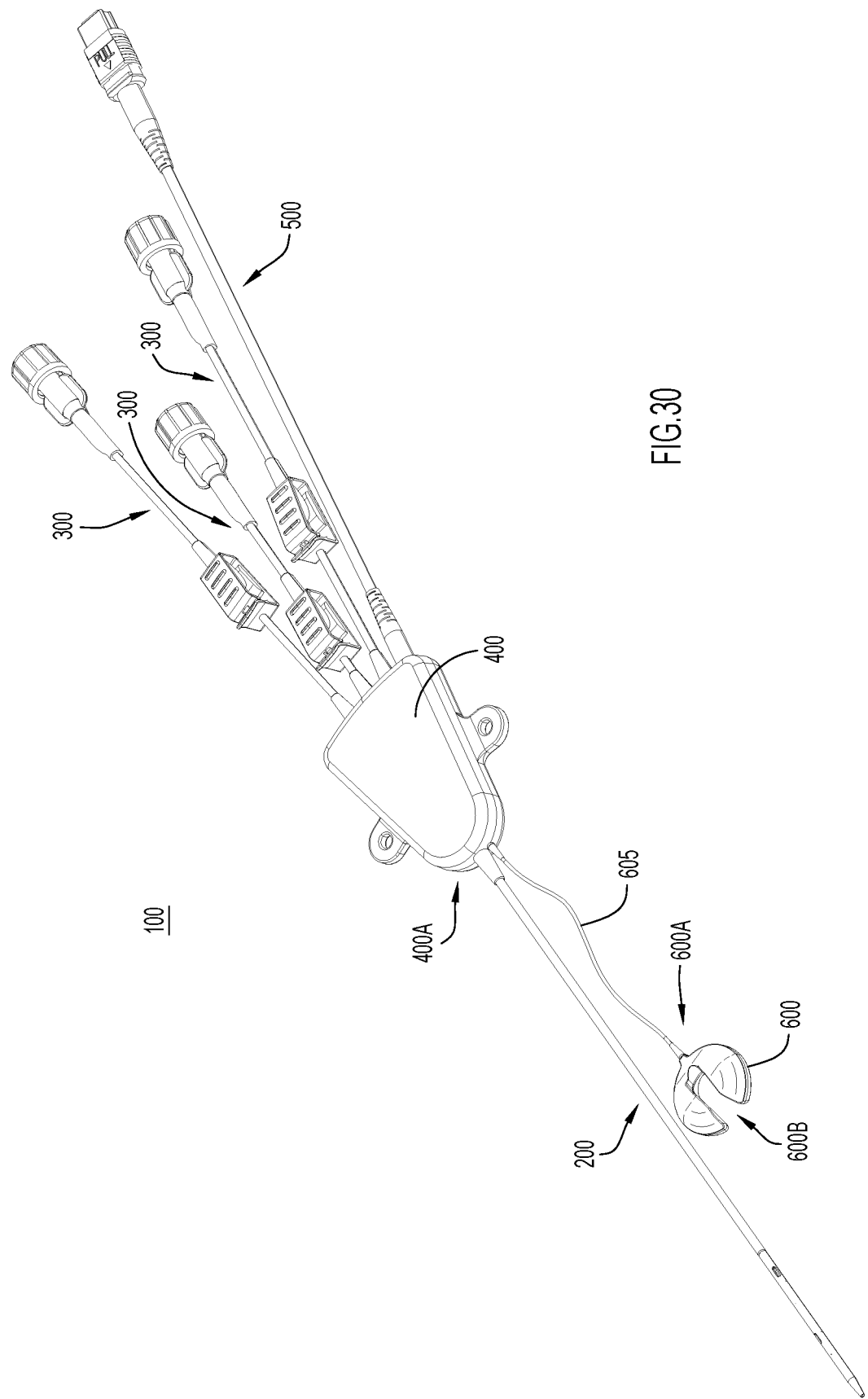

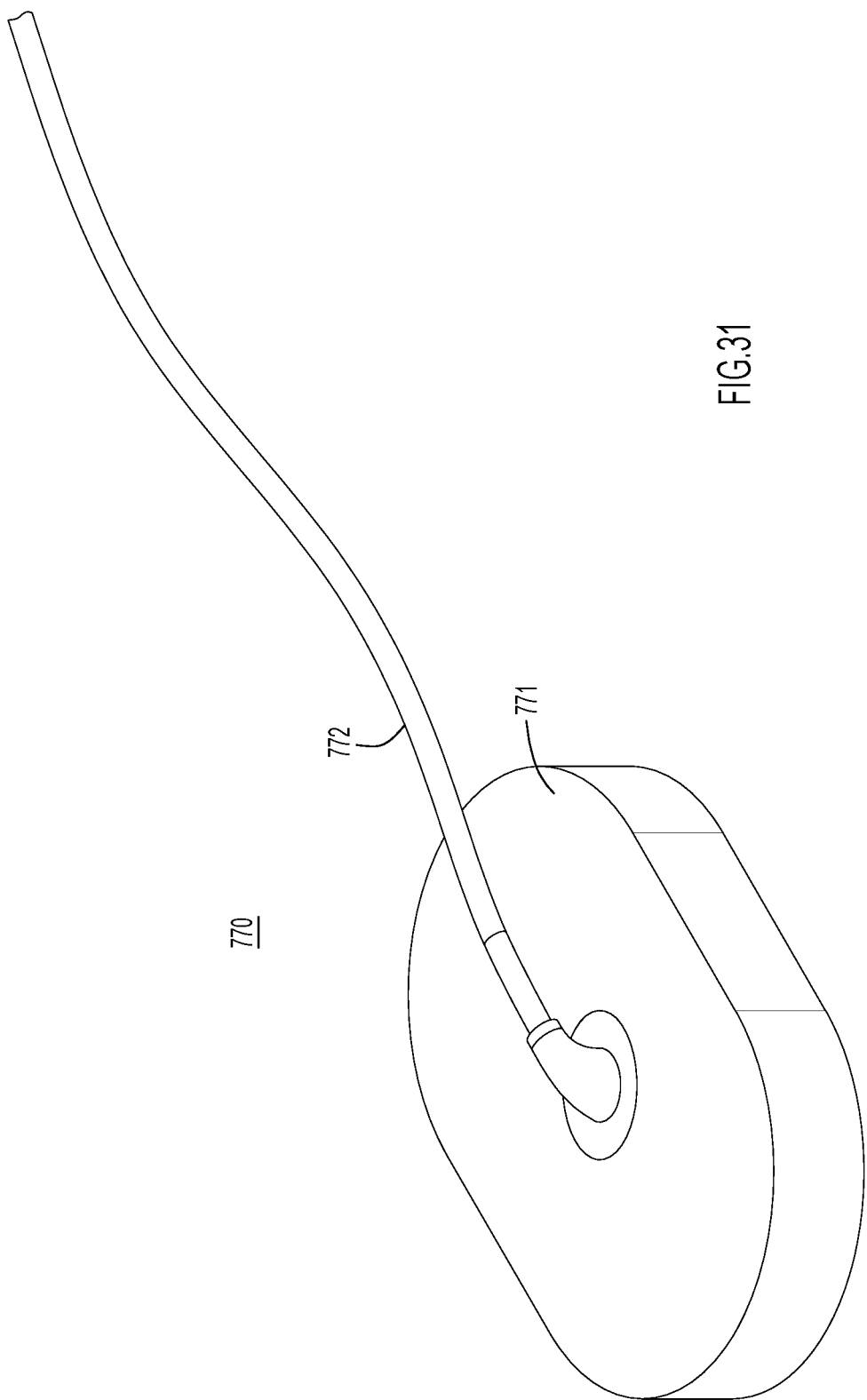

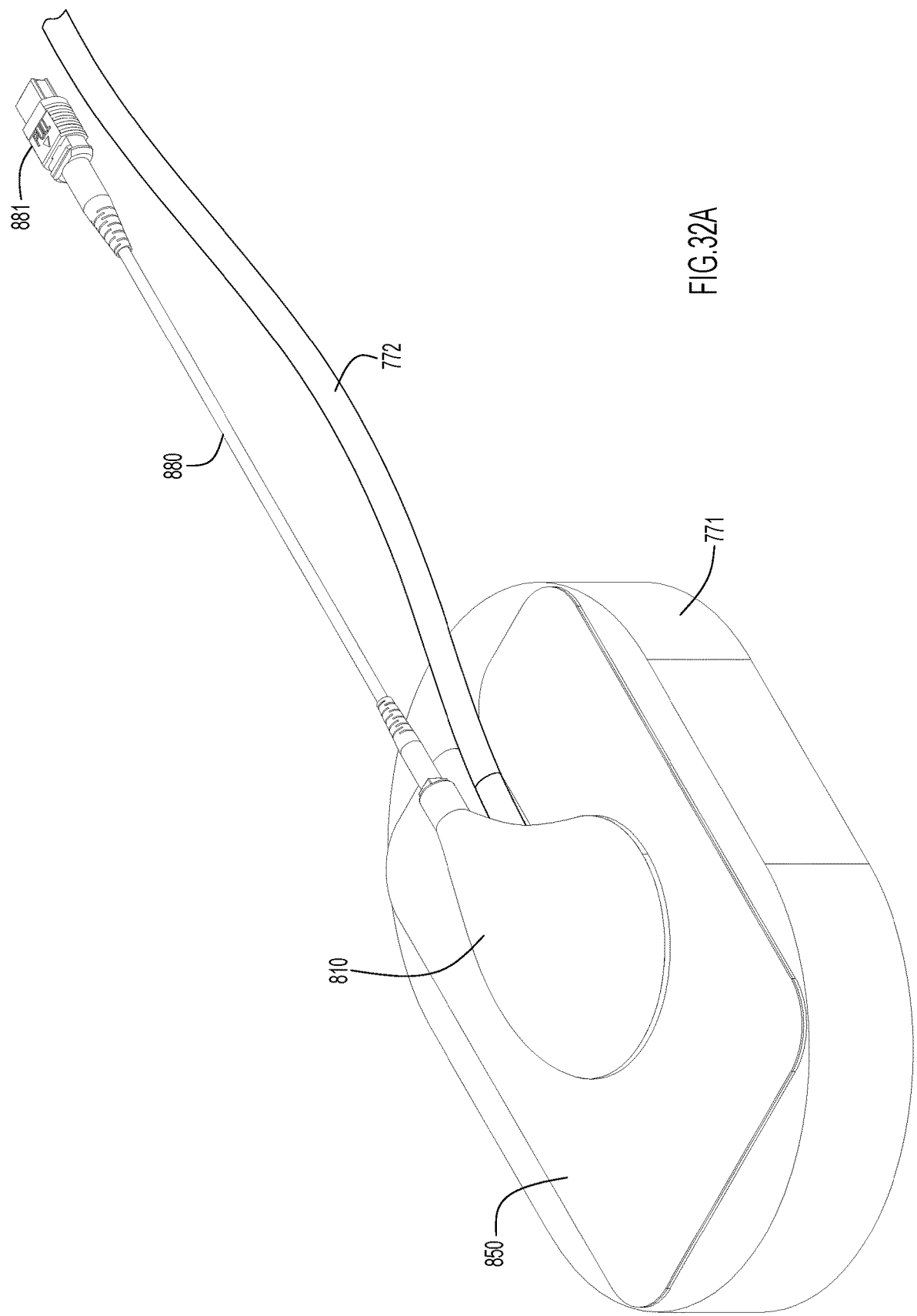

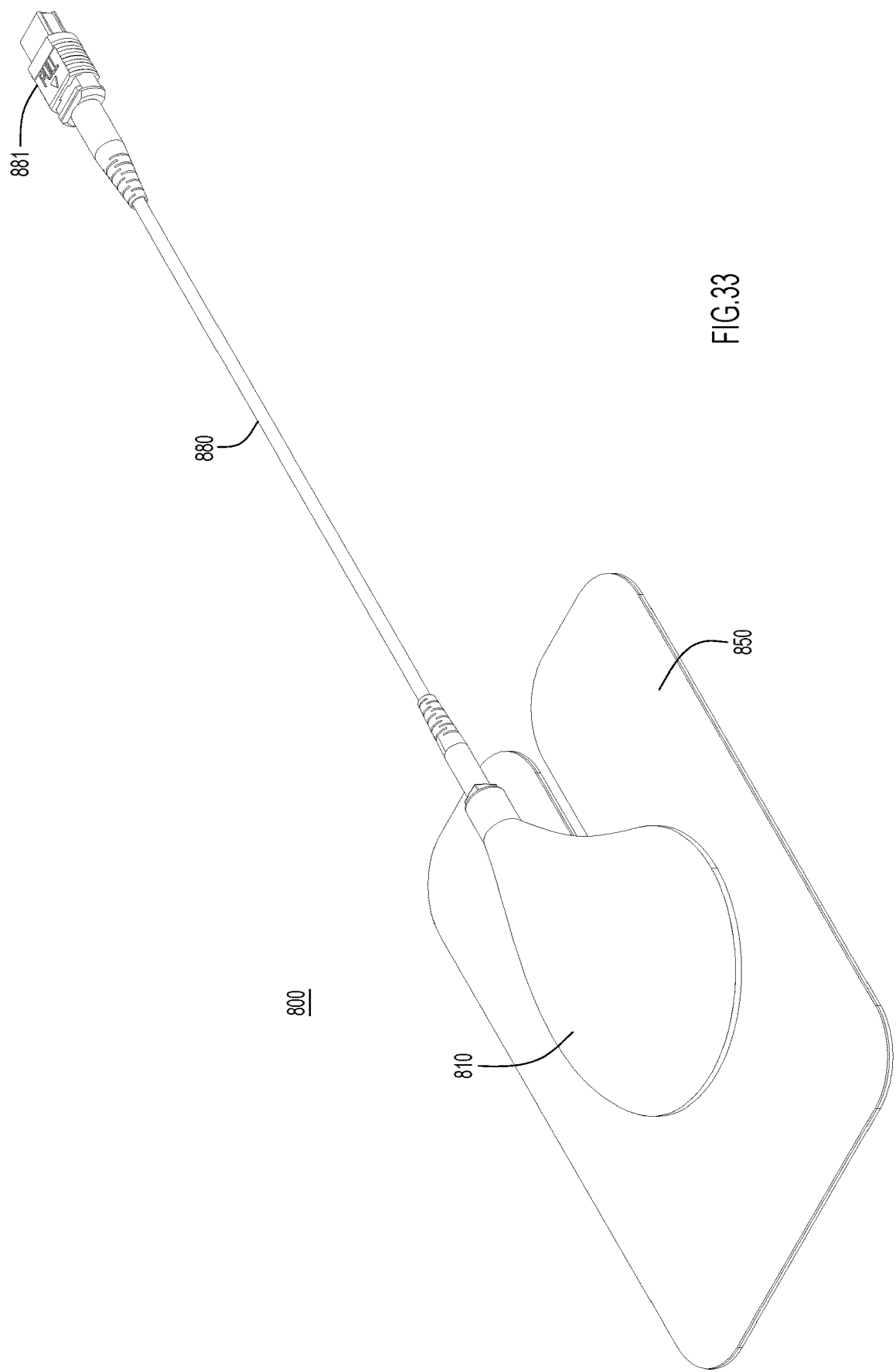

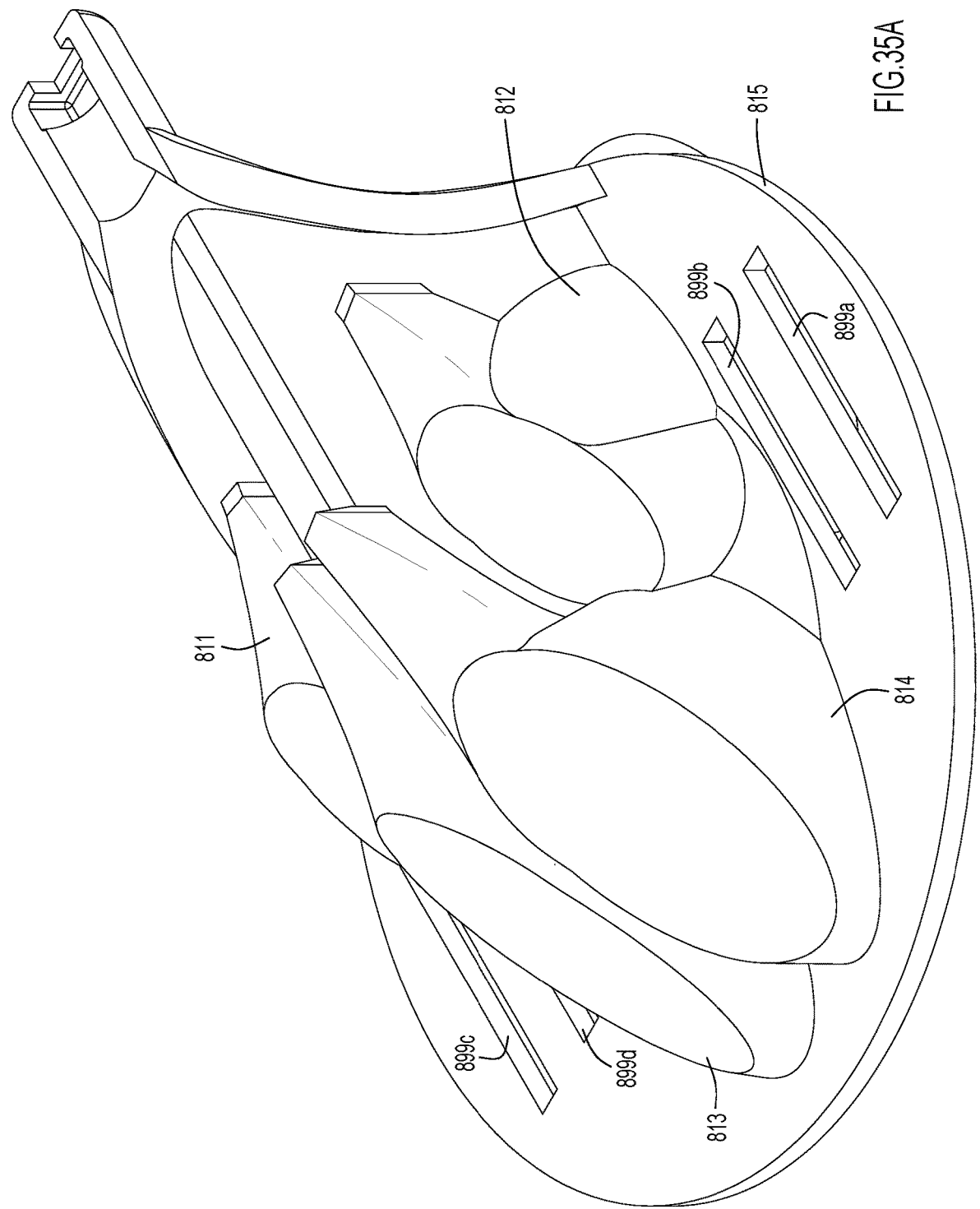

DISINFECTING METHODS AND APPARATUS

CROSS-REFERENCE TO RELATED APPLICATION

This application is a divisional of U.S. patent application Ser. No. 16/678,429, filed Nov. 8, 2019, which is a divisional of U.S. patent application Ser. No. 15/853,099 filed Dec. 22, 2017, which is now abandoned, which is a continuation of U.S. patent application Ser. No. 15/852,742 filed Dec. 22, 2017, which is now abandoned, each of which is incorporated herein by reference in its entirety

TECHNICAL FIELD

The present disclosure relates to apparatus and methods for disinfecting any of a host of surfaces including those associated medical device insertion sites and superficial wounds of a patient.

BACKGROUND

Unwanted and dangerous bacteria growth can occur on devices that are commonly used to treat patients and also around sites in which the devices are inserted into a patient. These devices may include central venous catheters, urinary catheters, ventilators, wound protection devices, laparoscopic surgical devices, etc. Bacterial growth in the wound (s) of a patient is also problematic. Hospital acquired infections account for a substantial yearly expense to hospitals and insurance companies, and are a major cause of extending hospital stays for patients. Equipment or components outside the medical field, such as water processing plants, food processing plants, dairies, livestock habitation facilities, etc. are also susceptible bacteria growth.

SUMMARY OF THE DISCLOSURE

According to some implementations disclosed herein light is used to disinfect the surfaces of devices used in the medical treatment of patients. According to other implementations light is used to disinfect medical device insertion sites on a patients or the wound site of a patient. The light may be any wavelength of light that is capable of killing bacteria, such as, for example, ultra violet (UV) light and blue light which may be delivered by one or both of a radially emitting optical fiber and an end emitting optical fiber.

An advantage of using light to kill bacteria is that it is not susceptible to the danger of antimicrobial resistance that can occur with the use of pharmacologic or chemical agents. Another advantage is that there are severe side effects associated with many pharmacologic or chemical agents are avoided.

It is important to note that although the forthcoming disclosure is directed primarily to the medical field, the devices and methods disclosed herein can also be applied to other fields. These may include, for example, equipment or components of water processing plants, food processing plants, dairies, livestock habitation facilities, etc.

These and other advantages and features will become evident in view of the drawings and detailed description.

BRIEF DESCRIPTION OF THE DRAWINGS

FIG. 14 is a schematic drawing of a disinfecting device that is configured to direct four light beams to a disinfecting target area.

FIG. 17 shows an optical fiber assembled inside a lumen or recess of an optical body according to one implementation.

FIG. 18A illustrates an optical body according to one implementation wherein the refractive optical surface at the end wall of an opening or recess in the optical body is tilted an angle with respect to the longitudinal axis of the opening or recess.

FIG. 18B illustrates an implementation wherein the distal end of the optical fiber is angled to inhibit back reflectance of light into the core of the optical fiber.

FIG. 19A illustrates an optical fiber assembled in an optical body according to one implementation.

FIGS. 21A and 21B illustrate an optical fiber assembly according to one implementation that includes a rigid structure and an end cap.

FIG. 23 shows a rigid structure according to one implementation that includes one or more radially extending features to limit the longitudinal advancement of the rigid structure into the opening or recess of an optical body.

FIG. 29A illustrates a kit that includes a light disinfecting device and an absorbent pad that in use is configured to be disposed between the light disinfecting device and the insertion site of a patient.

FIG. 30 shows the light disinfecting device of FIG. 5 integrated with a central venous catheter system.

FIG. 31 illustrates a conventional wound vacuum apparatus.

FIGS. 32A and 32B show different a perspective views of a light disinfecting assembly integrated with a conventional wound vacuum apparatus and configured to deliver disinfecting light to a wound site of a patient.

FIG. 33 shows the light disinfecting assembly of FIG. 31.

FIGS. 35A, 35B, and 35C are perspective views of a light disinfecting device according to one implementation.

DETAILED DESCRIPTION

Figure 1A:
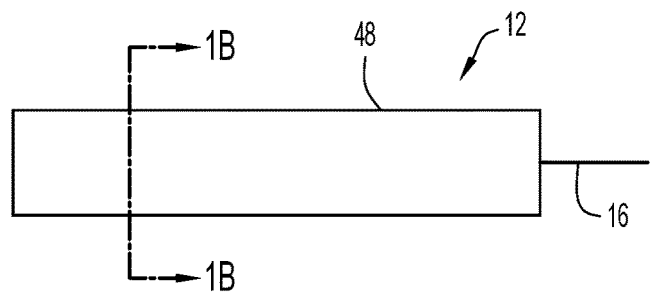
FIGS. 1A and 1B respectively show a side view and cross-section view of a radially emitting optical fiber according to some implementation.
Figure 1B:
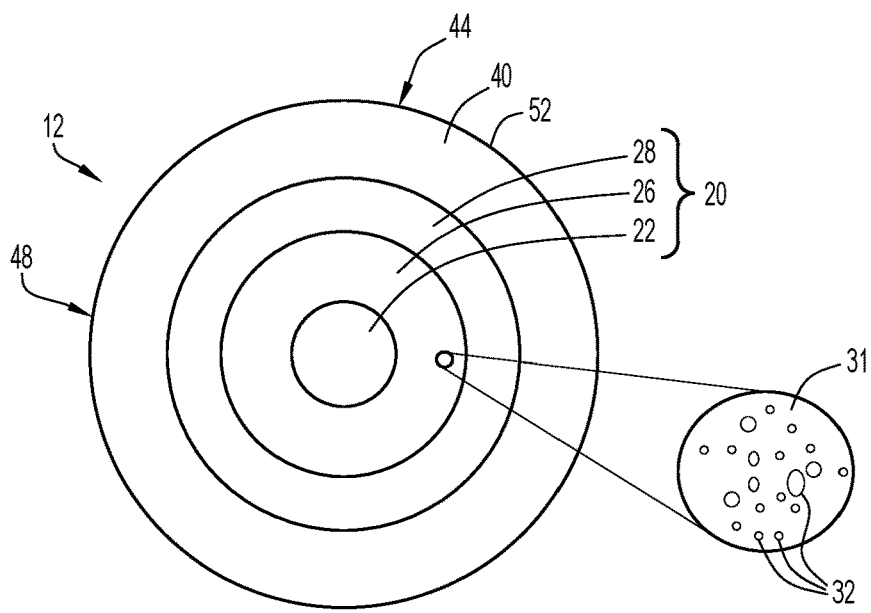

FIG. 1A is a schematic side view of a radially emitting fiber with a plurality of voids in the core of the radially emitting optical fiber 12 having a central axis 16. FIG. 1B is a schematic cross-section of a radially emitting optical fiber 12 as viewed along the direction 1B-1B in FIG. 1A. Radially emitting fiber 12 can be, for example, an optical fiber with a nano-structured fiber region having periodic or non-periodic nano-sized structures 32 (for example voids). In an example implementation, fiber 12 includes a core 20 divided into three sections or regions. These core regions are: a solid central portion 22, a nano-structured ring portion (inner annular core region) 26, and outer, solid portion 28 surrounding the inner annular core region 26. A cladding region 40 surrounds the annular core 20 and has an outer surface. The cladding 40 may have low refractive index to provide a high numerical aperture. The cladding 40 can be, for example, a low index polymer such as UV or thermally curable fluoroacrylate or silicone.

An optional coating 44 surrounds the cladding 40. Coating 44 may include a low modulus primary coating layer and a high modulus secondary coating layer. In at least some implementations, coating layer 44 comprises a polymer coating such as an acrylate-based or silicone based polymer. In at least some implementations, the coating has a constant diameter along the length of the fiber.

In other exemplary implementations, coating 44 is designed to enhance the distribution and/or the nature of radiated light that passes from core 20 through cladding 40. The outer surface of the cladding 40 or the of the outer of optional coating 44 represents the sides 48 of fiber 12 through which light traveling in the fiber is made to exit via scattering, as described herein.

A protective jacket (not shown) optionally covers the cladding 40.

In some implementations, the core region 26 of radially emitting fiber 12 comprises a glass matrix 31 with a plurality of non-periodically disposed nano-sized structures (e.g., voids) 32 situated therein, such as the example voids shown in detail in the magnified inset of FIG. 1B. In another example implementation, voids 32 may be periodically disposed, such as in a photonic crystal optical fiber, wherein the voids may have diameters between about 1×10-6 m and 1×10-5 m. Voids 32 may also be non-periodically or randomly disposed. In some exemplary implementations, glass 31 in region 26 is fluorine-doped silica, while in other implementations the glass may be an undoped pure silica.

The nano-sized structures 32 scatter the light away from the core 20 and toward the outer surface of the fiber. The scattered light is then diffused through the outer surface of the fiber 12 to provide the desired illumination. That is, most of the light is diffused (via scattering) through the sides of the fiber 12 and along the fiber length without the need to remove any portion of the cladding 40.

According to some implementations the nano-sized structures 32 are formed in the cladding 40 of the fiber in lieu of or in conjunction with providing nano-sized structures in the core 12.

According to some implementations the core 20 has a diameter in the range of 125-300 µm and the overall diameter of the fiber system, including the protective jacket, is in the range of 700 to 1200 µm. According to some implementation, the outer diameter of the fiber 12 without a jacket is in the range of 200-350 µm.

A detailed description of exemplary radially emitting optical fibers may be found in Reissue Patent No. RE46,098 whose content is incorporated herein by reference in its entirety.

An example of a radially emitting optical fiber is the Fibrance® Light Diffusing Fiber manufactured by Corning® Incorporated located in Corning, New York. The Fibrance® Light Diffusing Fiber has many of the attributes of the radially emitting fiber 12 described above. An advantage of the Fibrance® Light Diffusing Fiber is that it emits light essentially along its entire length and has a small functional bend radius of around 5 millimeters which allows it be easily bent to assume a host of shapes. Breakage of the fiber typically occurs when it is bent to a bend radius of less than about 2 millimeters.

Radially emitting fibers like those disclosed in Reissue Patent No. RE46,908 do not require the removal of a light reflective component or light reflective element to enable the emission of light radially from the optical fiber.

Figure 2:
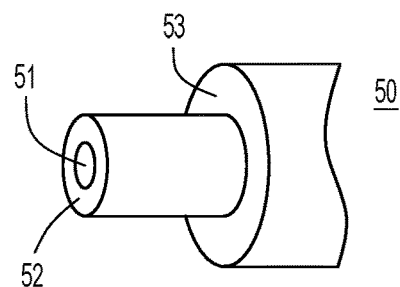
FIG. 2 is a perspective view of an end emitting optical fiber according to some implementations.

An end emitting optical fiber is an optical fiber that emits light from a terminal end of the fiber. Such emitted light is referred to herein as "end emitted light". A multimode optical fiber 50, like that shown in FIG. 2, is one example of an end emitting optical fiber wherein light is guided down the center of the fiber through the core 51 and out the end thereof. The fiber 50 includes a core 51 surrounded by a cladding 52. The cladding 52 has a lower index of refraction than the core 51 and traps the light in the core using an optical technique called "total internal reflection." The fiber 50 itself may include a coated "buffer" to protect the fiber from moisture and physical damage. The core 51 and cladding 52 are usually made of ultra-pure glass, although some fibers are all plastic or a glass core and plastic cladding. According to some implementations the core 51 has a diameter in the range of 50-250 μm and the diameter of the cladding 52 is typically around 100-500 μm. The overall diameter of the fiber system, including the buffer coating 53, is typically around 150-750 μm. Breakage of the fiber typically occurs when it is bent to a bend radius of less than about 2 millimeters.

A "transport fiber" as used herein, refers to an optical fiber that transports light longitudinally through its core to an end of the fiber with little loss. That is, the vast majority (e.g., >90%) of the light fed into a proximal end of the transport fiber is delivered to the terminal end of the fiber. As explained in more detail below, transport fibers are used in a variety of the implementations disclosed and contemplated herein to couple a light source (e.g., a laser) to a radially emitting optical fiber and/or end emitting fiber. According to some implementations, the transport fibers disclosed herein are multimode optical fibers.

It is important to note that a radially emitting optical fiber, like the examples discussed above, may also emit light from the core 20 at a terminal end of the radially emitting optical fiber 12. Thus, according to some implementations a disinfecting of a device may occur as a result of bacterial disinfecting light being emitted from both the circumference and the end of a radially emitting fiber. An optical fiber designated for this use is referred to herein as a "dual emitting fiber".

Blue light and ultra-violet light have been shown to kill or curtail the growth of certain types of unwanted bacteria that is hazardous and potentially fatal to mammalian life. Examples of such bacteria are *Staphylococcus aureus*, *Pseudomonas aeruginosa*, *Leuconostoc mesenteroides*, *Bacillus atrophaeus*, *Escherichia coli*, Coagulase-negative staphylococci etc. In treatments involving a mammal, blue light is preferred over ultra-violet light due to detrimental effects of ultra-violet light on mammalian cells and possible damage to host tissue. In accordance with some implementations disclosed herein blue light at a wavelength of between 400-495 nm and an exposure of between 100-1,000 Joules/cm$^2$ is employed to kill the unwanted bacteria. According to other implementations, ultra-violet light at a wavelength of 10-400 nm and exposure up to 6 J/cm$^2$ is employed to kill unwanted bacteria.

It is important to note that the present disclosure is in no way limited to the use of blue light and ultra-violet light to kill unwanted bacteria. As briefly explained above, the present disclosure contemplates the use of any type of light that is susceptible to killing unwanted bacteria.

Figure 3:
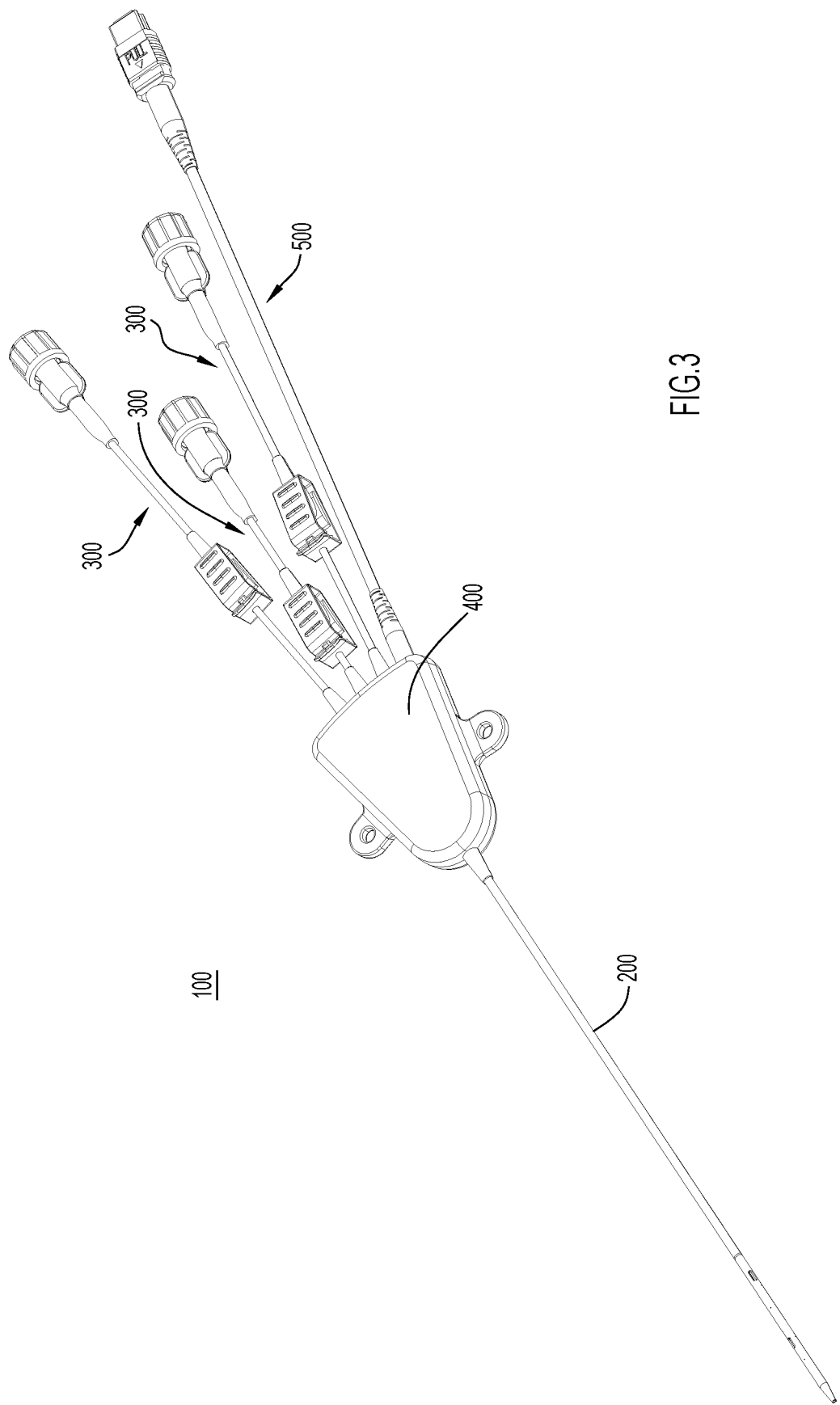
FIG. 3 is a perspective view of a central venous catheter assembly according to some implementations.
Figure 4:
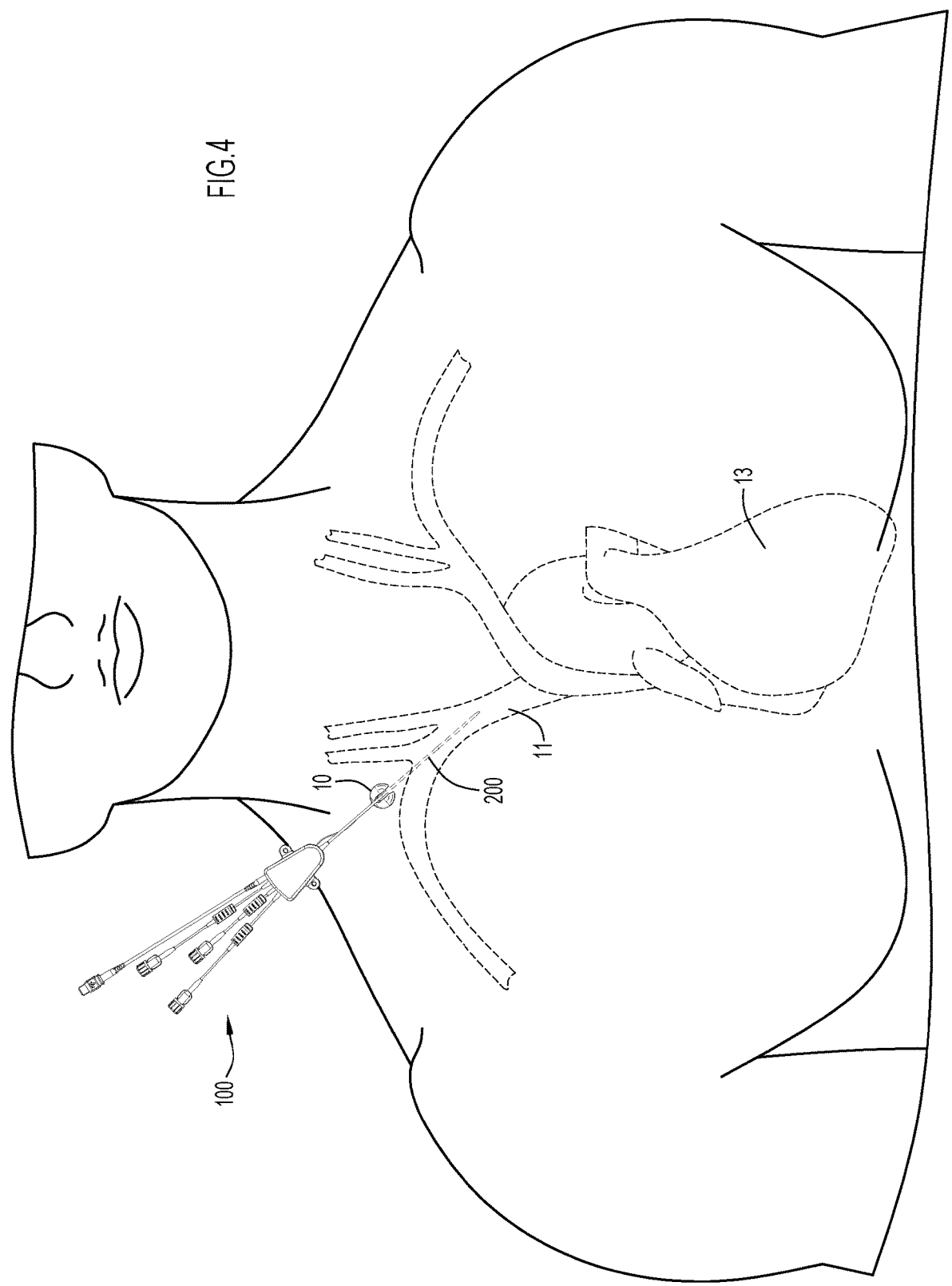
FIG. 4 illustrates a main shaft of the central venous catheter assembly of FIG. 3 inserted into the venous system of a patient at an insertion site.
Figure 5:
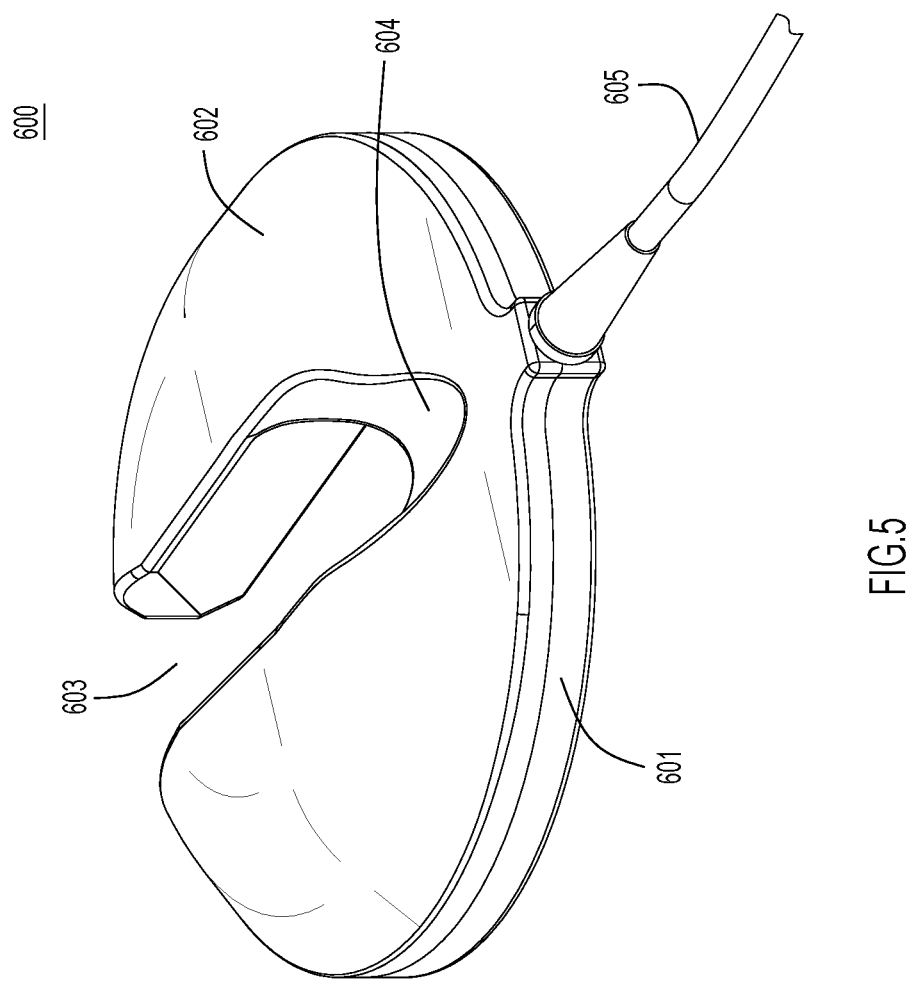
FIG. 5 shows a perspective top view of an insertion site disinfecting device according to one implementation.

FIG. 3 depicts a perspective view of a CVC 100 according to one implementation. In this implementation, the CVC includes a main shaft 200 having three working lumens through which different types of therapeutic agents may be delivered to the patient. The working lumens may also serve as conduits for receiving other types of medical instruments such as, for example, a guidewire that is used to guide the distal end portion of the main shaft 200 to a desired location in the venous system.

In the example of FIG. 3, the CVC 100 includes three infusion shafts 300 having working lumens that are fluidly and respectively coupled to the three working lumens of the main shaft 200 through a hub 400. That is, the lumen of each of the infusion shafts 300 is separately fluidly coupled to one of the working lumens of the main shaft 200. The main shaft 200 of the CVC 100 may comprise more or fewer working lumens with there being a corresponding number of infusion shafts. For example, the main shaft 200 of the CVC 100 may have one, two or four working lumens with a corresponding one, two or four infusion shafts 300.

A light delivery umbilical 500 comprising one or more transport fibers may be provided to transport light from a light source to one or more optical fibers disposed in one or more of the main shaft 200, infusion shafts 300 and hub 400. The light delivery umbilical 500 may include one or more proximal connectors 501 to couple one or more light sources to the one or more transport fibers.

A detailed description of a host of exemplary implementations is provided in co-owned application Ser. No. 15/629,494 which is incorporated by reference herein in its entirety.

As discussed above, unwanted and dangerous bacteria growth can occur on devices that are commonly used to treat patients and also around sites in which the devices are inserted into a patient. The insertion site of a main shaft of a CVC is an example of such a site. FIGS. 5-30 illustrate a light disinfecting devices 600 that are adapted to deliver bacterial disinfecting light to an insertion site, such as the insertion site of a main shaft of a CVC. It is appreciated that the light disinfecting devices and assemblies disclosed herein may be used to bacterially disinfect any desired surface and not just the insertion sites of medical devices. As will be discussed in more detail below, the surface may include a wound or any other site on the human body. The surface may also be associated with equipment or components outside the medical field, such as water processing plants, food processing plants, dairies, livestock habitation facilities, etc.

Figure 6:
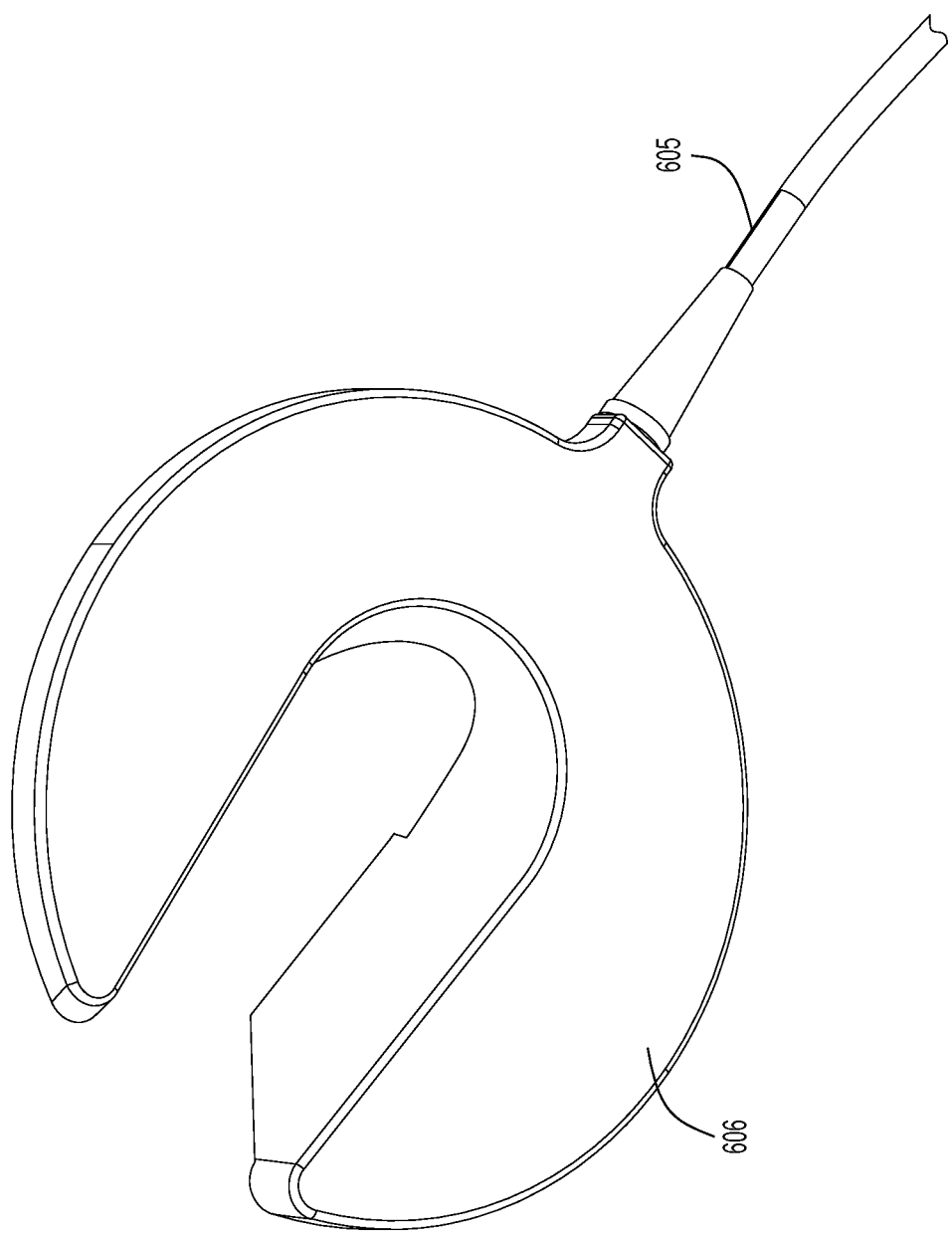
FIG. 6 shows a perspective bottom view of the disinfecting device of FIG. 5.

With reference to FIGS. 5-13C, the light disinfecting device 600 includes a base 601 having a bottom surface 606 through which bacterial disinfecting light exits to irradiate a surface in proximity thereof. In the implementation of FIG. 6, the bottom surface 606 is flat. However, according to other implementations the bottom surface 606 may be a non-planar surface that comprises, for example, one or more of an inclined, declined, curved, convex and concave surfaces. Device 600 also includes a cover 602. The cover 602 and base 606 each comprise a vertically extending through opening that together formulate a horizontal slotted opening 603 that has a distal open end. The open ended slotted opening 603 enables the device 600 to be easily positioned across, for example, a medical device (e.g. catheter) insertion site of a patient. That is, the device 600 may be positioned around the medical device by introducing the medical device into the open distal end of the slotted opening 603 and sliding the device until the insertion site is, for example, centrically located inside the device 600. According to one implementation, the cover 602 includes a saddle 604 in the form of a recess that includes a bottom surface on which at least a portion of the medical device (e.g. main shaft of a CVC) may rest when the light disinfecting device is positioned bout the insertion site.

Figure 7:
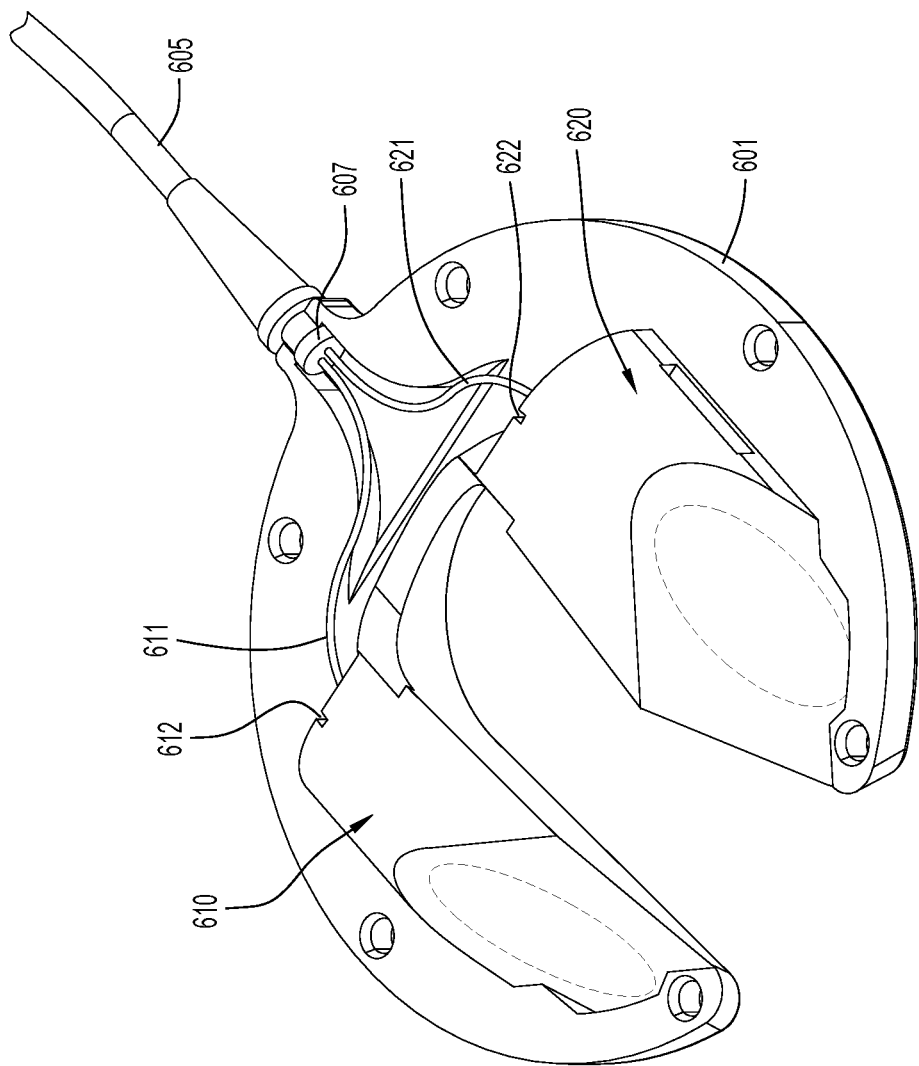
FIG. 7 shows a perspective front view of the disinfecting device of FIG. 5 with the cover removed.
Figure 8:
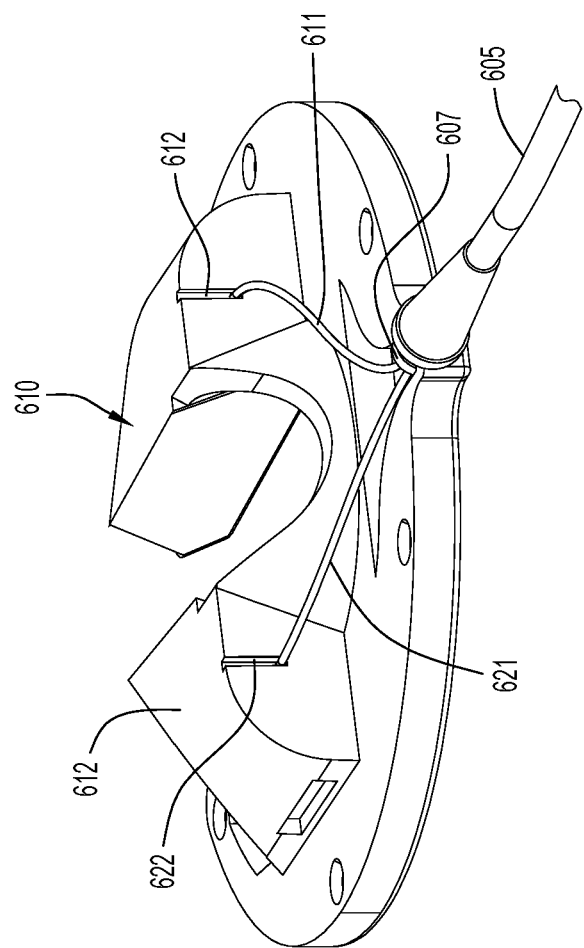
FIG. 8 shows a perspective rear view of the disinfecting device of FIG. 7.
Figure 9:
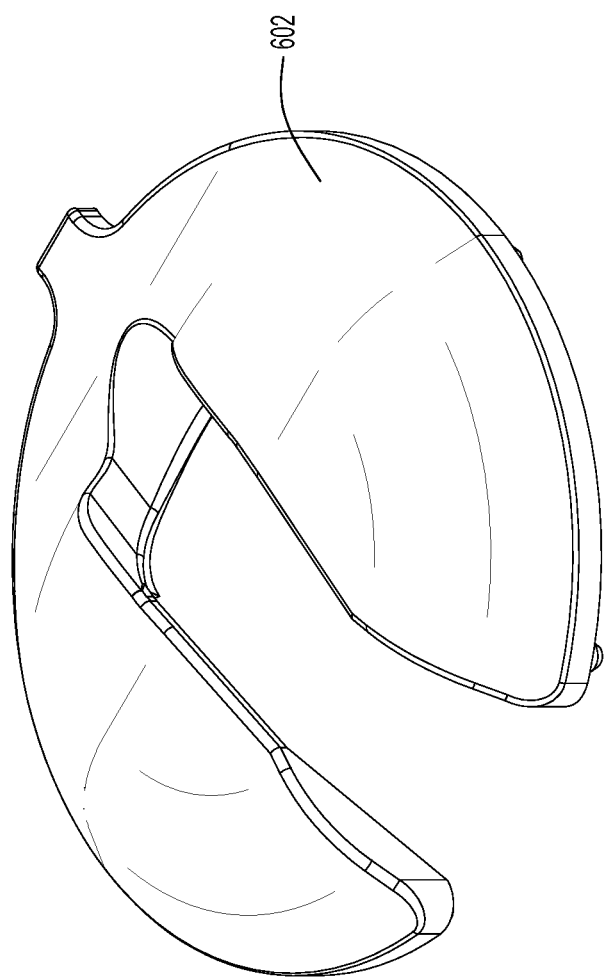
FIG. 9 is a perspective top view of the cover of the disinfecting device of FIG. 5.

In the implementation of FIG. 7 the light disinfecting device 600 includes first and second optical bodies 610 and 620, respectively. Each of the first and second optical bodies is configured to respectively receive light emanated at the terminal end of optical fibers 611 and 621, and to alter the trajectory of the light so that it passes through the bottom surface 606 of the base 601. It is appreciated that the light disinfecting device may comprise only one optical body or may comprise three or more optical bodies.

As discussed above, a radially emitting optical fiber may also emit light from a terminal end thereof in addition to the light it radially emits. An optical fiber designated for this use is referred to herein as a "dual emitting optical fiber". According to some implementations the end emitting optical fibers 611 and 621 are not dual emitting optical fibers and are configured to only axially end emit light with respect to the longitudinal axis of the optical fiber core. That is, no light is emitted from any side of the optical fiber with all light propagating from the terminal end in a forward direction toward an optical surface of an optical body (e.g. forward towards the first refractive optical surface 615 of the optical body 610 of FIG. 11A). This type of optical fiber is referred to herein as an "end emitting optical fiber". According to other implementations each of the optical fibers 611 and 621 is a dual emitting optical fiber in which a majority of the light emitted by the optical fiber is axially end emitted light. According to some implementations each of the optical fibers 611 and 621 is a dual emitting optical fiber in which greater than 80% of the light emitted by the optical fiber is axially end emitted light. According to some implementations each of the optical fibers 611 and 621 is a dual emitting optical fiber in which greater than 90% of the light emitted by the optical fiber is axially end emitted light. According to some implementations each of the optical fibers 611 and 621 is a dual emitting optical fiber in which greater than 95% of the light emitted by the optical fiber is axially end emitted light.

An optical fiber umbilical cord 605 has a distal end 607 that is connectable to the light disinfecting device base as shown in FIG. 7. Each of the optical fibers 611 and 621 emerges from the distal end 607 of the optical fiber umbilical cord 605 and extends into a respective recess or opening 612 and 622 in optical bodies 610 and 620 where the distal end of the optical fibers reside. A proximal end (not shown) of the optical fibers 611 and 621 is optically coupled to one or more light sources (not shown). The one or more light sources may include, for example, lasers or light emitting diodes. According to some implementations each of the optical fibers 611 and 621 is optically coupled to different light sources, while according to other implementations the optical fibers 611 and 612 are optically coupled to a common light source.

Figure 12:
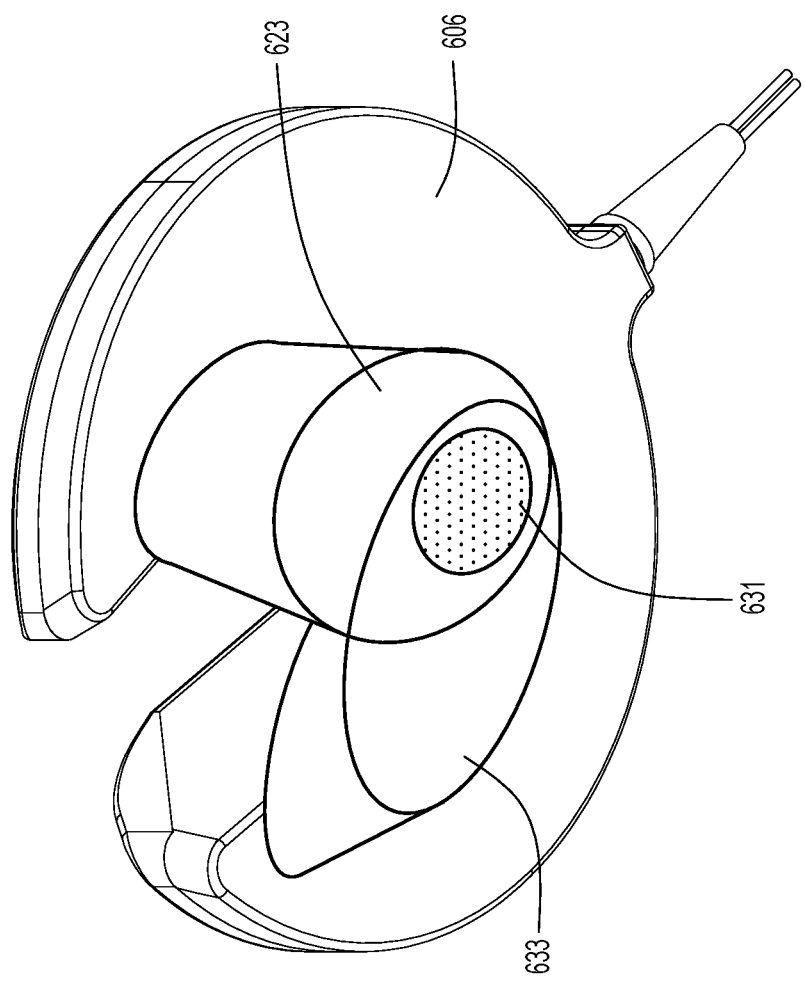
FIG. 12 illustrates a bottom perspective view of the disinfecting device of FIG. 7 that shows overlapping first and second light beams propagating from the bottom of the disinfecting device.

According to one implementation each of the first and second optical bodies 610 and 620 is similarly configured to direct light emitted from the end of the optical fiber 611,621 downward toward the base 601 of the light disinfecting device 600. According to some implementations the first and second optical bodies are configured such that light 633 emanating from the base of the first optical body 610 and the light 623 emanating from the base of the second optical body 620 overlap with one another as shown in FIG. 12. In use, the overlap of the light occurs at a target disinfecting location 631. According some implementations the first and second optical bodies 610 and 620 are located on opposite sides of the opening 603 and are substantial mirror images of one another as shown in FIG. 7.

Figure 11A:
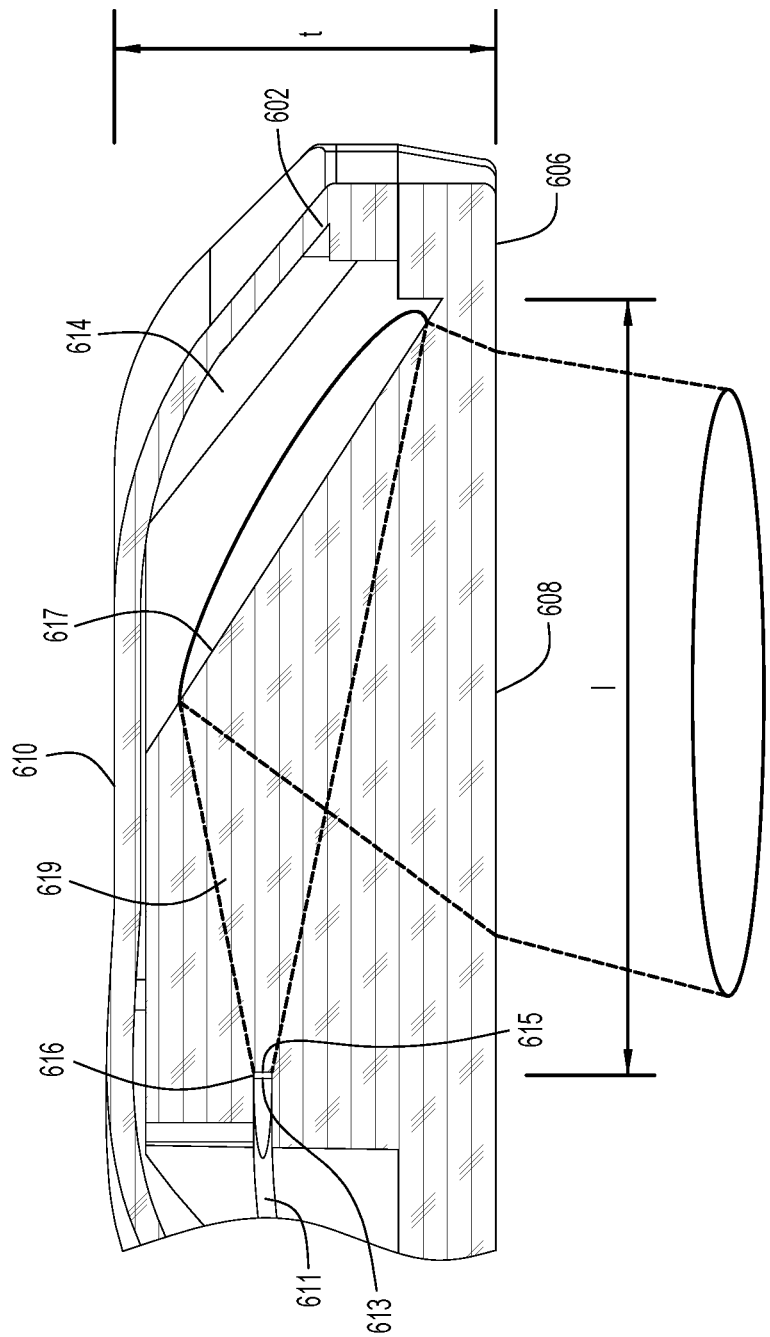
FIG. 11A illustrates a cross-sectional side view of an optical body of a disinfecting device according to one implementation.

FIG. 11A illustrates a cross-sectional side view of an optical body according to one implementation. In regard to the implementation of FIG. 7, one or both of the optical bodies 610 and 620 has a configuration consistent with that shown in FIG. 11A. According to some implementations the first and second optical bodies 610 and 620 are of similar construction but are configured so as to each direct light inward toward the central opening 603 of the disinfecting device 600. In the disclosure that follows reference to the first optical body 610 is made. It is to be appreciated that according to some implementations the disclosure is equally applicable to the second optical body 620 in that the two optical bodies are of the same or similar construction.

Figure 11B:
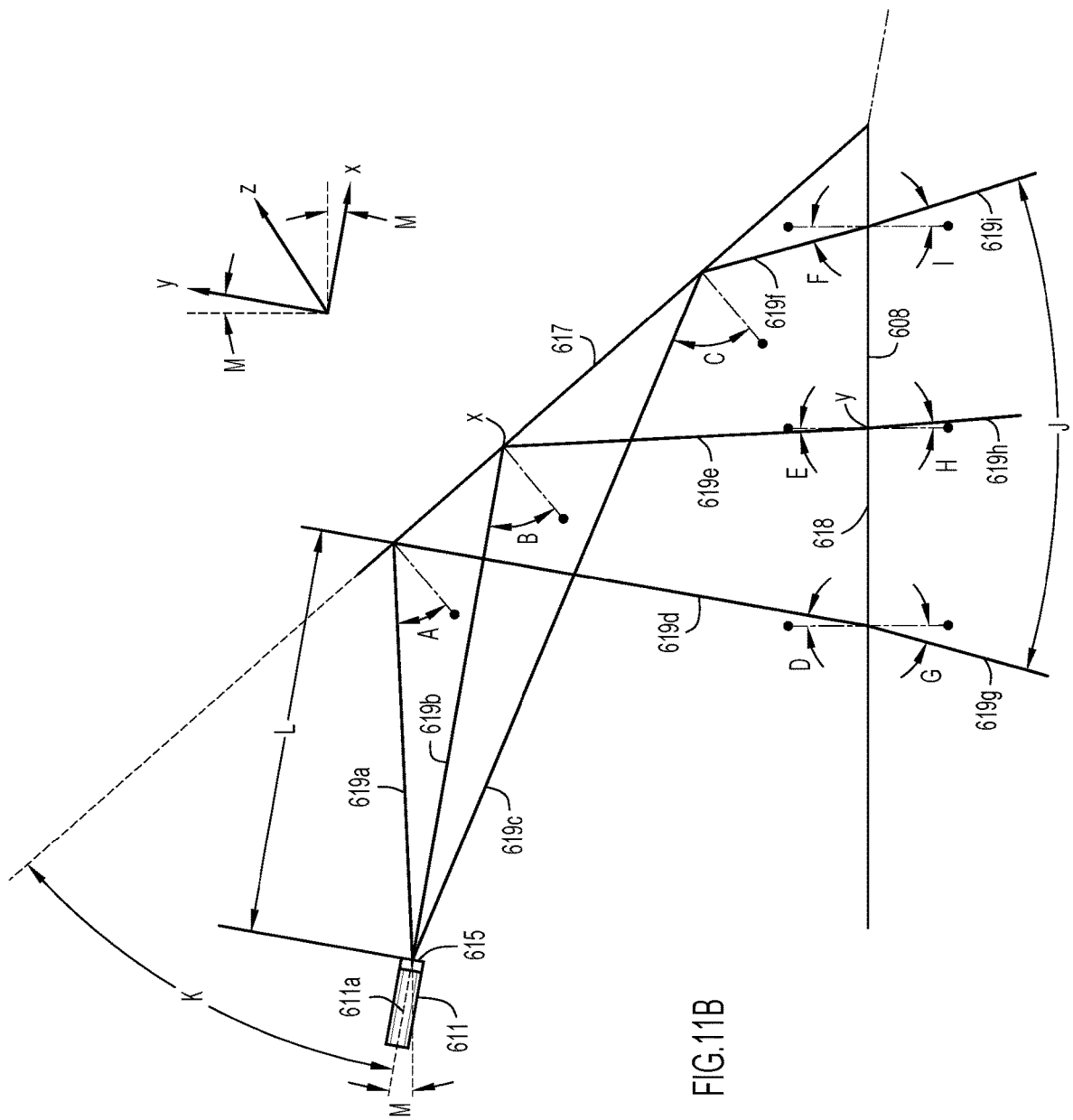
FIG. 11B is a diagram illustrating the light flow path between optical surfaces in accordance with one implementation.

In the implementation of FIG. 11A the optical fiber 611 is an end emitting fiber wherein a totality of the light beam propagates from the end 613 of the optical fiber 611 in a forward direction towards a reflective surface 617 that in turn reflects the light beam rearward and downward toward the base 601 of the light disinfecting device 600. According to some implementations the reflective surface 617 is also angularly oriented or shaped to cause the light beam to be directed inward toward the central opening 603 in the disinfecting device 600. In the implementation of FIGS. 11A and 11B the first optical body 610 comprises a first refractive optical surface 615, a second refractive optical surface 618 and the reflective surface 617, with the reflective surface 617 being located in a pathway of the light beam 619 between the first and second refractive optical surfaces. Those portions of the first optical body 610 located between the first refractive optical surface 615, reflective surface 617 and second refractive optical surface 618 are made of a material that is substantially transparent or at least translucent to the light emitted by the optical fiber 611. According to some implementations the material is a Teflon or a polycarbonate.

In regard to the first and second refractive optical surfaces 615 and 618 the trajectory of the light beam is altered as a result of being refracted. Refraction is a deflection from a straight path undergone by a light ray or energy wave in passing obliquely from one medium (such as air) into another (such as glass or a plastic) in which its velocity is different.

In regard to the reflective surface 617, according to some implementations all portions of the light beam 619 impinging on it are totally reflected downward and rearward onto the second refractive optical surface 618. In the implementation of FIGS. 11A-B the entirety of the light beam 619 emitted by the first optical fiber 611 is caused to pass through the first refractive optical surface 615 and onto the reflective surface 617. According to some implementations the reflective surface 617 is a continuous surface that is capable of reflecting the light beam 619 in a substantially uniform manner as depicted in FIG. 11. The meaning of the term "continuous surface" is not meant to include a medium in which spatially separated reflective particles or voids are used to reflect or scatter light.

According to some implementations the reflective surface 617 comprises a light reflector in the form of, for example, a mirror, a metal, a film such as a layer of light reflective paint, etc.

According to other implementations the reflective surface 617 is a total internal reflection optical surface. Total internal reflection is the phenomenon which occurs when a propagated wave strikes a medium boundary at an angle larger than a particular critical angle normal to the incident surface. If the refractive index is lower on the opposing side of the boundary and the incident angle is greater than the critical angle, the wave cannot pass through and is entirely internally reflected. The critical angle is the angle of incidence above which the total internal reflection occurs. This is particularly common as an optical phenomenon, where light waves are involved.

When a wave reaches a boundary between different materials with different refractive indices, the wave will in general be partially refracted at the boundary surface, and partially reflected. However, if the angle of incidence is greater (i.e. the direction of propagation is closer to being parallel to the boundary) than the critical angle—the angle of incidence at which light is refracted such that it travels along the boundary—then the wave will not cross the boundary, but will instead be totally reflected back internally. This can only occur when the wave in a medium with a higher refractive index reaches a boundary with a medium of lower refractive index. For example, it will occur with light reaching air from plastic, but not when reaching plastic from air.

According to some implementations the outer side of surface 617 is bounded by a medium having a refractive index less than the refractive index of the material that forms the first optical body 610. According to some implementations the first optical body 610 is made of a polymer (e.g. polycarbonate) and the lower refractive index medium is air.

In the context of the present application, the term "reflector" and "light reflector" do not encompass a total internal reflection optical surface, but instead include polished surfaces, mirrors, metals and the like that reflect light regardless of the incident angle.

According to some implementations an index matching material, such as a gel or adhesive 616, is positioned in a gap that separates the end 613 of the first optical fiber 611 from the end wall of lumen 612. The index matching material is selected to have a refractive index between that of the core of the first optical fiber 611 and that of the first refractive optical surface 615 formed in or located on the end wall of lumen 612.

As noted above, according to some implementations the first and second optical bodies 610 and 620 may be made of a polymeric material. According to some implementations the polymeric material has an index of refraction of between about 1.4 to about 1.7 as compared to air that has an index of refraction of 1.0. The polymeric material may be, for example, a Makrolon® polycarbonate produced by Covestro having an index of refraction 0f 1.618. In the implementation of FIGS. 11A-B there are three optical surfaces used to direct light from the first optical fiber 611 to a target location located at or near the bottom surface 606 of the base 601. As explained above, according to some implementations the reflective surface 617 is a total internal reflection optical surface that is bounded on one side by a plastic material and on the other side by air. In addition, the angle of inclination of the reflective surface 617 is chosen so that the incident angle at which light impinges on the surfaces is greater than the critical angle, the critical angle being the inverse sine of the ratio of the index of refraction of air over the index of refraction of the plastic that forms the first optical body 610. With the index of refraction of plastics ranging between about 1.4 to about 1.7, according to some implementations the critical angle is greater than about 46 degrees to greater than about 36 degrees respectively depending on the specific index of refraction of the plastic that is used in the construction of the first optical body 610.

FIG. 11B is an exemplary diagram of an optical body showing a pathway of the light beam 619 as it passes through and out of the optical body. The light beam exiting the first refractive optical surface 615 is bound by outer light rays 619*a* and 619*c*. Light ray 619*b* represents a light ray positioned centrically between the outer light rays 619*a* and 619*c* as the light beam exits the first refractive optical surface 615. The light rays 619*a*-*c* representing the light beam 619 strike the reflective surface 617 at incident angles A, B and C, respectively. According to one implementation the incident angles A, B and C are 38.8 degrees, 51.5 degrees and 64.2 degrees respectively. The light beam reflected from the reflective surface 617 is represented by rays 19*d*, 19*e* and 19*f* that respectively represent reflected light rays 19*a*, 19*b* and 19*c*. The light rays 619*d*-*f* strike the second refractive optical surface 618 at incident angles D-F, respectively. According to one implementation the incident angles D, E and F are 9.7 degrees, 3.0 degrees and 16.7 degrees, respectively. The light beam exiting the second refractive surface 618 is represented by light rays 619*g*-*i*. As shown in FIG. 11B the composition and configuration of the optical body results in a divergence in the light beam as it exits the second refractive optical surface 618. According to one implementation the divergence angles G, H and I of diverging rays 619*g*, 619*h* and 619*i* are 15.8 degrees, 4.9 degrees and 17.3 degrees, respectively. Accordingly, a light beam having a spread J of about 33 degrees is produced at the outlet of the second refractive optical surface 618.

According to one implementation the angles K and M are about 38.5 degrees and 10.0 degrees, respectively, the distance L is about 6 millimeters, and the straight-line distance between locations x and y is about 4 millimeters.

According to one implementation the first refractive optical surface 615 is a flat surface oriented orthogonal to the longitudinal axis 611*a* of the optical fiber 611. That is, the first refractive optical surface 615 lies in a plane that is parallel to the y-z plane as depicted in FIG. 11B. (In the implementation of FIG. 11B the x and y axes of the xyz coordinate system is rotated by the angle M.) According to other implementations the first refractive optical surface 615 is curved (convex or concave) in order to obtain a desired spread of the light beam exiting the surface 615. According to other implementations the first refractive optical surface 615 is oriented non-parallel to the y-z plane and is tilted upward or downward about the z-axis and/or to a side about the y-axis in order to minimize back reflectance into the optical fiber 611 and to facilitate light coupling into the polymeric material (or other material) that forms the optical body 610. According to some implementations the surface 615 is tilted about the z-axis by about 2 to about 10 degrees, and preferably between about 4 to about 8 degrees. According to some implementations the surface 615 is tilted about the y-axis by about 2 to about 10 degrees, and preferably between about 4 to about 8 degrees.

According to one implementation the reflective surface 617 is a flat surface oriented non-orthogonal to the longitudinal axis 611*a* of the optical fiber 611. According to one implementation, as shown in FIGS. 11A and 11B, the reflective surface 617 is oriented non-parallel to the y-z plane and is tilted with respect to the z-axis so that the light beam impinging of the reflective surface is reflected downward toward the second refractive optical surface 618. According to some implementations the reflective surface 617 is further tilted to face inward or to face outward for the purpose of directing the reflect light toward one side or the other of the optical body. In the implementation of FIGS. 7, 8, 11A and 11B the reflective surface 617 is tilted to face inward to cause the reflected light (e.g. rays 619e-f) to be directed inward in a direction toward the central opening 603 of the light disinfecting device 600.

In the implementation of FIGS. 11A and 11B, the second refractive optical surface 618 is flat. According to other implementations, as will be discussed in detail below in regard to the implementations of FIGS. 13A-C, the second refractive surface 618 may be curved (convex or concave) in order to obtain a desired spread of the light exiting the second refractive optical surface 618.

An advantage of introducing light into an optical body that initially propagates in a non-orthogonal direction with respect to a treatment surface and directing the light from the end of an optical fiber to the treatment site using three or more optical surfaces is that it provides a great deal of flexibility in producing a desired irradiance (e.g. 5 mW/cm$^2$- 500 mW/cm$^2$) of a desired size (e.g. 0.5 cm$^2$-900 cm$^2$) in a relatively compact manner. For example, one or more of the location, angular orientation, shape and curvature of the optical surfaces 615, 617 and 618 may be manipulated to produce a desired disinfecting result in terms of irradiance and size. According to one implementation, the optical body of FIG. 11A has a thickness "t" of between about 8-10 millimeters and a length "1" of between about 10-15 millimeters. In addition, as explained above, multiple optical bodies with such features may be incorporated into a single light disinfecting device (such as that provided in the disinfecting device of FIG. 7) in order to produce a desired disinfecting result. FIG. 12, as explained above, is an example in which two light beams from two separate optical bodies 610 and 620 are caused to overlap one another to create a desired irradiance across a desired area. Irradiance is cumulative in the area(s) of overlap.

In implementations employing multiple optical bodies, each of the optical bodies and its associated optical fiber(s) are configured to equally contribute to the irradiance produced at the outlet of the second refractive optical surface 618. According to other implementations each of the optical bodies and its associated optical fiber(s) are configured so as to not equally contribute to the irradiance produced at the outlet of the second refractive optical surface 618.

Figure 10:
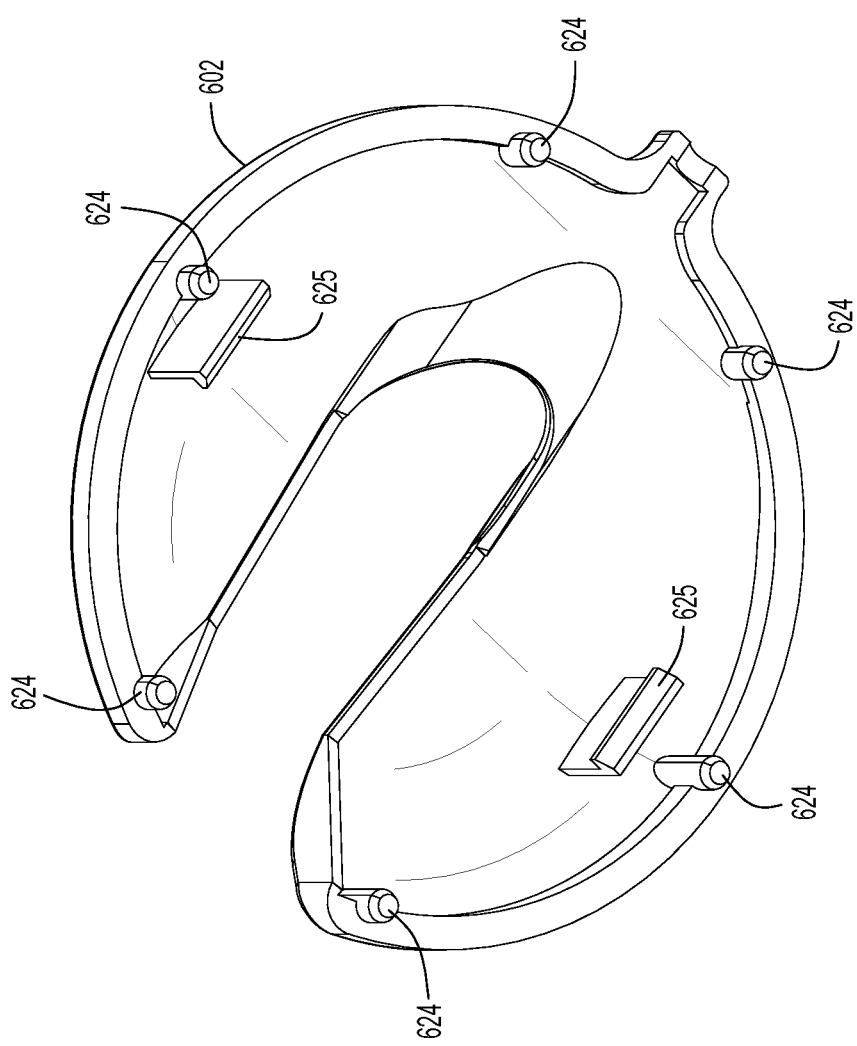
FIG. 10 is a perspective bottom view of the cover of the disinfecting device of FIG. 5.

Although not required, according to some implementations the light disinfecting device 600 includes a cover 602 that resides over the one or more optical bodies and optical fibers of the device in order to protect the components from external influences (e.g. touching, contamination, etc.). In the implementation of FIG. 11A the air gap 614 resides between the reflective optical surface 617 and the inner surface of the cover 602. As shown in FIG. 10, according to some implementations the bottom of the cover 602 is equipped with a plurality of posts 624 and a pair of clips 625 that are configured to mate with complementary receptacles in the base of the light disinfecting device 600 to hold the cover securely to the base.

Figure 13A:
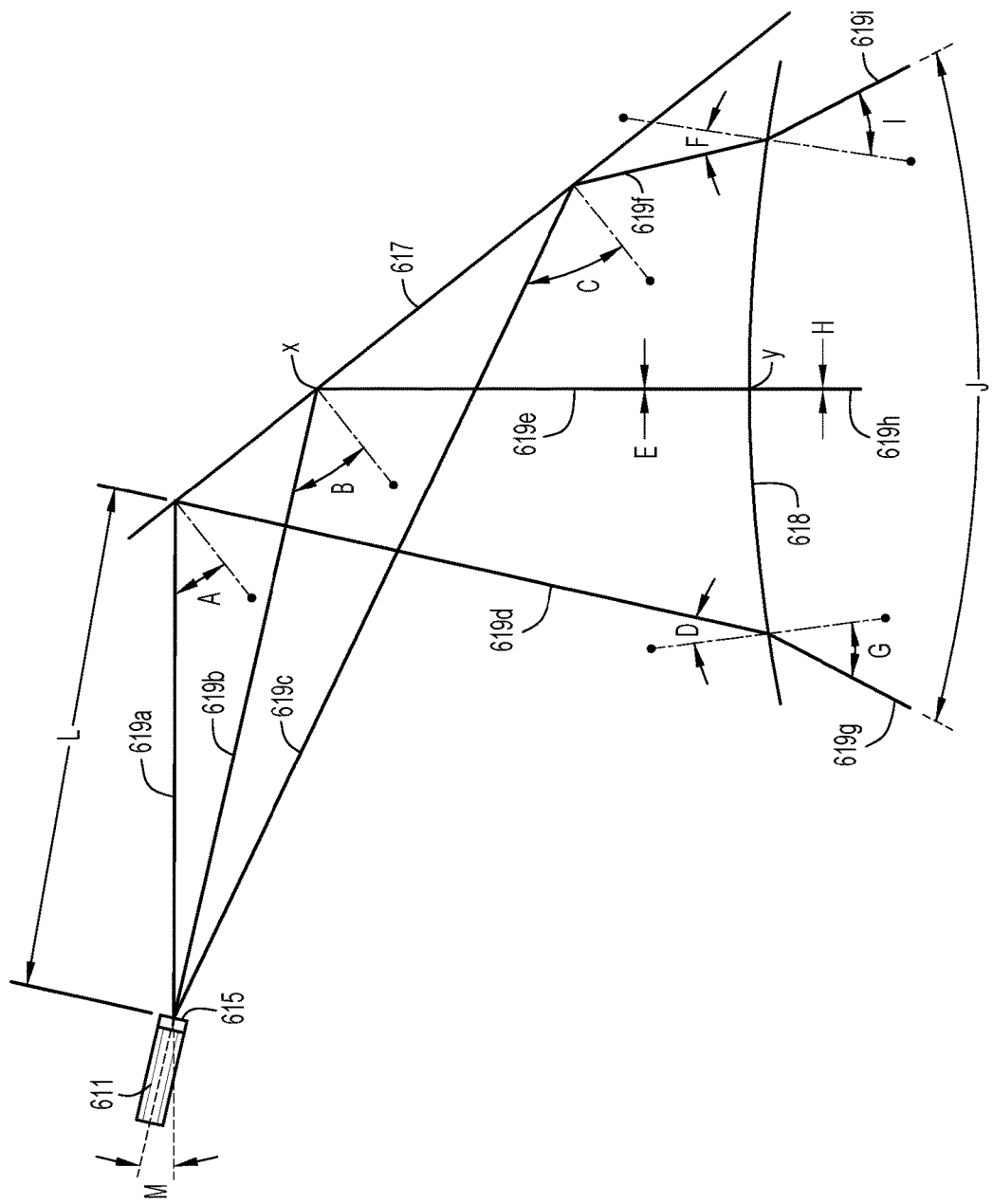
FIG. 13A is a diagram illustrating the light flow path between optical surfaces of an optical body in accordance with another implementation.

FIG. 13A is a diagram illustrating the light flow path between the optical surfaces of an optical body in accordance with another implementation. As with the implementation of FIGS. 11A and 11B, the optical body 640 (see FIG. 13C) includes a first refractive optical surface 615, a second refractive optical surface 618 and a reflective surface 617 located between the first and second refractive optical surfaces. The optical body 640 is similar in construction to the implementations of the first optical body 610 described above except that the second refractive optical surface is curved. In the implementation of FIG. 13A the optical surface 618 is convex to create a greater spread of light J at the outlet of the second refractive optical surface 618 as compared to that of the implementation of FIG. 11B. According to other implementations, however, the second refractive optical surface 618 may be concave to produce a smaller spread J at the outlet of the second refractive optical surface 618 as compared to that of the implementation of FIG. 11B. By altering the curvature of the second refractive optical surface 618 the irradiance and surface area of the light beam exiting the second refractive optical surface 618 can be modified.

With continued reference to FIG. 13A, the light beam exiting the first refractive optical surface 615 is bound by outer light rays 619a and 619c. Light ray 619b represents a light ray positioned centrically between the outer light rays 619a and 619c as the light beam exits the first refractive optical surface 615. The light rays 619a-c representing the light beam 619 strike the reflective surface 617 at incident angles A, B and C, respectively. According to one implementation the incident angles A, B and C are 38.8 degrees, 51.5 degrees and 64.2 degrees respectively. The light beam reflected from the reflective surface 617 is represented by rays 19d, 19e and 19f that respectively represent reflected light rays 19a, 19b and 19c. The light rays 619d-f strike the second refractive optical surface 618 at incident angles D, E and F, respectively. According to one implementation the incident angles D, E and F are 21.5 degrees, 0.0 degrees and 21.5 degrees, respectively. The light beam exiting the second refractive surface 618 is represented by light rays 619g-i. The composition and configuration of the optical body 640 results in a divergence in the light beam as it exits the second refractive optical surface 618. According to one implementation the divergence angles G, H and I of diverging rays 619g, 619h and 619i are 36.4 degrees, 0.0 degrees and 36.4 degrees, respectively. Accordingly, a light beam having a spread J of about 55 degrees is produced at the outlet of the second refractive optical surface 618.

According to one implementation the angles K and M are about 38.5 degrees and 10.0 degrees, respectively, the distance L is about 6 millimeters, and the straight-line distance between locations x and y is about 4 millimeters.

In the implementation of FIG. 13A the second refractive optical surface 618 has a radius of curvature of 15.0 millimeters. According to other implementations the radius of curvature is between about 1.0 to about 25.0 millimeters.

Figure 13B:
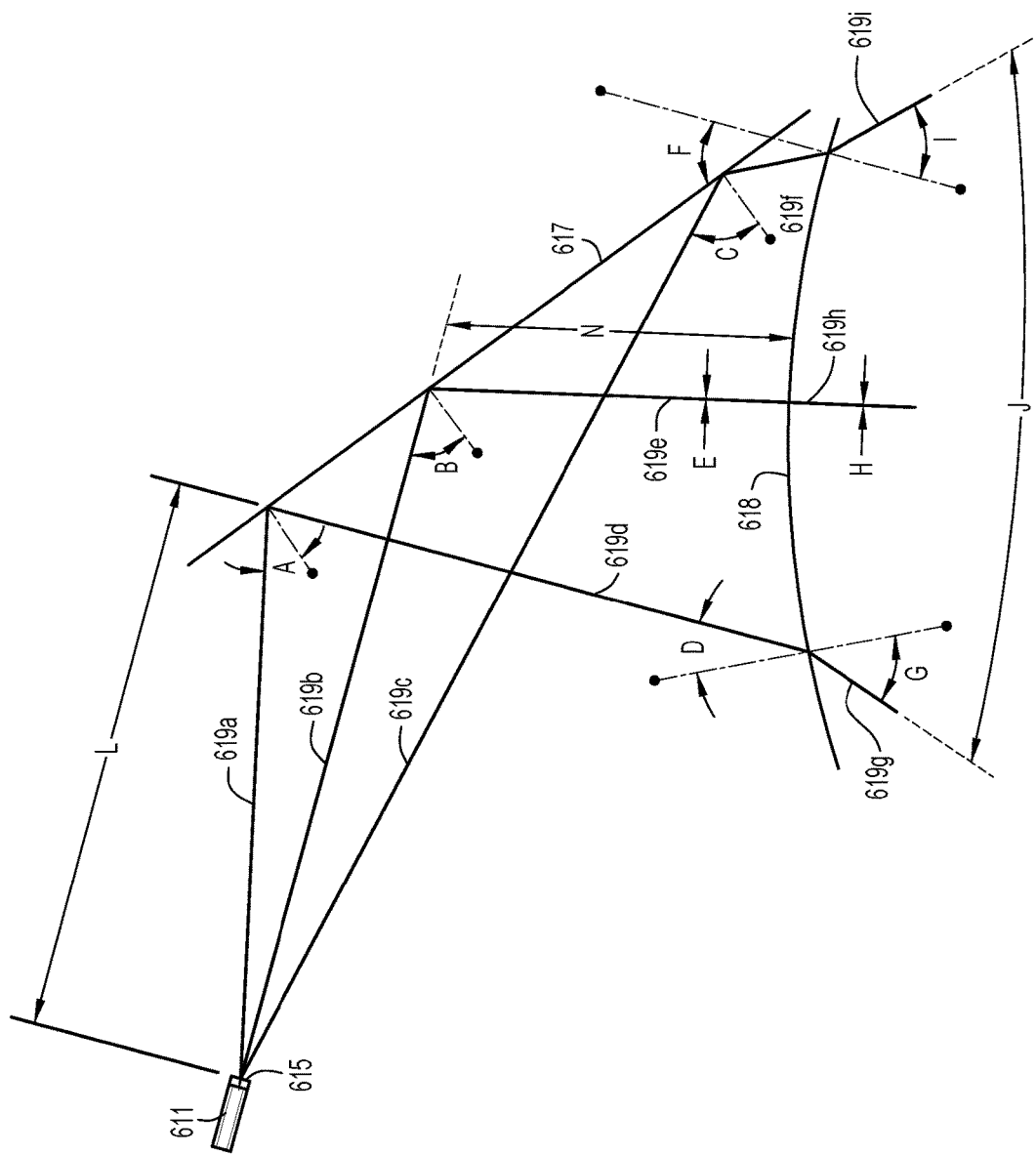
FIG. 13B is a diagram illustrating the light flow path between optical surfaces of an optical body in accordance with another implementation.

FIG. 13B is a diagram illustrating the light flow path between the optical surfaces of an optical body in accordance with another implementation. The optical body of FIG. 13B is similar to the optical body of FIG. 13A except that the distance L between the first refractive optical surface 615 and the reflective surface 617 and the distance N between the reflective surface 617 and the second refractive optical surface 618 is greater resulting in a larger spread of light at the outlet of the second refractive optical surface 618.

With continued reference to FIG. 13B, the light beam exiting the first refractive optical surface 615 is bound by outer light rays 619a and 619c. Light ray 619b represents a light ray positioned centrically between the outer light rays 619a and 619c as the light beam exits the first refractive optical surface 615. The light rays 619a-c representing the light beam 619 strike the reflective surface 617 at incident angles A, B and C, respectively. According to one implementation the incident angles A, B and C are 38.8 degrees, 51.5 degrees and 64.2 degrees respectively. The light beam reflected from the reflective surface 617 is represented by rays 19*d*, 19*e* and 19*f* that respectively represent reflected light rays 19*a*, 19*b* and 19*c*. The light rays 619*d-f* strike the second refractive optical surface 618 at incident angles D-F, respectively. According to one implementation the incident angles D, E and F are 26.1 degrees, 0.0 degrees and 26.1 degrees, respectively. The light beam exiting the second refractive surface 618 is represented by light rays 619*g-i*. The composition and configuration of the optical body results in a divergence in the light beam as it exits the second refractive optical surface 618. According to one implementation the divergence angles G, H and I of diverging rays 619*g*, 619*h* and 619*i* are 45.3 degrees, 0.0 degrees and 45.3 degrees, respectively. Accordingly, a light beam having a spread J of about 64 degrees is produced at the outlet of the second refractive optical surface 618.

Figure 13C:
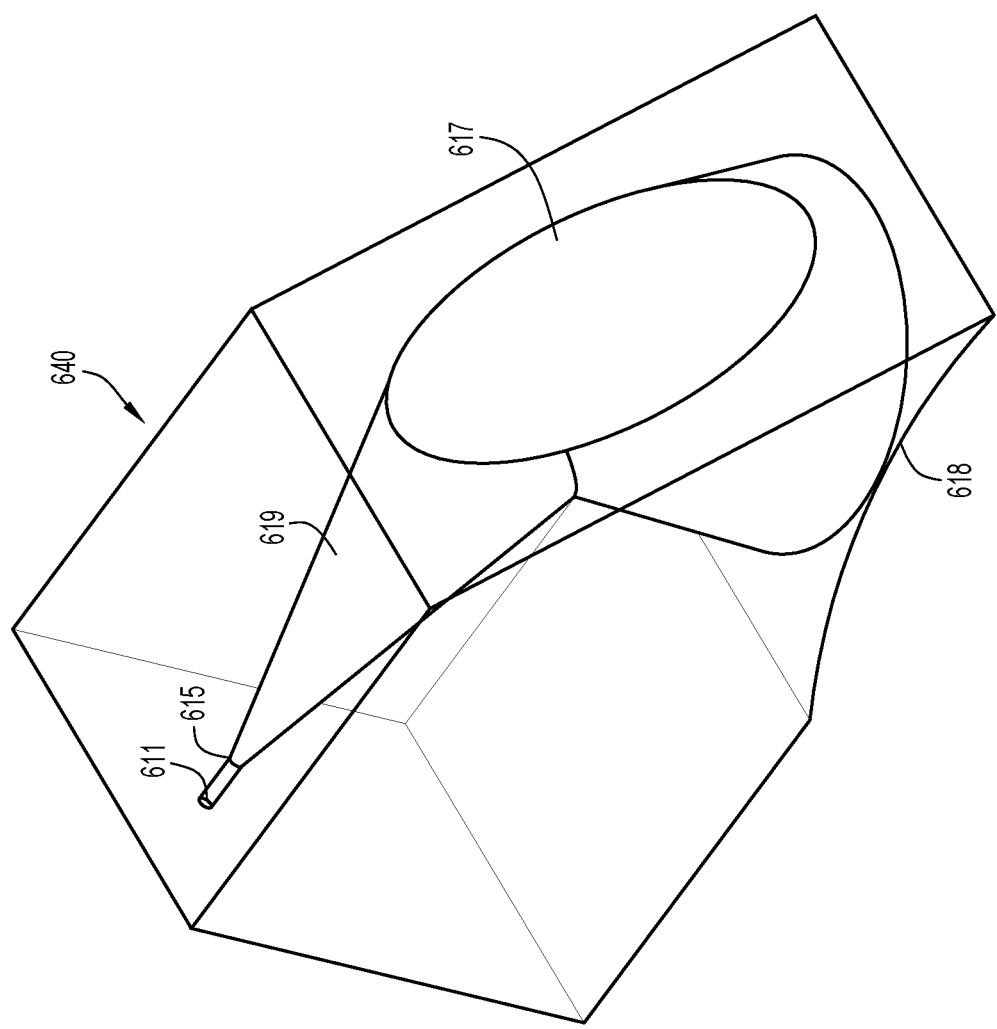
FIG. 13C illustrates a perspective view of an optical body according to one implementation.

In regard to the implementations of FIGS. 13A-C it is appreciated that the optical surfaces 615, 617 and 618 may possess any of a variety of angular orientation and shapes as discussed in the description of the implementations of FIGS. 11A and 11B.

As discussed above, a light disinfecting device may include one or more optical bodies. FIG. 14 is a schematic representation of a light disinfecting device 650 that includes four optical bodies 651*a-d* that are each configured to direct disinfecting light 654*a-d* downward to a target area 652. In the implementation of FIG. 14 each of the optical bodies 651*a-d* is respectively optically coupled to an optical fiber 653*a-d*. The optical bodies 651*a-d* may each comprise the features of the optical bodies hereto and hereafter described.

As discussed above, in FIG. 11A the end of the optical fiber 611 is shown positioned in a recess or opening of the optical body 610 with the end 613 of the optical fiber spaced a distance from the first refractive optical surface 615. FIG. 17 shows a partial cross-sectional side view of an optical body 610 according to one implementation wherein a port 678 is provided to facilitate the introduction of the index matching material 616 into the opening 612. An intervening index matching gel or adhesive 616 is disposed between the end 613 of the optical fiber 611 and the first refractive optical surface 615. According to some implementations the optical fiber 611 is an end emitting optical fiber like that of FIG. 2 with the distal end section residing inside the opening 612 of the optical body 610.

As discussed above, according to some implementations the first refractive optical surface 615 may be tilted/angled in order to prevent a reflectance of light back into the core of the optical fiber 611. FIG. 18A illustrates such an implementation wherein the angle A with respect to the longitudinal axis 611*a* of the optical fiber 611 is between about 2 to about 10 degrees, and preferably between about 4 to about 8 degrees. In conjunction with, or in lieu of providing a tilted/angled first refractive optical surface 615, the end 613 of the optical fiber 611 may also be angled by an angle B with respect to the longitudinal axis 611*a* of the optical fiber 611 as shown in FIG. 18B for the same purpose of preventing the back reflectance of light into the fiber core. According to some implementations the angle B is between about 2 to about 10 degrees, and preferably between about 4 to about 8 degrees.

Figure 15B:
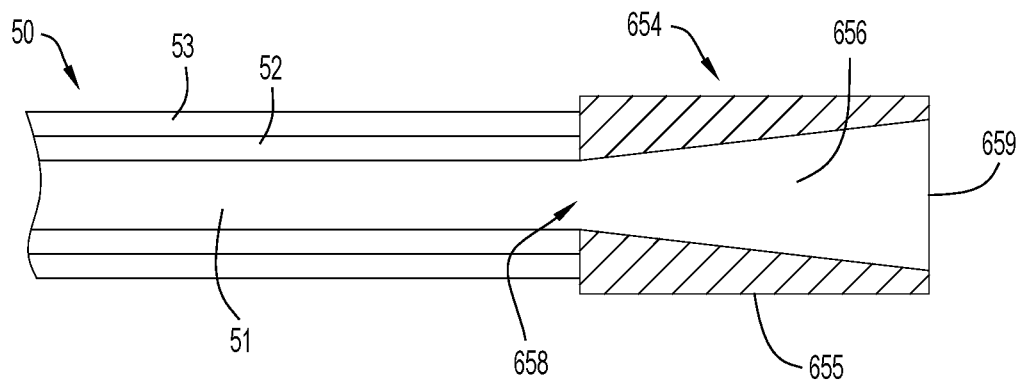
FIGS. 15A and 15B illustrate an end emitting optical fiber having an end cap attached to a distal end thereof.
Figure 15A:
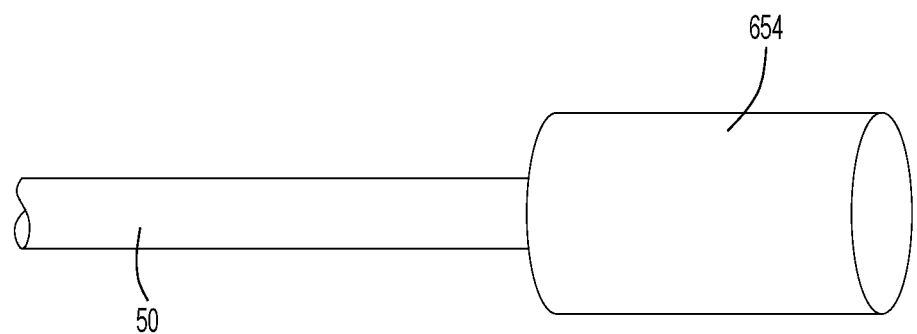

FIG. 15A shows a perspective side view of an end portion of an end emitting optical like that described above in conjunction with FIG. 2. In the implementation of FIG. 15A the distal end of the end emitting optical fiber 50 is attached to and optically coupled to an end cap 654. FIG. 15B shows a cross-section of the end cap 654 according to one implementation. The fiber includes a glass or polymer core 51 with a cladding 52 and a buffer layer 53 disposed about the core. The end cap 654 includes a cylindrical body 655 that houses a medium 656 that is optically coupled to the fiber core 51. The medium is transparent to the light it receives from the core 51 and has an index of refraction that is the same or close to that of the fiber core 51. The medium is sized and shaped so that the light that exits the distal end 659 of the end cap 654 has a power density that is lower than the power density of the light when it leaves the fiber core 51. This is accomplished by widening the light beam received from the fiber core. The widening of the light beam occurs as a result of the medium having a greater diameter than that of the fiber core. In the example of FIG. 15B, the diameter of the medium 656 increases between its proximal and distal ends 658 and 659, respectively. However, according to other implementations the medium may be cylindrical or spherical in shape. Coupling of the end cap medium 656 to the fiber core 51 may occur in several ways. According to one method the proximal end of the medium is fused with the fiber core. According to other implementations the medium 656 is formed from the fiber core 51.

According to each of the implementations disclosed herein the distal end of the optical fiber that delivers light into the respective optical bodies (e.g. optical bodies 610 and 620) may be equipped with an end cap 654. In such implementations the distal end of the end cap is considered to be the terminal end of the optical fiber. In the implementation of FIGS. 11A and 11B, for example, the end of the optical fiber 611 may comprise an end cap that is arranged to end emit disinfecting light toward the first refractive optical surface 615. According to some implementations an index matching material, such as a gel or adhesive, is positioned in a gap that separates the end 659 of the end cap 654 from the end wall of lumen/recess 612. In such an implementation, the index matching material is selected to have a refractive index between that of the end cap medium 656 and that of the first refractive optical surface 615 formed in or located on the end wall of lumen 612.

Figure 16:
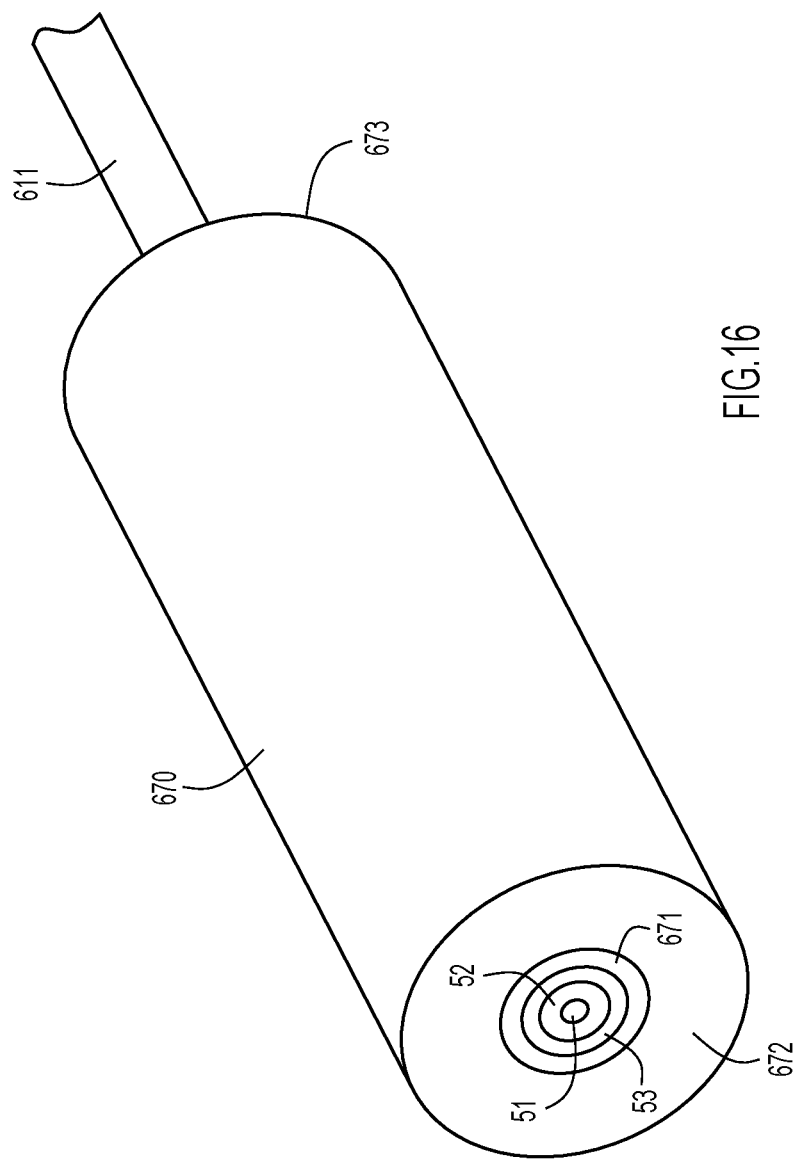
FIG. 16 is a perspective view of an end emitting fiber housed within the lumen of a rigid structure.

According to some implementations, at least a portion of the distal end section of the optical fiber 611 that resides inside the lumen/recess 612 is encased within a rigid structure. The rigid structure may be, for example, a rigid cylindrical body 670 having a through lumen 671 in which the distal end section of the optical fiber 611 resides as illustrated in FIG. 16. According to some implementations the distal end section of the optical fiber 611 is affixed inside the lumen 671 of the rigid body 670 by use of an adhesive, such as an epoxy. According to one implementation the through lumen 671 of the rigid body 670 has an inner diameter that is slightly larger than the outer diameter of the optical fiber 611 so as to permit the distal end section of the optical fiber to be easily inserted into the lumen 671. As discussed above, the distal end section of the optical fiber 611 may be affixed inside the lumen 271 by the use of an adhesive.

According to one implementation the device is constructed by introducing the fiber 611 into and through the lumen 671 so that the distal end 613 of the fiber 611 resides flush or substantially flush with the distal end 672 of the rigid body 670, resides slightly distal to the distal end 672 of the rigid body 670, or resides slightly proximal to the distal end 672 inside the lumen 671 of the rigid body 670. The distal end section of the fiber 611 is then affixed inside the lumen 271 as discussed above. This can be followed by a grinding and/or buffing of the fiber 611 and/or distal end face 672 of the rigid body 670 in order to cause the end 613 of the optical fiber 611 to be flush with the distal end face 672 of the rigid body 670 as shown in FIG. 16.

Figure 19B:
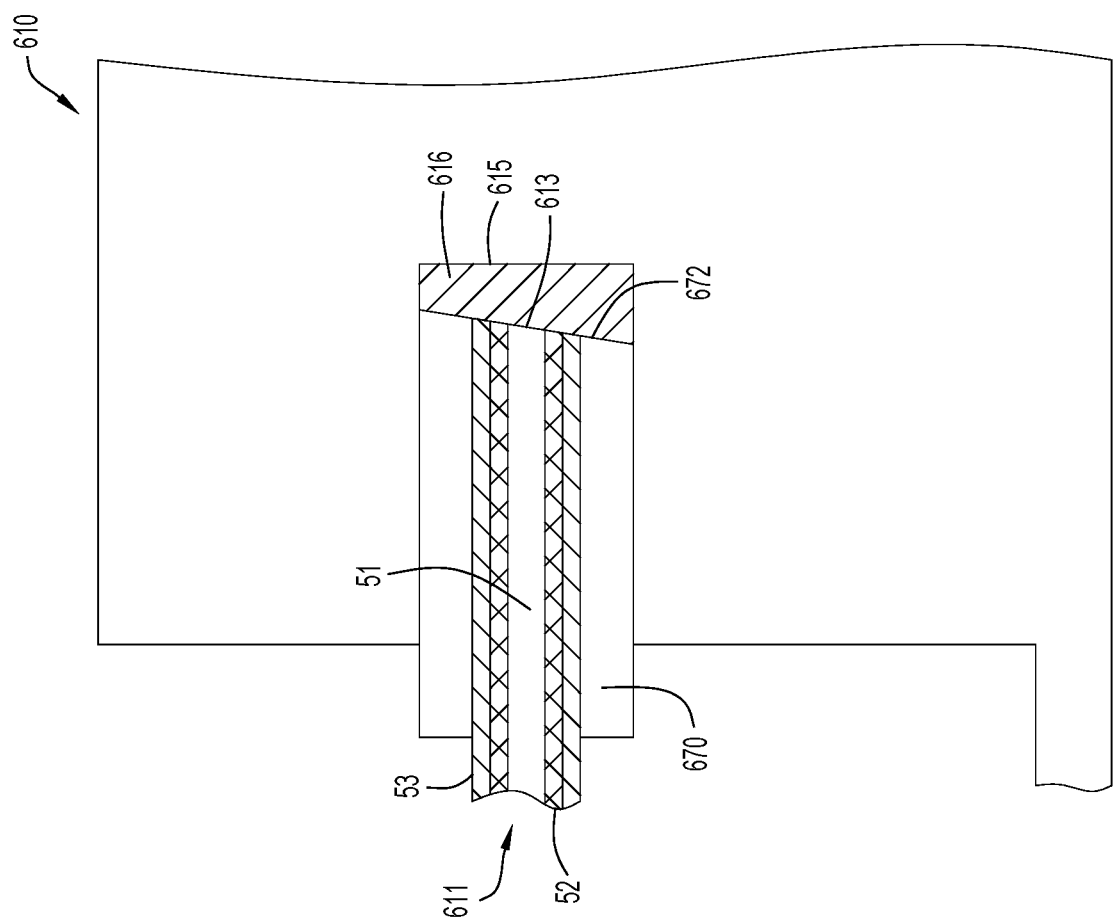
FIG. 19B illustrates an optical fiber assembled in an optical body according to another implementation.

FIG. 19A shows a cross-sectional side view of an optical body 610 wherein the distal end section of the optical fiber 611 is supported and affixed inside a rigid structure 670, which is in turn supported and affixed inside the optical body opening/recess 612. An index matching gel or adhesive 616 is positioned between the end of the optical fiber core 51 and the first refractive optical surface 615 and has an index of refraction between that of the core 51 and the optical surface 615. As shown in FIG. 19B, according to some implementations the distal end face 672 of the rigid body 670 and the distal end 613 of the optical fiber 611 are angled to prevent light emitted from the optical fiber to be back reflected into the core 51. The angle of inclination of the tilt may be between about 2 to about 10 degrees, and preferably between about 4 to about 8 degrees in relation to the longitudinal axis of the optical fiber. According to some implementations the optical fiber 611 is held inside the lumen 671 of the rigid structure by an index matching material that is the same or similar to the index matching gel or adhesive 616 positioned between the end of the optical fiber core 51 and the first refractive optical surface 615.

Figure 20B:
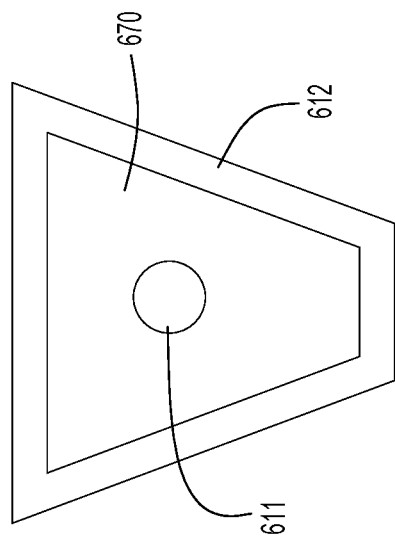
FIGS. 20A and 20B illustrate exemplary key configurations of a rigid structure that houses a distal end section of an optical fiber and the opening or recess of an optical body.
Figure 20A:
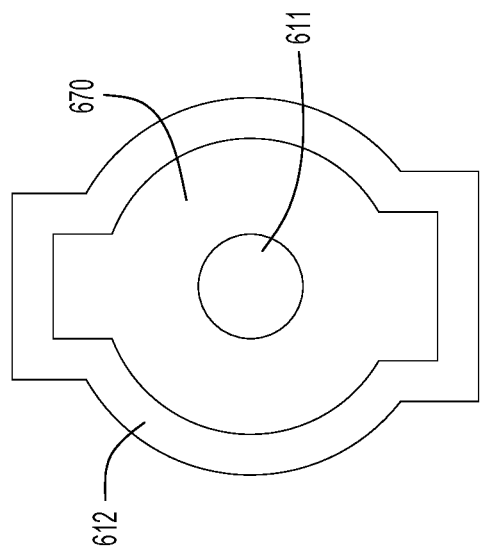

It is important to note that the external shape of the rigid structure 670 may take on any of a variety of shapes. According to some implementations the external shape of the rigid structure 670 and the internal shape of the opening/recess 612 of the optical body 610 are designed to be keyed to one another. In this way, the rigid structure 670 is required to be oriented inside the opening/recess 612 in a particular way. For example, in the implementation of FIG. 19B the rigid structure 670 is keyed in the opening/recess 612 of the optical body 610 to cause the angle of inclination of the end face 672 of the rigid structure to be oriented slanting downward as shown in the figure. The rigid structure 670 may also be keyed inside the opening/recess 612 to simply prohibit its rotation therein. FIGS. 20A and 20B illustrate two example key configurations.

The rigid structure 670 may comprise any of a variety of materials, such as metals, ceramics, plastics, etc. The use of a rigid structure provides a number of advantages. First, it inhibits breakage at the distal end section of the optical fiber during an assembling of the optical fiber with the optical body 610 as a result of the distal end section of the optical fiber being protected inside the rigid structure to prevent or inhibit the fiber from being bent. Second, it provides a more consistent placement of the optical fiber 611 inside opening/recess 612 of the optical body 610 to allow the distal end 613 of the optical fiber 611 to be properly aligned with the first refractive optical surface 215. Third, because the distal end 613 of the optical fiber 611 is firmly held inside the rigid structure 670, the distal end of the fiber may be more easily polished to provide better optical coupling in the form of less light loss.

According to some implementations the rigid structure 670 is made of a thermally conductive material that is capable of enhancing the dissipation of heat generated at and/or adjacent the distal end of the optical fiber 611. In the context of the present disclosure a thermally conductive material is a material that has a greater thermal conductivity and/or thermal mass than that of the cladding 52 or buffer layer 53 of the optical fiber. A material of greater thermal mass is considered herein to be a material that has a higher specific heat capacity and density than that of the cladding 52 or buffer layer 53 of the optical fiber. The material may be, for example, stainless steel.

As shown in FIGS. 19A and 19B, according to some implementations a portion of the rigid structure 670 protrudes proximally from the opening/recess 612 of the optical body 610. According to other implementations the proximal end 673 of the rigid structure 670 is flush with a rear face 676 of the optical body 610. According to other implementations the proximal end 673 of the rigid structure 670 resides inside the opening/recess 612 of the optical body 610.

As shown in FIG. 19A, according to some implementations the proximal end section of the rigid structure 670 comprises radially extending fins 675 that increase the surface area through which heat may be dissipated from the rigid structure 670.

Heat is typically generated at locations where light loss occurs, such as the interface of the end of the optical fiber core 51 with the index matching material (e.g. gel or adhesive) 616 and at the interface of the index matching material 616 and the first refractive optical surface 615. As illustrated in FIGS. 19A and 19B, at least the distal end face 672 of the rigid structure 670 is in thermal contact with index matching material 616. The rigid structure 670 is also thermally coupled to the first refractive surface 615 via the index matching material 616.

Figure 21A:
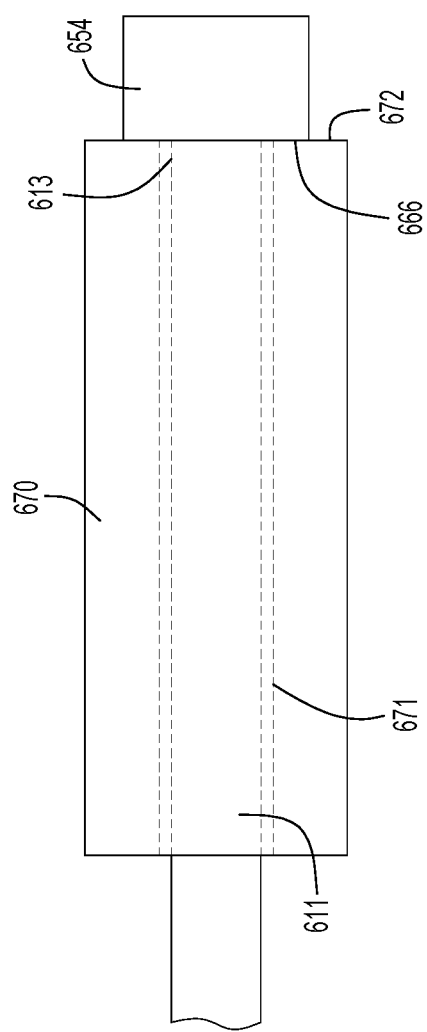

As discussed above, according to some implementations the optical fiber 611 is equipped with an end cap to reduce the power density of the light delivered to the first refractive optical surface 615. FIG. 21A illustrates an implementation wherein an end cap 654 is used in conjunction with a rigid structure 670. FIG. 21B shows the assembled optical fiber 611, end cap 654 and rigid structure 670 affixed to the optical body 610.

According to one implementation the distal end 613 of the optical fiber 611 is affixed to and optically coupled with the end cap 654 in the manner described above. Thereafter, the distal end section of the optical fiber is positioned in the lumen 671 of the rigid structure 670 with a proximal face 666 of the end cap 654 in abutment with the distal face 672 of the rigid structure 670 as shown in FIG. 21A. The optical fiber 611 may be back loaded into the lumen 671 of the rigid structure 670 by introducing the proximal end of the optical fiber into the distal opening of the lumen 671 and proximally advancing the optical fiber until to the end cap 654 abuts the distal end face 672 of the rigid structure 670. According to other implementations the rigid structure 670 is provided with a slit or gap that runs the length of the rigid structure to permit the optical fiber 611 to be side loaded into the lumen 671 of the rigid structure through the slit or gap. Attachment of the optical fiber 611 to the rigid structure is accomplished by use of an adhesive that is introduced into the lumen 671 of the rigid structure 670 after placement of the optical fiber inside the lumen 671. Attachment can also occur by affixing the end cap 654 to the distal end face 672 of the rigid structure 670 by use of an adhesive. In either case, according to some implementations the adhesive possesses an index of refraction between that of the optical fiber core 51 and the first refractive optical surface 615.

Figure 22A:
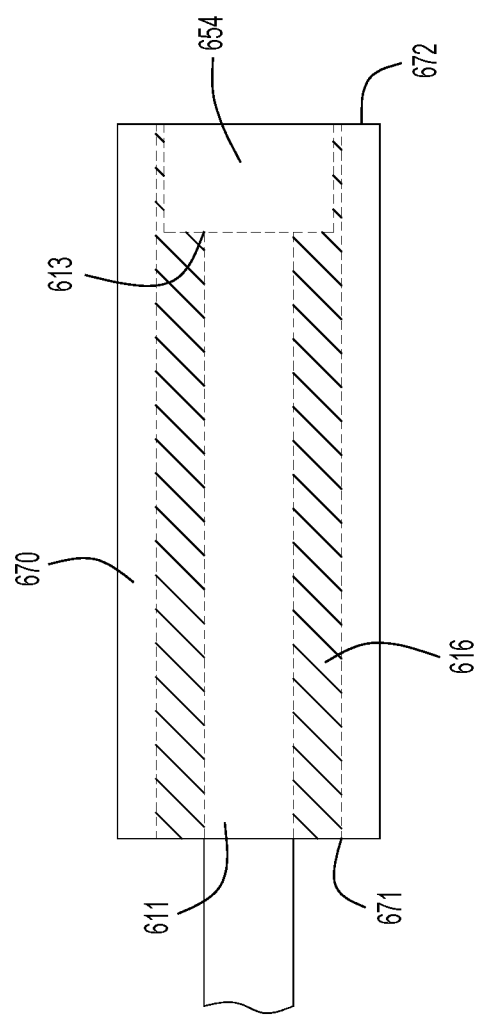
FIGS. 22A and 22B illustrate optical fiber assemblies according to other implementations that includes a rigid structure and an end cap.
Figure 22B:
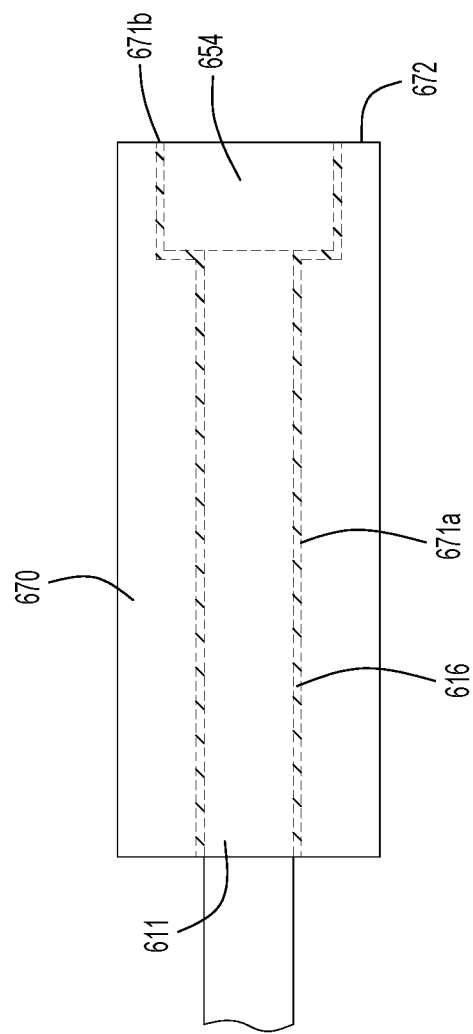

According to some implementations the distal end section of the optical fiber 611 is constructed such that the end cap fully or at least partially resides inside the rigid structure 670 as shown in FIGS. 22A and 22B. According to some implementations the internal through lumen 671 of the rigid structure 670 has a uniform diameter as shown in FIG. 22A. According to such an implementation the outer diameter of the end cap 654 is sized to be slightly less than the inner diameter of the lumen 671 so that the end cap can be easily introduced into and substantially centrically located inside the lumen 671. According to one implementation attachment of the optical fiber 611 to the rigid structure 670 is achieved by introducing an adhesive into the lumen 671. In the implementation shown in FIG. 22A the distal end of the end cap 654 is arranged flush with the distal end face 672 of the rigid structure 670. According to other implementations the distal end of the end cap 654 protrudes distal to the distal end face 672. An advantage of locating at least a portion of the end cap inside the lumen of the rigid structure is that it allows the end cap to be centrically self-aligned inside the central through lumen 671. This assist in establishing a consistent optical path between the outlet of the end cap 654 and the first refractive optical surface 615.

According to some implementations the internal through lumen 671 of the rigid structure comprises a proximal section 671a with a first diameter and a distal section 671b with a second diameter, the second diameter being greater than the first diameter as shown in FIG. 22B. According to such implementations the end cap 654 resides at least partially in the distal section 671b of the lumen and the distal end portion of the optical fiber 611 attached to the end cap resides inside in the proximal end section 671 of the lumen. Like the implementation of FIG. 22A, the distal end of the end cap 654 may be arranged flush with the distal end face 672 of the rigid structure 670, or may protrude a distance distal to the distal end face 672. In regard to each of the implementations of FIGS. 22A and 22B, according to some implementations the rigid structure 670 comprises a longitudinal slit or gap that opens into the inner through lumen 671 to permit the optical fiber 611 to be side loaded into the lumen 671.

In regard to each of the implementations of FIGS. 21A, 21B, 22A and 22B, the rigid structure 670 may be keyed with the recess or opening 612 of the optical body 610 as discussed above in conjunction with the implementations of FIGS. 20A and 20B. The combination of these features assists in providing a consistent alignment between the end of the optical fiber (or end cap) and the first refractive optical surface 615.

According to some implementations the rigid structure 670 is inflexible. However, in the context of the present application the term "rigid structure" can comprise any structure that is more rigid than the optical fiber it houses. Thus, according to some implementations the rigid structure is capable of being bent/flexed but to a lesser degree than that of the optical fiber it houses.

According to any of the implementations disclosed herein that comprise a rigid structure 670, the rigid structure may include at its proximal end 673, or anywhere along its length, one or more radial protrusions 677 that are configured to abut a side 676 of the optical body 610 to limit forward movement of the rigid structure into the opening or recess 612. See FIG. 23. In this manner, the distal end of the optical fiber 611, or the distal end of an end cap 654 attached thereto, may be maintained a set distance proximal to the first refractive optical surface 615. The radial protrusions may comprise two or more spaced apart radially extending tabs or may comprise a continuous protrusion (e.g. annular flange) that circumscribes the rigid structure 670.

Figure 24:
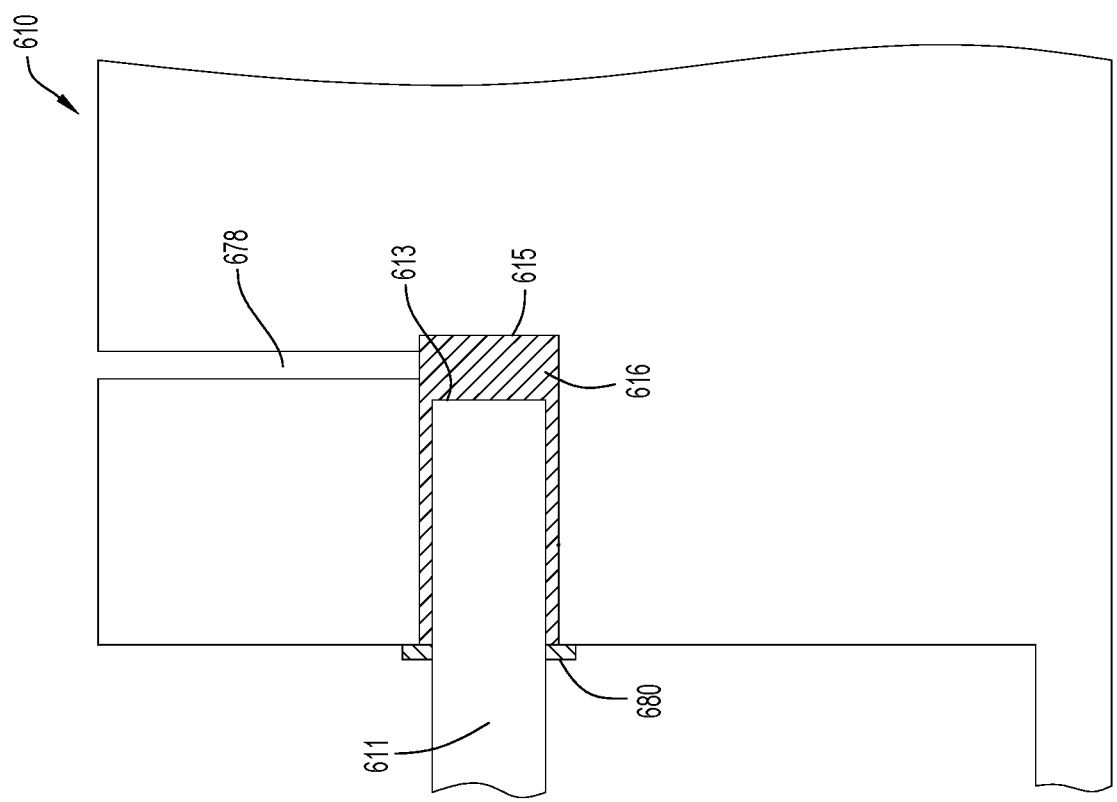
FIG. 24 shows an optical fiber according to one implementation that includes one or more radially extending features to limit the longitudinal advancement of the optical fiber into the opening or recess of an optical body.

As shown in FIG. 24, in implementations that do not comprise a rigid structure 670, the outer surface of the optical fiber 611 may be fitted with a ring 680, or other structure, that protrudes radially from the outer surface of the optical fiber. The ring 680, or other radially protruding structure, is arranged on the optical fiber 611 to limit its advancement into the opening or recess 612 so that the distal end 613 of the optical fiber may be maintained a set distance proximal to the first refractive optical surface 615.

Figure 25A:
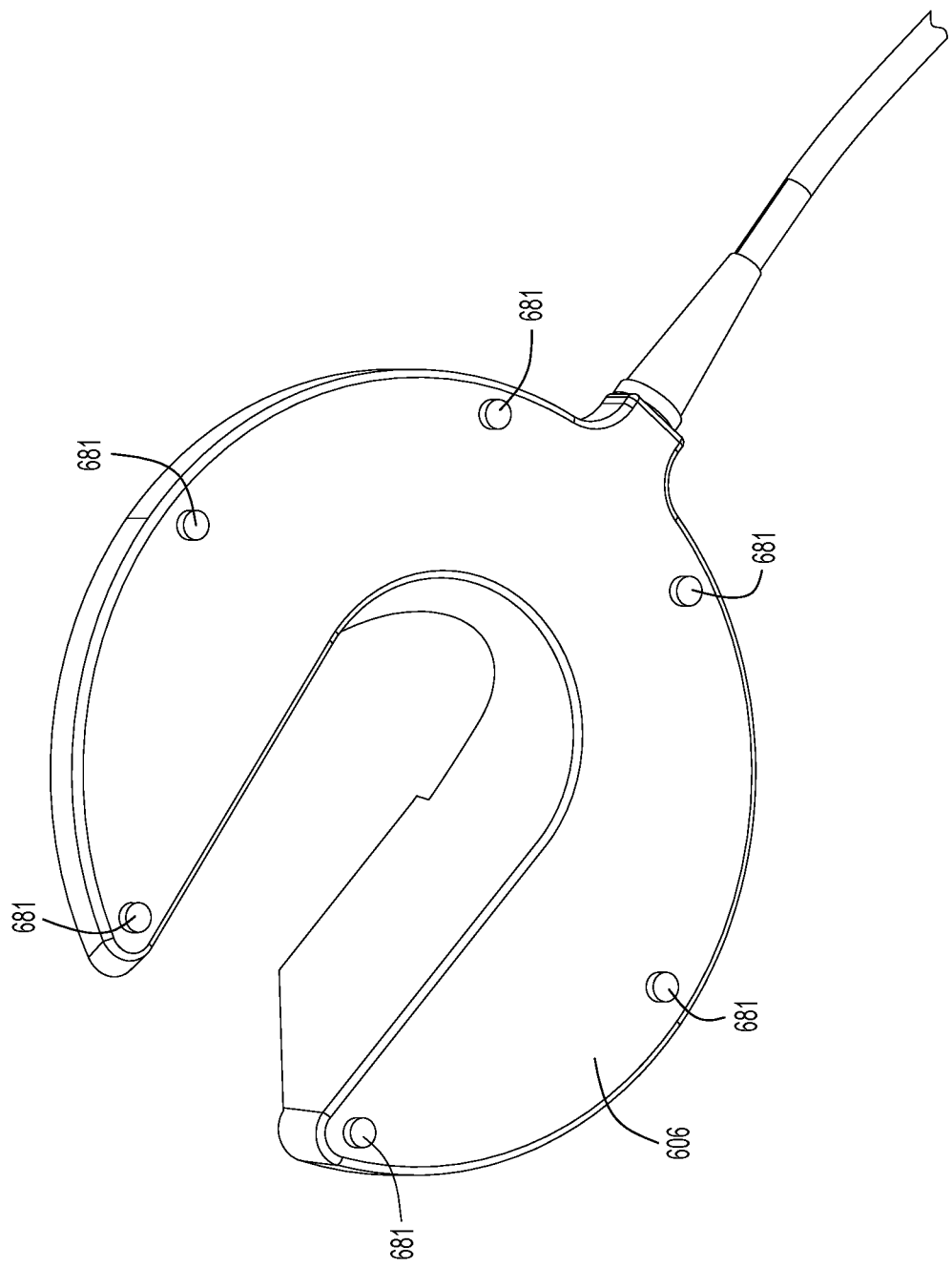
FIGS. 25A and 25B illustrate a bottom of a light disinfecting device having one or more footings.
Figure 25B:
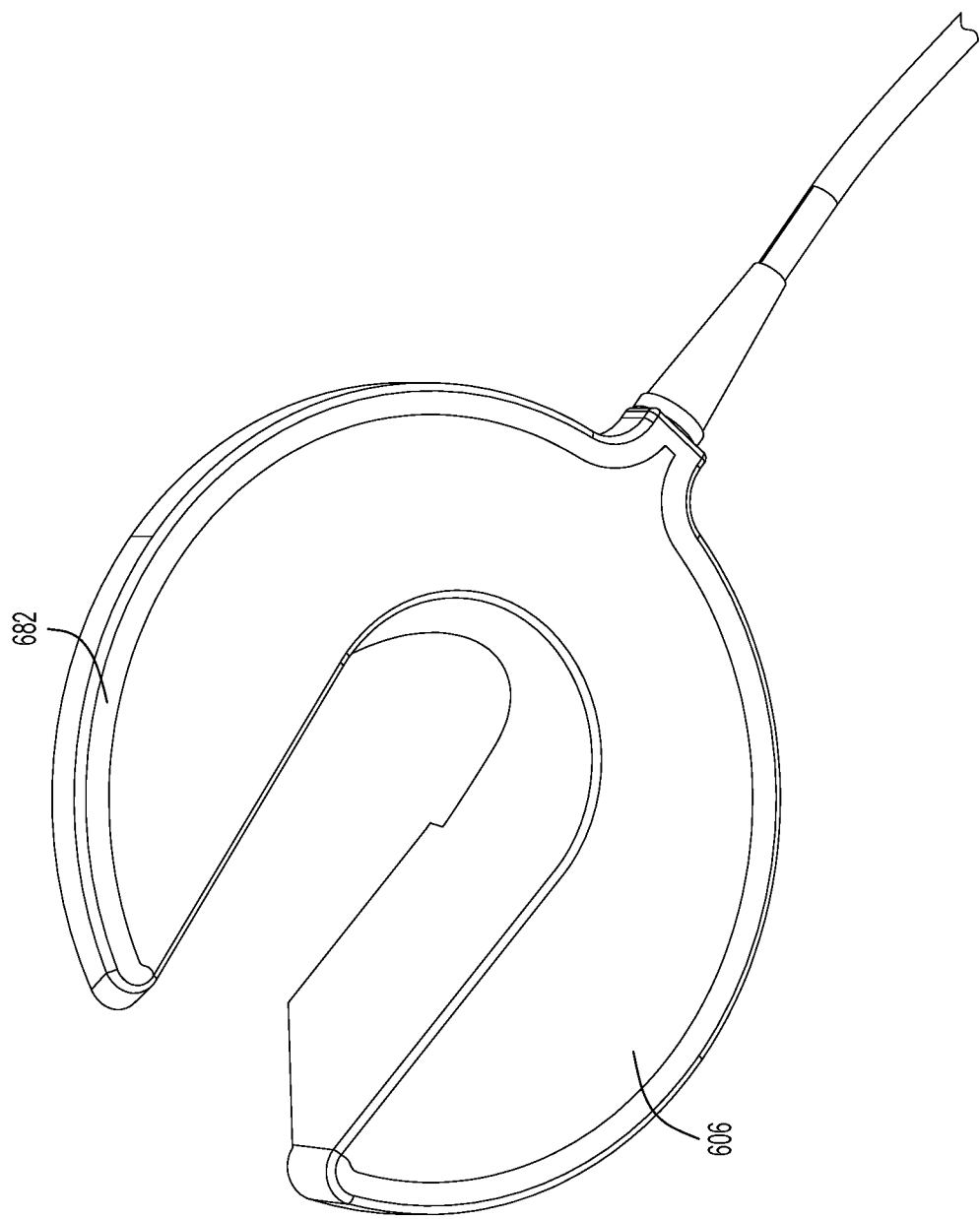

According to some implementations the disinfecting target area is designated to be located a distance below the bottom surface of the light disinfecting device 600 like, for example, that shown in FIG. 12. To facilitate such an arrangement, according to some implementations the base 601 of the light disinfecting device 600 is equipped with a footing in the form of protruding spaced apart feet 681 as shown in FIG. 25A or in the form of a continuous bottom protruding ring 682 as shown in FIG. 25B. In each case, the footing is disposed about the outer periphery of the bottom surface 606 of the base 601 so that it does not substantially interfere with the transmission of disinfecting light between the bottom 608 of the optical body 610 and the disinfecting target area. According to some implementations the footing has a height of between about 1 to about 25 millimeters.

Figure 26:
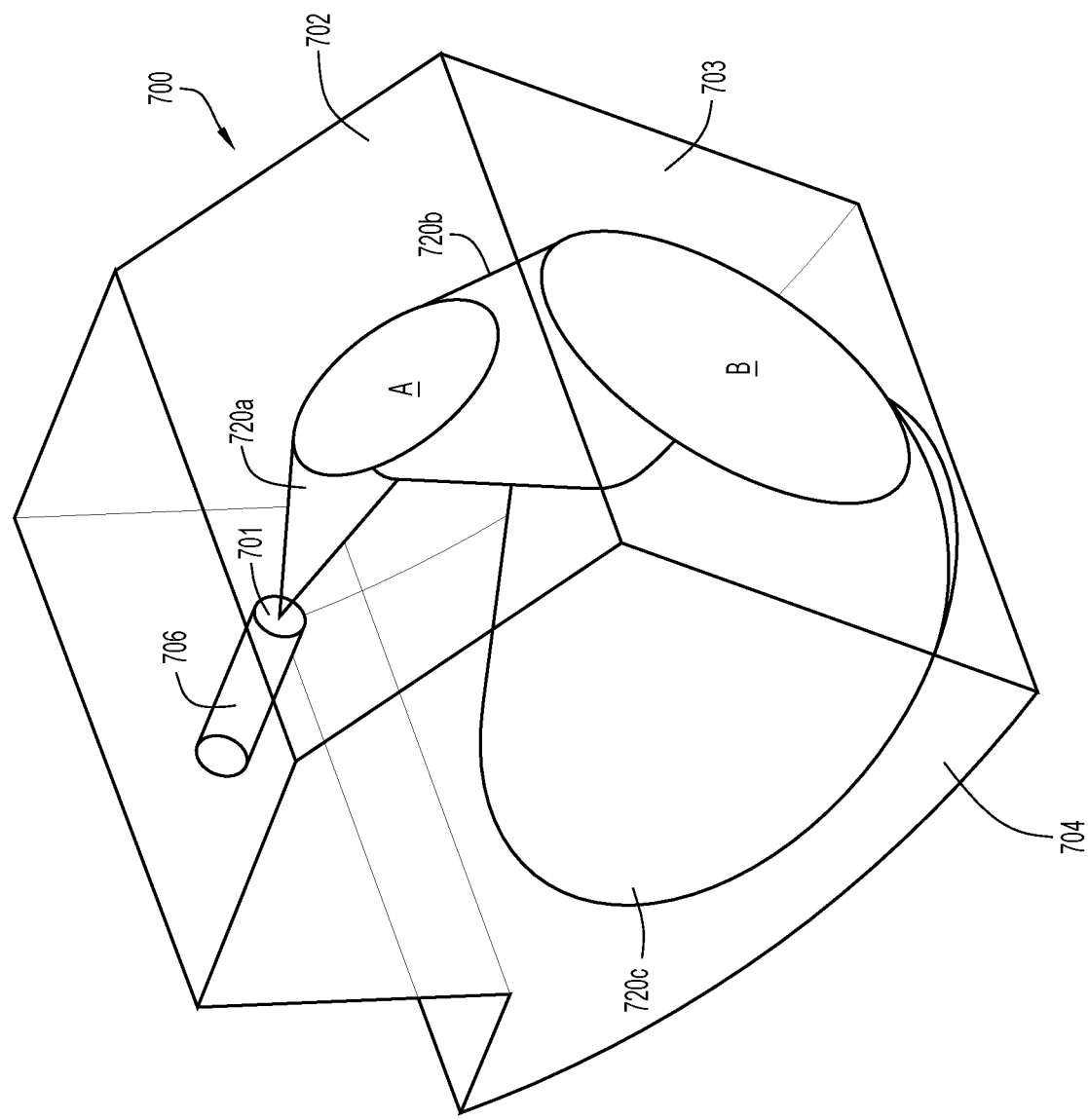
FIG. 26 is an isometric view of an optical body having two total internal reflection optical surfaces according to one implementation.

FIG. 26 illustrates an optical body 700 according to another implementation that includes a plurality of refractive optical surfaces and a plurality of total internal reflection (TIR) optical surfaces. FIG. 26 shows the trajectory of light through the optical body 700.

In the implementation of FIG. 26 the optical body 700 includes a first refractive optical surface 701, a first TIR optical surface 702, a second TIR optical surface 703 and a second refractive optical surface 704. According to some implementations the outer surfaces of the optical body 700 are bounded by air. The optical body 700 also includes an opening 706 for receiving the distal end section of an optical fiber (not shown). The description above related to the optical fiber 611 and the manner in which its distal end section is supported inside the opening/recess 612 of the optical body 610 is equally applicable to all optical bodies disclosed and contemplated herein. As previously discussed, light leaving the distal end of the optical fiber may first pass through an index matching gel or adhesive position that is located between the distal end of the optical fiber and the first refractive optical surface 701. In the optical body 700 of FIG. 26, when light is delivered to an optical fiber who's distal end is positioned in the opening 706, a light beam 920a exiting the first refractive optical surface 701 travels in a forward direction and impinges on the first TIR optical surface 702 at location A. The reflected light beam 720b from location A is directed downward and forward so that it impinges on the second TIR optical surface 703 at location B. The reflected light beam 720c from location B is directed downward and rearward so that it impinges on and is refracted through the second refractive optical surface 704. In the implementation of FIG. 26, the second refractive optical surface 704 forms the bottom of the optical body 700.

The use of multiple TIR optical surfaces in an optical body allows the light beam passing through the optical body to be manipulated in ways not possible when a single TIR optical surface is used. For example, as seen in FIG. 26, and more clearly in FIG. 27, the light beam may be manipulated to impinge on a target treatment site that is located rearward of the distal end 713 of the optical fiber 710. An optical body of a more compact size is also achievable without sacrificing the size of the resultant light beam exiting the light disinfecting device.

Figure 27:
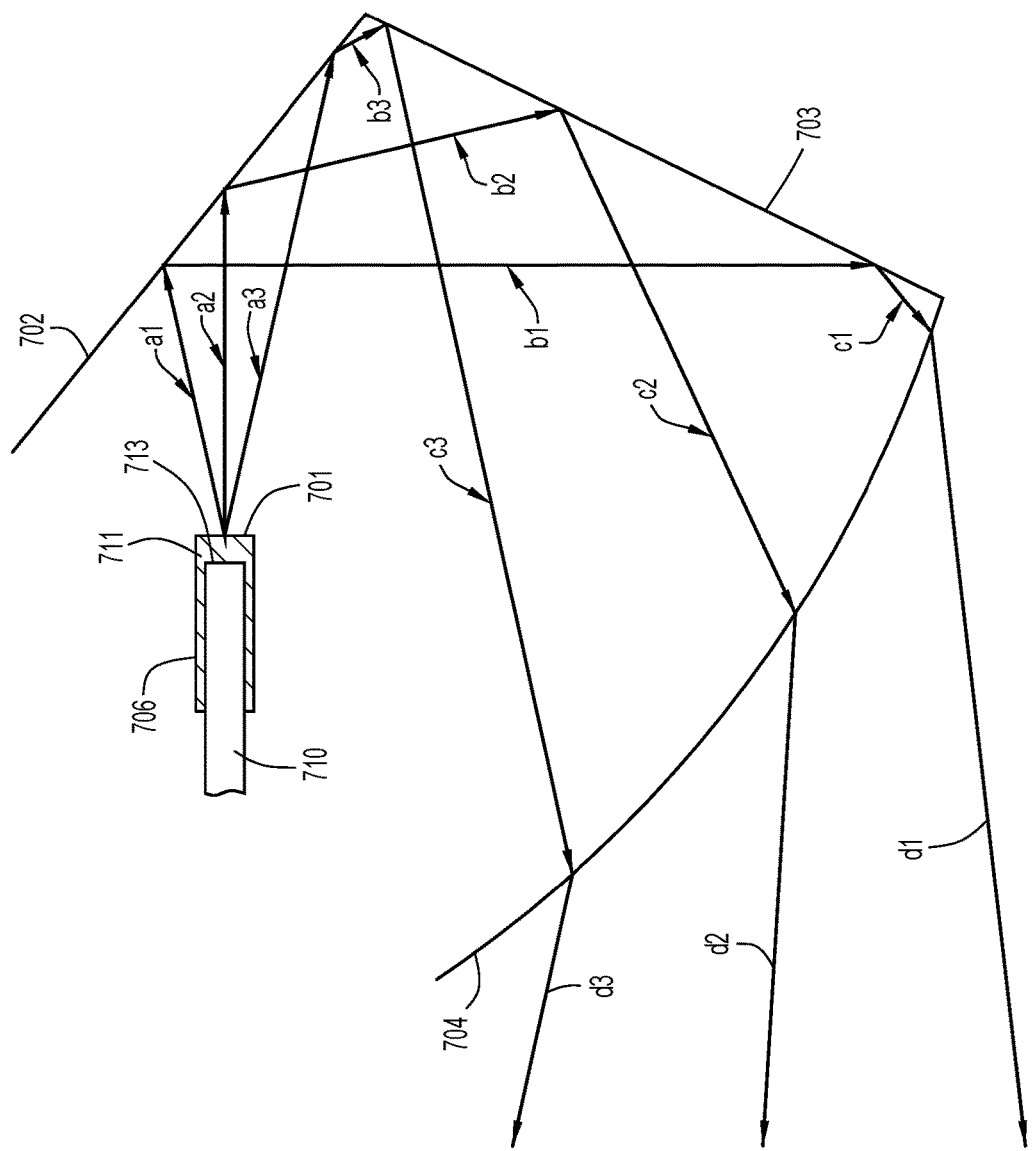
FIG. 27 illustrates a cross-sectional schematic side view an implementation of the optical body of FIG. 26.

FIG. 27 is a schematic diagram of the optical body 700 of FIG. 26. Light beam 920a is represented by light rays a1, a2 and a3. Light beam 920b is represented by light rays b1, b2 and b3. Light beam 920c is represented by light rays c1, c2 and c3. Light rays a1, a3, b1, b3, c1 and c3 represent the peripheral boundary of the respective light beams while light rays a2, b2 and c2 represent light rays centrically located in the respective light beams. According to one implementation the optical fiber 710 is positioned and held inside the optical body opening 706 by an index matching adhesive 711. In the implementation shown, when a light beam is emitted from the distal end 713 of the optical fiber, the light beam first passes through the index matching adhesive 711 before it is refracted through the first refractive optical surface 701. Light is thereafter dispersed inside the optical body 700 in a manner consistent to what is illustrated in FIG. 27.

As explained above, total internal reflection is the phenomenon which occurs when a propagated wave strikes a medium boundary at an angle larger than a particular critical angle normal to the incident surface. If the refractive index is lower on the opposing side of the boundary and the incident angle is greater than the critical angle, the wave cannot pass through and is entirely internally reflected. The critical angle is the angle of incidence above which the total internal reflection occurs. In the implementation of FIGS. 26 and 27 the distal end 713 of the optical fiber 710, the first refractive optical surface 701, the first TIR optical surface 702 and the second TIR optical surface 703 are arranged with respect to one another in a manner that causes light rays a1-a3 and b1-b3 to impinge respectively on surfaces 702 and 703 at an incident angle that is greater than the critical angle so that light beam 720a is totally reflected at surface 702 and light beam 720b is totally reflected at surface 703.

In the implementation of FIGS. 26 and 27 the second refractive optical surface 704 is a curved concave surface that produces a refracted light beam represented by light rays d1-d3. As shown, optical surface 704 is shaped to cause an outward divergence of the light rays which results in a greater spread as discussed in more detail above. In a manner like that described above in conjunction with the description of optical bodies 610 and 620, one or more of the location, angular orientation, shape and curvature of the optical surfaces 701-704 may be manipulated to produce a desired disinfecting result in terms of irradiance and size.

According to some implementations a light disinfecting device may include a first optical body having a single TIR optical surface and a second optical body having a plurality of TIR optical surfaces (e.g. 2 TIR optical surfaces). For example, in the light disinfecting device 650 of FIG. 14 the rearward located optical bodies 651a and 651d may each comprise a single TIR optical surface and the forward located optical bodies 651b and 651c may each comprise multiple TIR optical surfaces, such as, for example, two TIR optical surfaces. In this manner light beams 654b and 654c exiting the optical bodies 651b and 651c, respectively, may be directed rearward of the distal end 745b and 745c of the optical fibers 653b and 653c.

Figure 28:
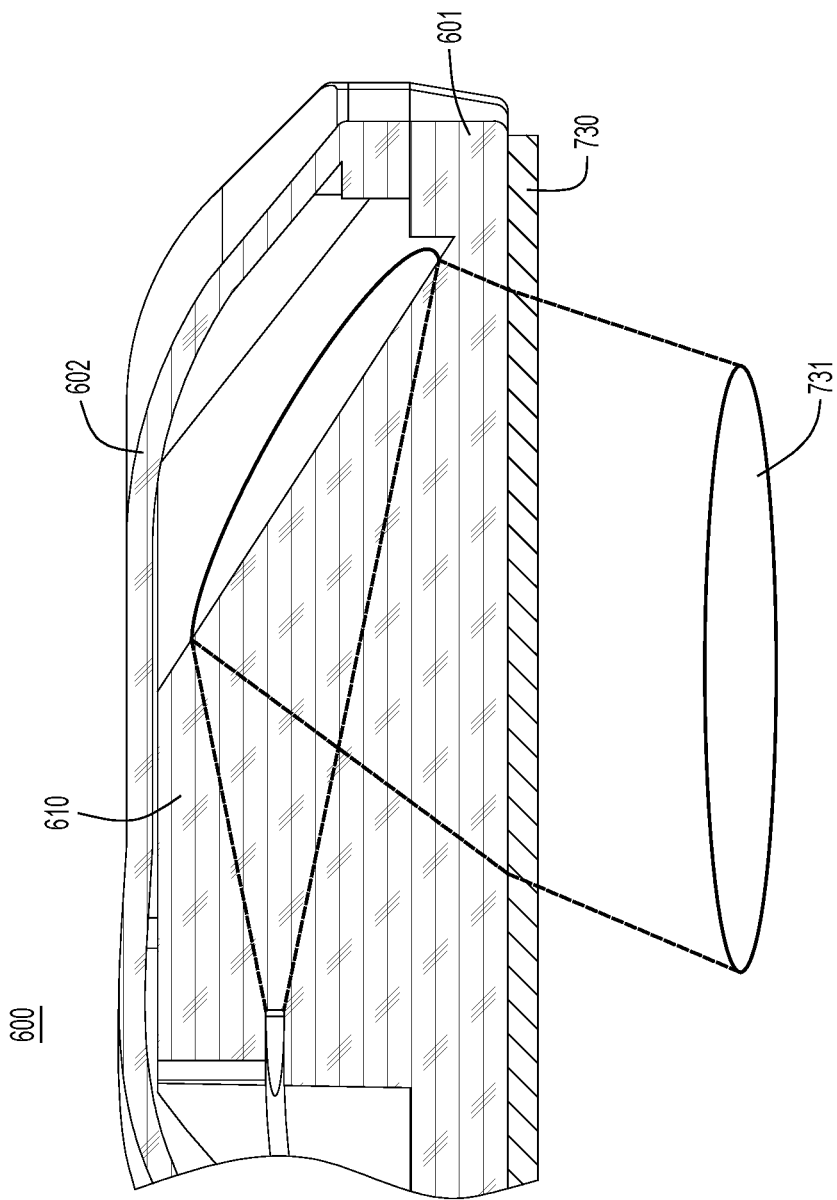
FIG. 28 illustrates a cross-sectional view of a light disinfecting device having a light diffuser fitted to the base of the device.

As shown in FIG. 28, which represents a modification to the implementation of FIG. 11A, the bottom surface 606 of the light disinfecting device 600 may be fitted with a light diffuser 730 in order to more evenly distribute the disinfecting light at the target disinfecting site 731. The use of a light diffuser may be applied to each of the light disinfecting devices disclosed or otherwise contemplated herein.

Figure 29B:
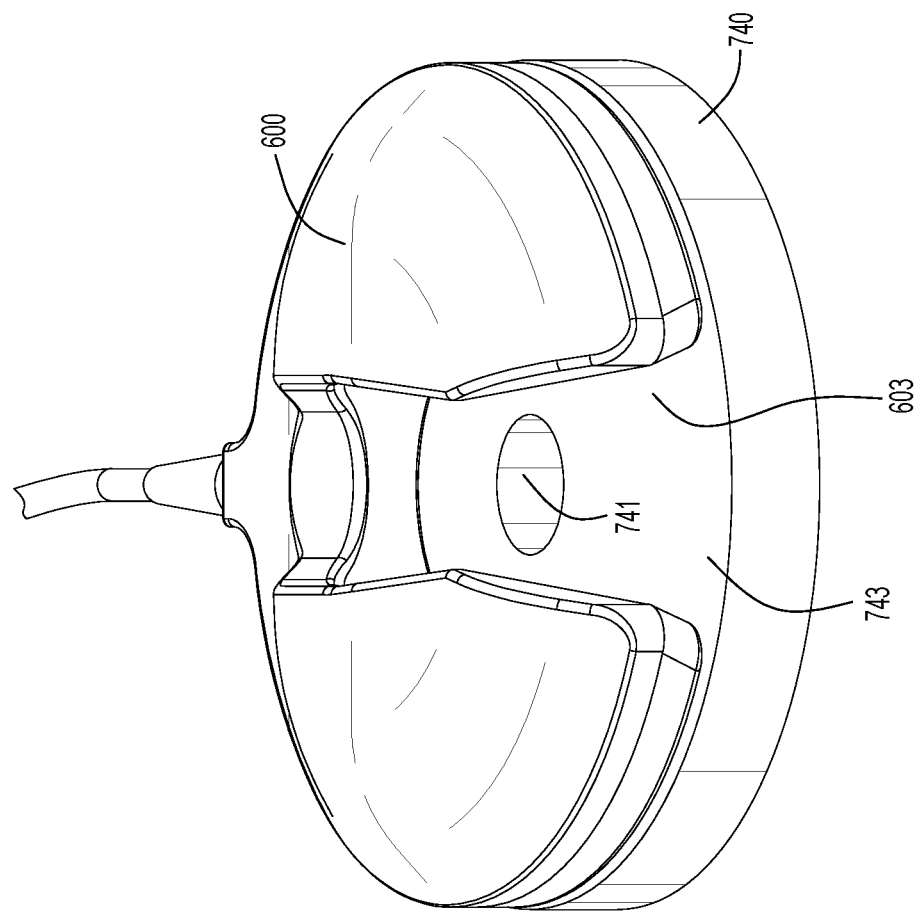
FIG. 29B illustrates the kit of FIG. 28A with the light disinfecting device positioned atop the absorbent pad.

FIG. 29A illustrates a kit comprising a light disinfecting device 600 according to any of the previously disclosed implementations and an absorbent pad 740. The absorbent pad 740 is made of one or more materials that are transparent, or at least partially translucent, to the disinfecting light emitted from the bottom surface 606 of the light disinfecting device 600. According to some implementations the absorbent pad 740 includes a central through opening 741 through which a main shaft of a CVC or other medical device may pass before being inserted into a patient. The absorbent pad 740 is configured to absorb bodily floods that may seep from the insertion site. The absorbent pad may comprise a slit 742 that extends from the central opening 741 to the outer periphery of the pad to facilitate an easy placement and removal of the pad from the treatment site. That is, a medical device inserted into a patient may be easily placed into or removed from the central through opening 741 of the absorbent pad 740 via a passage of the medical device through the slit 742. FIG. 29B shows the bottom surface 606 of the disinfecting device positioned on the top surface 743 of the absorbent pad 740 with the central through opening 741 residing below and being contiguous with the opening 603 of the light disinfecting device 600.

According to some implementations the bottom of the light disinfecting device comprises a cavity into which a top portion of the absorbent pad 740 resides in order to maintain the absorbent pad properly aligned with the bottom surface of the light disinfecting device. According to other implementations clips are other attachment features are provided to removably attach the absorbent pad 740 to the light disinfecting device 600.

As explained above, according to some implementations optical fibers are delivered to the light disinfecting device via an optical fiber umbilical cord 605. According to some implementations the proximal end of the umbilical cord 605 is equipped with an optical connector having a port associated with each of the optical fibers running through the umbilical cord. According to some implementations the proximal optical connector is configured to be directly connected to an LED or laser light source. According to another implementation that includes a CVC as shown in FIG. 3, light is delivered to the optical fiber umbilical cord 605 of the light disinfecting device 600 via the CVC optical fiber umbilical cord 500 and through the CVC hub 400 as shown in FIG. 30. In this manner, only a single optical connection to a light source is required, reducing the amount of hardware passing across the patient.

The length of the main shaft 200 of the CVC 100 that is inserted into a patient will vary depending on the particular medical procedure being performed and the actual site of insertion of the main shaft 200 into the patient. For this reason, according to some implementations the ratio of the length of the main shaft 200 extending distal to the hub 400 with that of the combined length of the light disinfecting device 600 and its associated fiber optic umbilical 605 (that portion of the fiber optic umbilical that extends distal to the hub 400) is between about 1.4 to about 2.8. According to some implementations the ratio of the length of the main shaft 200 extending distal to the hub 400 with that of the length of the fiber optic umbilical 605 (that portion of the fiber optic umbilical that extends between the distal end 400a of the hub 400 and the proximal end 600a of the light disinfecting device 600) is between about 1.4 to about 4.0. According to some implementations the longitudinal length of that portion of the main shaft 200 that extends distally to the hub is between about 20.0 to about 25.0 inches. According to some implementations the combined length of the light disinfecting device 600 and its associated fiber optic umbilical 605 (that portion of the fiber optic umbilical 605 that extends between the distal end 400a of the hub 400 and the proximal end 600a of the light disinfecting device 600) is between about 7.6 cm to about 15.2 cm. According to some implementations the length of the fiber optic umbilical 605 (that portion of the fiber optic umbilical that extends between the distal end 400a of the hub 400 and the proximal end 600a of the light disinfecting device 600) is between about 5.1 cm to about 15.2 cm. As a result of these lengths, the light disinfecting device 600 is capable of being placed at insertion sites of the main shaft 200 despite the actual length of the main shaft that is inserted into the patient. According to some implementations, the light disinfecting device 600 includes an open end 600b that permits the device to be slid across the insertion site of the main shaft 200 so that the device is more or less centrally located over the insertion site.

Vacuum-assisted drainage to remove blood or serous fluid from a wound or operation site is known. Vacuum-assisted drainage is a technique where a piece of foam with an open-cell structure is inserted into the wound, and a wound drain with lateral perforations is laid atop it. The entire area is then covered with a transparent adhesive membrane, which is firmly secured to the healthy skin around the wound margin. When the exposed end of the drain tube is connected to a vacuum source, fluid is drawn from the wound through the foam into a reservoir for subsequent disposal. The plastic membrane prevents the ingress of air and allows a partial vacuum to form within the wound, reducing its volume and facilitating the removal of fluid. The foam has a few important functions: it ensures that the entire surface area of the wound is uniformly exposed to this negative pressure effect, it prevents occlusion of the perforations in the drain by contact with the base or edges of the wound, and it eliminates the theoretical possibility of localized areas of high pressure and resultant tissue necrosis. The application of negative pressure removes edema fluid from the wound through suction. This results in increased blood flow to the wound (by causing the blood vessels to dilate) and greater cell proliferation. Another important benefit of fluid removal is the reduction in bacterial colonization of the wound, which decreases the risk of wound infections. Through these effects, vacuum-assisted closure enhances the formation of granulation tissue, an important factor in wound healing and closure.

FIG. 31 illustrates a conventional wound vacuum system 770 that includes a piece of foam 771 with an open-cell structure that is capable of being inserted into a wound. The distal end of a drainage tube 772 is affixed to the piece of foam 771 and, when in use, the proximal end of the drainage tube is coupled to a vacuum pump (not shown).

Figure 32B:
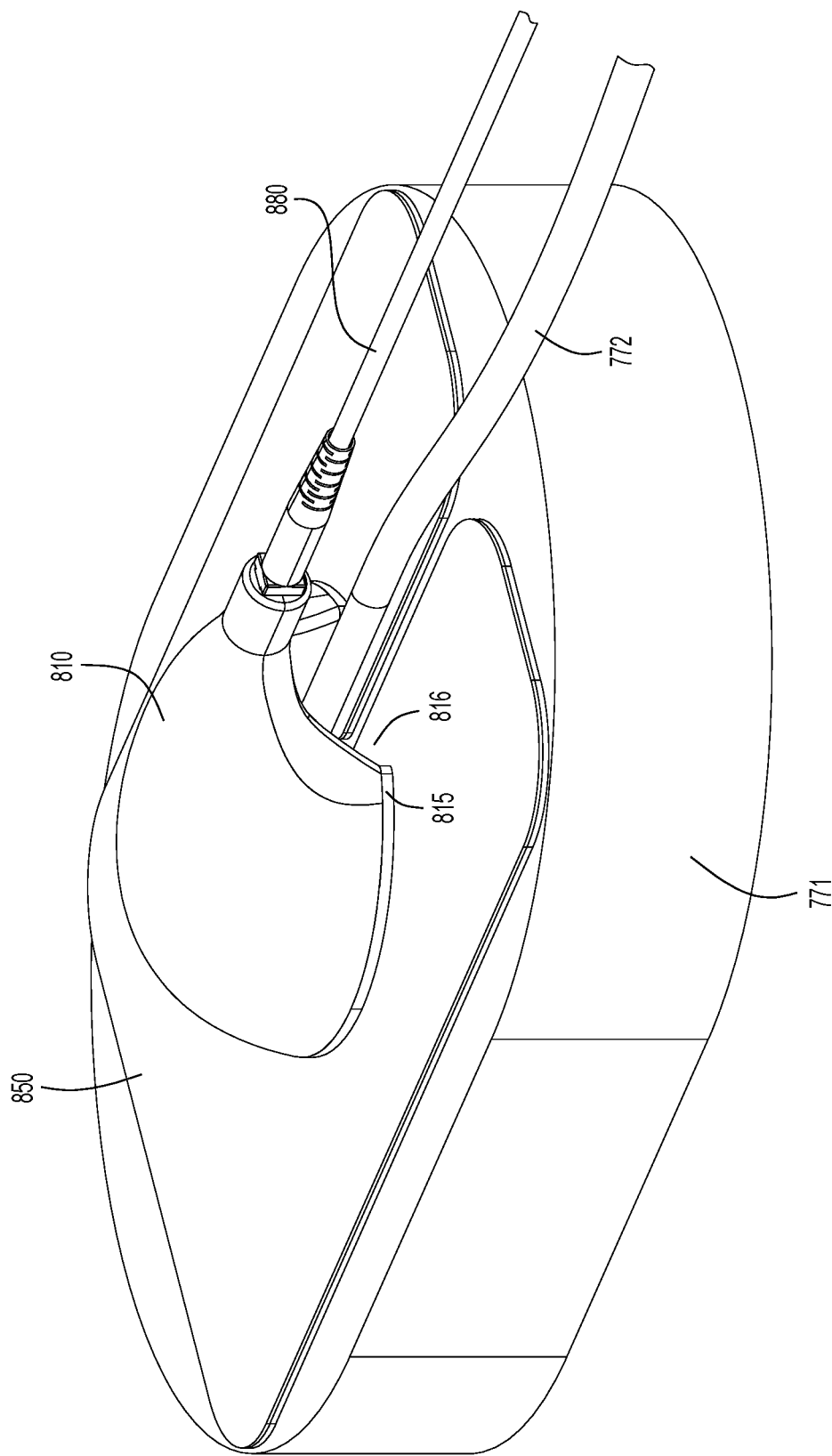

FIGS. 32A, 32B and 33 show a light disinfecting system 800 configured for use in disinfecting the wound site of a patient and/or a foam piece 770 inserted into a wound site of a patient and/or that portion of the drain tube 772 that is affixed to the foam piece. The light disinfecting system 800 includes a light disinfecting device 810 that may be similar in construction to the various light disinfecting devices hereinto disclosed. The light disinfecting system 800 further includes a light disinfecting pad 850 integrated with the light disinfecting device 810 to spatially increase the amount of area that can be disinfected. As will be discussed in more detail below, according to some implementations the light disinfecting device 810 produces disinfecting light at the wound site and/or within the foam piece 701 from light end emitted from one or more end emitting optical fibers, whereas the disinfecting pad 850 produces disinfecting light from one or more radially emitting optical fibers extending across portions of the disinfecting pad.

Figure 34:
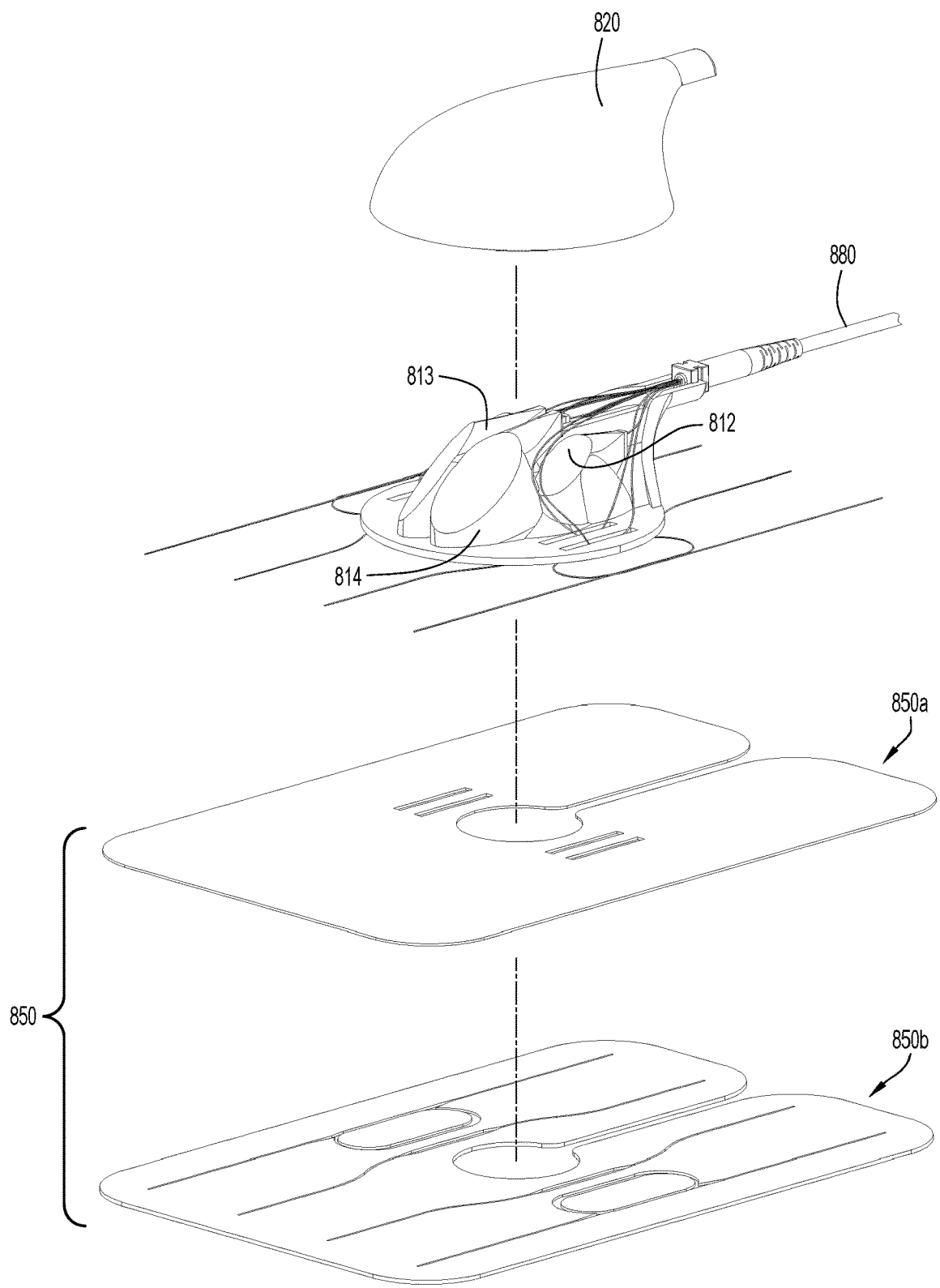
FIG. 34 is an exploded perspective view of a wound light disinfecting assembly according to one implementation.

FIG. 34 is an exploded perspective view of the light disinfecting system 800 of FIGS. 32 and 33 according to one implementation. In the implementation of FIG. 34, and of the figures that follow, the light disinfecting device 810 is shown to possess four optical bodies that are configured to cumulatively direct overlapping light beams to a wound site of a patient and/or into foam piece 701 of the wound vacuum system 770. It is appreciated that the light disinfecting device 810 may comprise a single optical body, two optical bodies, three optical bodies or greater than four optical bodies. According to some implementations the light disinfecting device 810 is provided with a cover 820 that is adapted to protect the optical bodies and associated optical fibers from external influences, such as dust, moister, touching, etc.

With continued reference to FIGS. 34 and 35A-C, the light disinfecting device 810 possesses first, second, third and fourth optical bodies 811, 812, 813 and 814, respectively. According to some implementations, each of the optical bodies 811-814 comprise a plurality of optical surfaces that are similarly configured and arranged to produce substantially the same type of light at the target disinfecting site in terms of irradiance and/or size. According to other implementations, one or more of the optical bodies 811-814 comprise optical surfaces that are not similarly configured and/or similarly arranged so as to produce different types of light at the target disinfecting site in terms of irradiance and/or size.

Figure 35B:
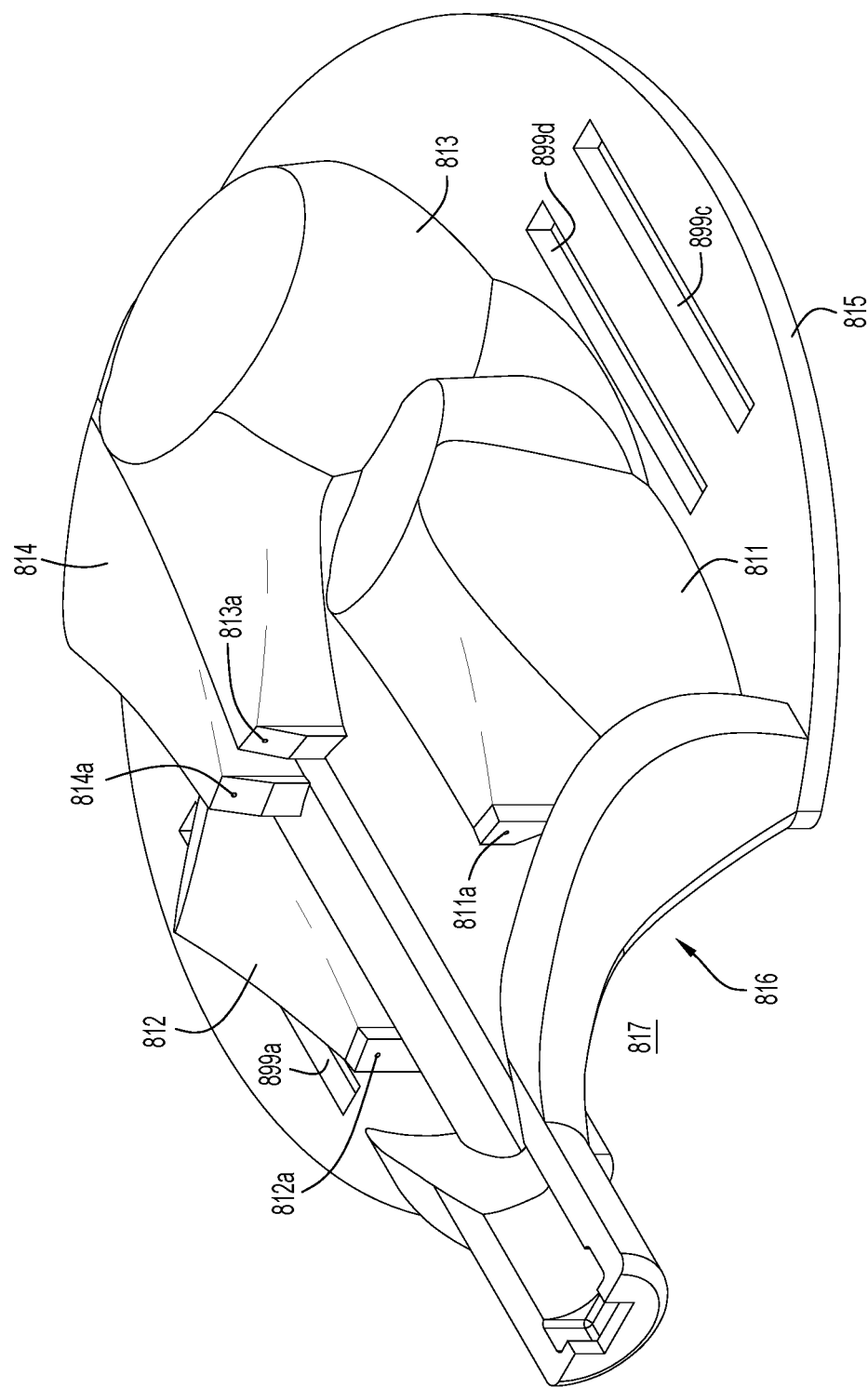
Figure 35C:
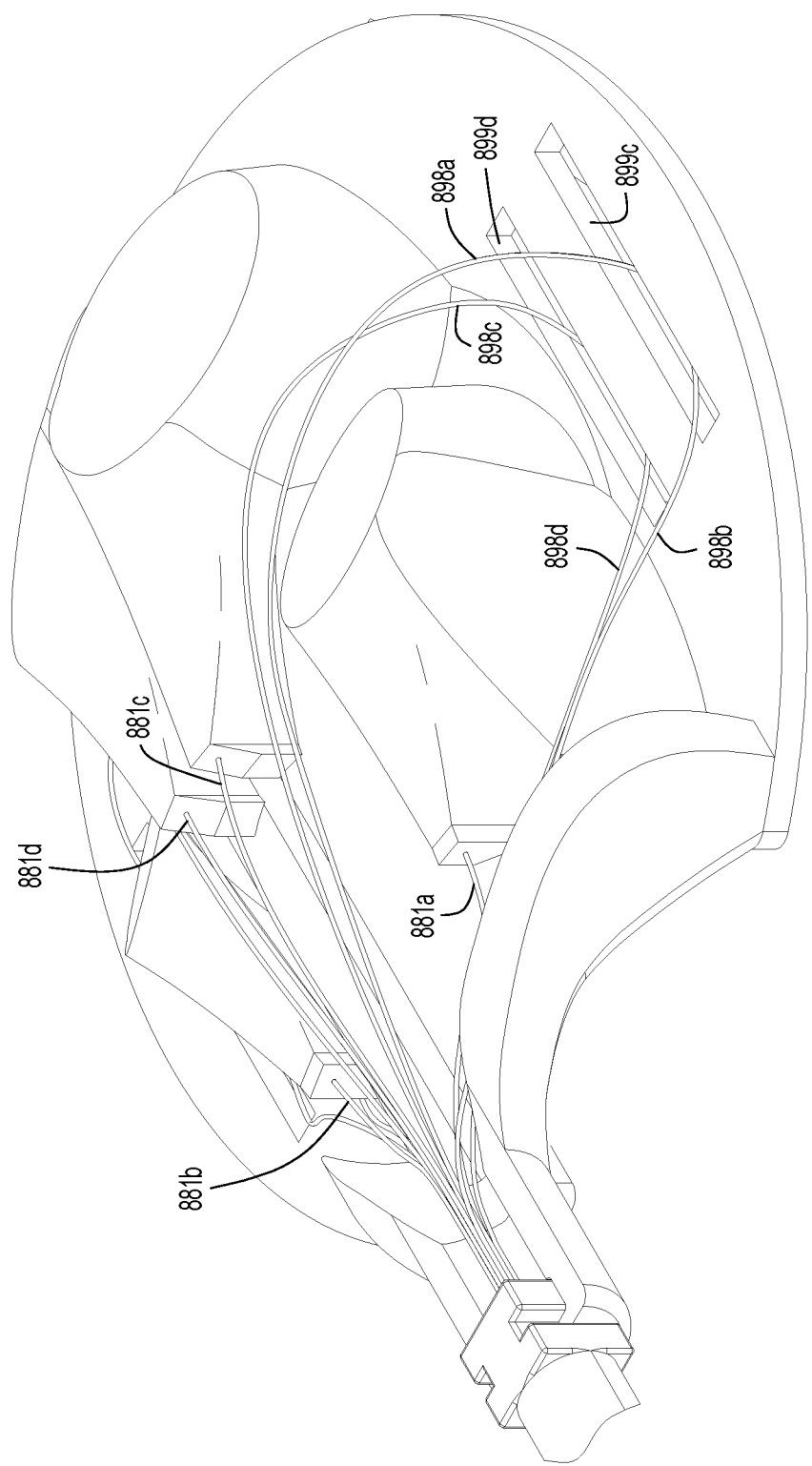

As best seen in FIGS. 35B and 35C, each of the optical bodies 811-814 respectively includes in a proximal end thereof an opening 811a-814a that is respectively configured to receive an optical fiber 811a-811d. According to some implementations the openings 811a-814a comprise recesses that each comprise a closed bottom end and an open top end located at a top surface of the respective optical body. The use of such recesses allows the optical fibers to be side loaded into the openings 811a-814a rather than being axially inserted into the openings 811a-814a. The manner in which each of the optical fibers 811a-811d is arranged inside the openings/recesses 811a-814a may be similar to or the same as any one of the arrangements described above in conjunction with optical fiber 611 and opening/recess 612 of optical body 610.

Like the implementations disclosed above in regard to the optical bodies 610 and 620, one or more of the optical fibers 811a-811d may comprise an end emitting optical fiber or a dual emitting optical fiber.

Like in the implementation of FIG. 14 discussed above, the rearward/proximally located optical bodies 811 and 812 may possess a single TIR optical surface, whereas the forward/distally located optical s bodies 813 and 814 may possess multiple TIR optical surfaces (e.g. two TIR optical surfaces).

As shown in FIG. 32B, the light disinfecting device 810 comprises an internal cavity 817 that extends to an opening 816 in the base 815 of the light disinfecting device. The cavity 817 and opening 816 are sized to accommodate a placement of the distal end portion of the drainage tube 772 inside the light disinfecting 810 and to facilitate a passage of the drainage tube 772 through the rearward/proximal end portion of the light disinfecting device. The distal end portion of the drainage tube 772 includes the part of the drainage tube that is affixed to the foam piece 771. According to some implementations each of the optical bodies of the light disinfecting device 810 is configured to deliver at least a portion of the light delivered through it to a target site that includes the location where the drainage tube 772 is affixed to the foam piece 771.

According to some implementations when the light disinfecting device 810 includes two or more optical bodies, the optical bodies are configured to deliver light in an overlapping manner to the target site. For example, according to some implementation the light disinfecting device 810 includes first and second optical bodies that are respectively configured to deliver first and second light beams to the target site in a manner that results in an overlapping of at least a portion of the first and second light beams at the target site. As a further example, with reference to the light disinfecting device 810 of FIGS. 35A and 35B which include first, second, third and fourth optical bodies 811-814, according to some implementations the first, second, third and fourth optical bodies 811-814 are respectively configured to deliver first, second, third and fourth light beams to the target site in a manner that results in an overlapping of at least a portion of two, three or all of the first, second, third and fourth light beams at the target site.

With continued reference to the light disinfecting device 810 of FIGS. 35A and 35B, according to some implementations the rearward/proximally positioned optical bodies 811 and 812 are spaced laterally apart from one another such that when the light disinfecting device 810 is positioned over the target site, the target site is located in the spaced between them.

As mentioned above, in order to deliver disinfecting light over a larger area of the foam piece 771, the light disinfecting system 800 further includes a light disinfecting pad 850 integrated with the light disinfecting device 810. According to some implementations the light disinfecting pad 850 comprises an upper element 850a and a lower element 850b having one or more radially emitting fibers interposed therebetween. According to some implementations the bottom element 850b includes one or more channels formed in its upper surface 851 where the one or more radially emitting optical fibers are housed. According to some implementations, upon the bottom surface 854 of the upper element 850 being positioned atop and affixed to the upper surface 851 of the lower element 850b, the one or more radially emitting fibers are fully encapsulated and protected inside the one or more channels.

According to some implementations the light disinfecting pad 850 includes a central through opening 845 through which the distal end section of the drainage tube 772 extends when the light disinfecting system 800 is positioned on the top surface 773 of the foam piece 771. A slotted through opening 846 that extends from the rearward/proximal end 847 of the pad 850 into the central through opening 845 is also provided to accommodate a passage of the drainage tube 772 into or out of the opening 845 during a placement and removal of the pad 850 from the top surface of the foam piece 771.

According to some implementations the bottom surface of the light disinfecting device 810 is attached to the top surface 853 of the upper element 850a.

Figure 38:
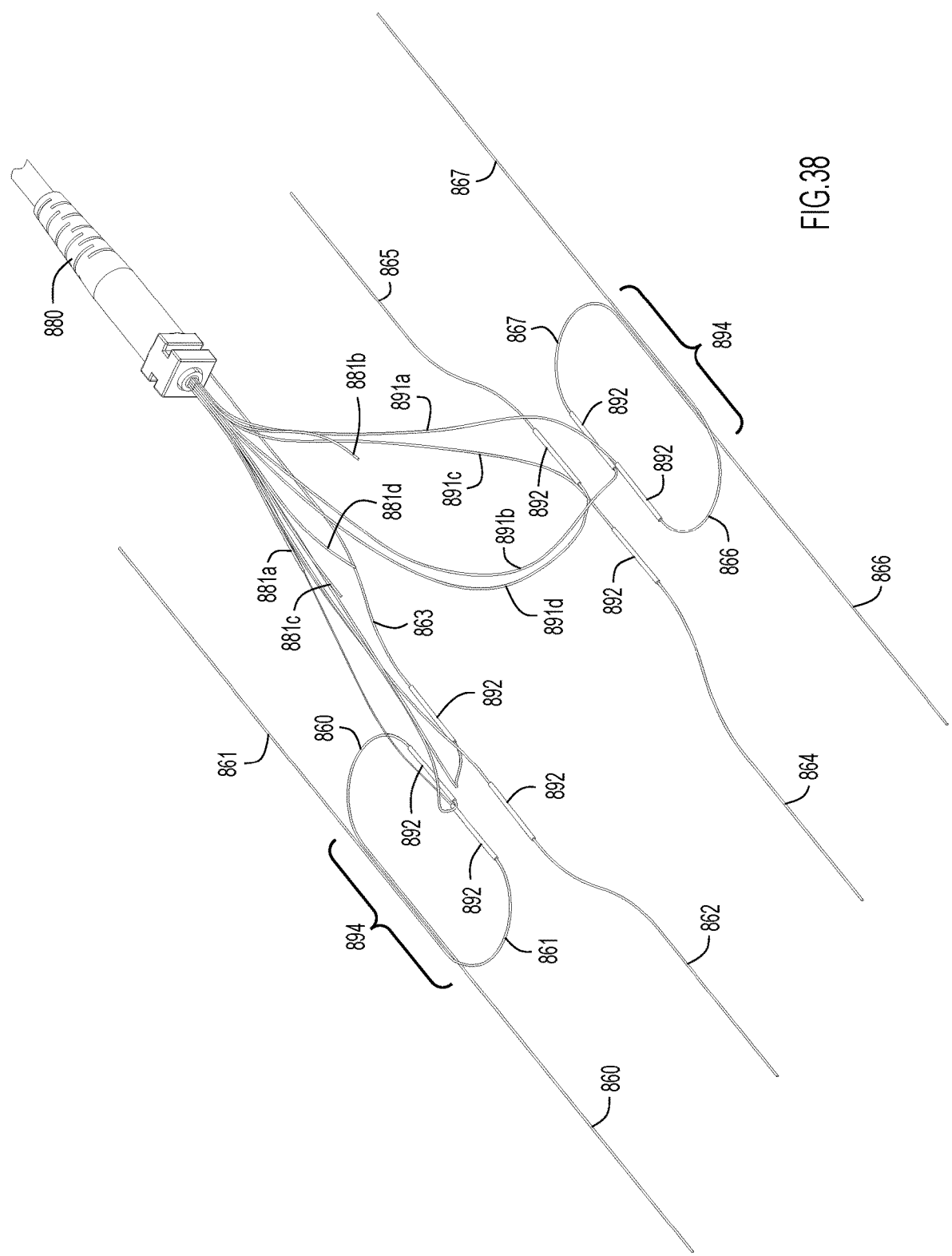
FIG. 38 illustrates an optical fiber layout of a light disinfecting pad according to one implementation.
Figure 39A:
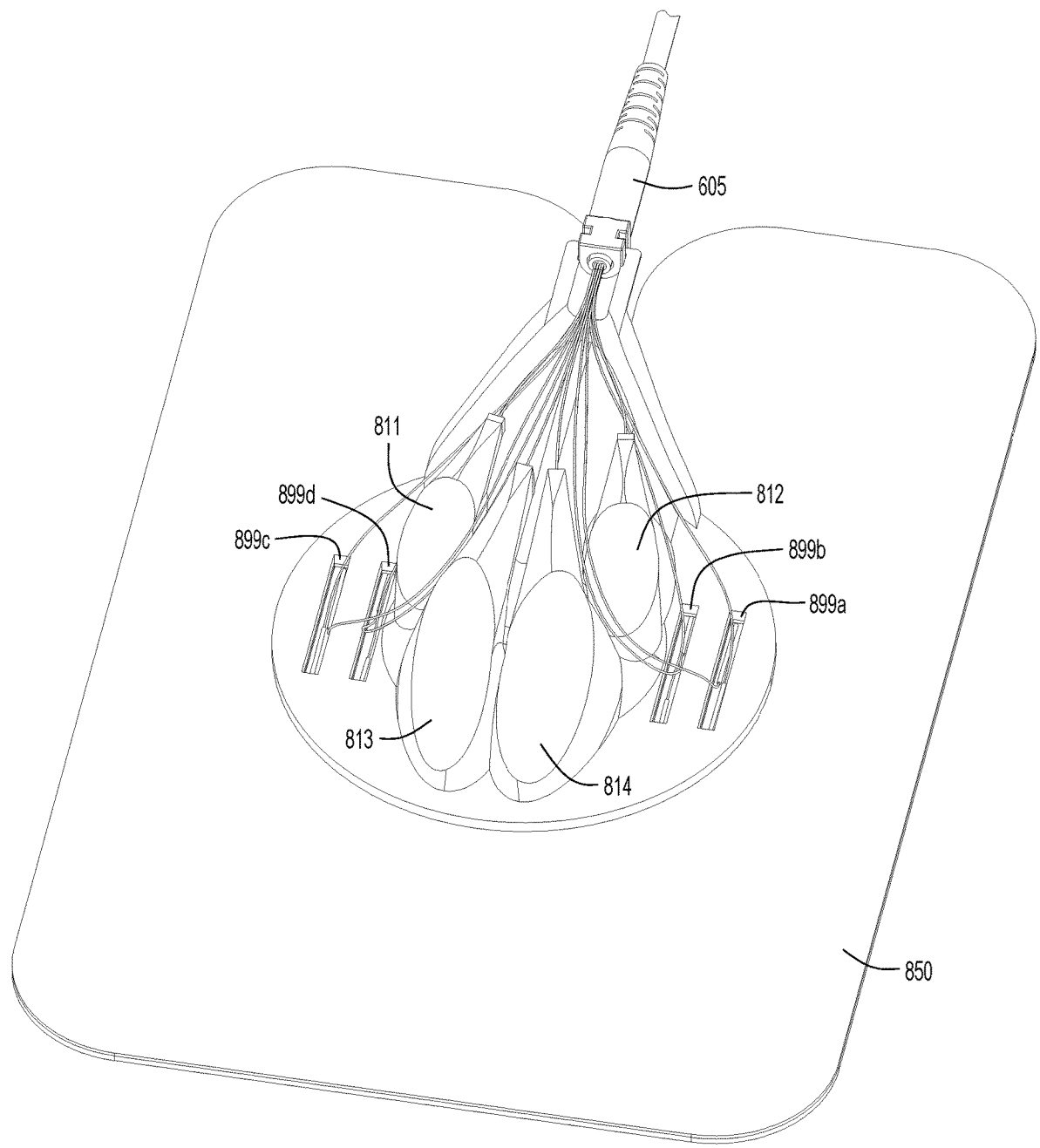
FIG. 39A shows a top perspective view of a light disinfecting system according to one implementation.
Figure 39B:
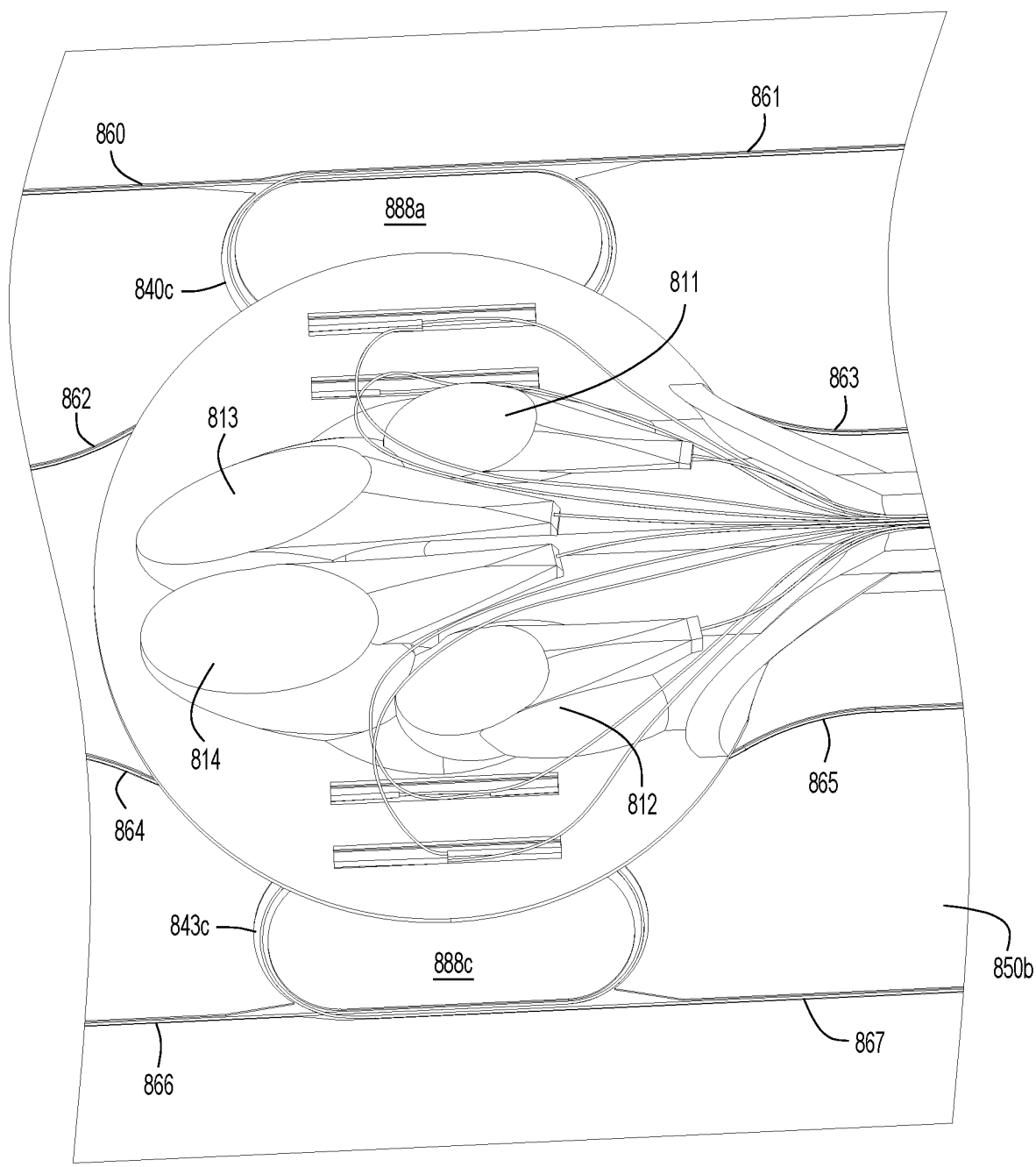
FIG. 39B is a top view of the light disinfecting system of FIG. 39A. with the upper element of the light disinfecting pad removed.

In the example implementation of FIGS. 34-40 the light disinfecting pad 850 includes a total of eight radially emitting fibers 860-867 that respectively lie in channels 840a, 840b, 841a, 841b, 842a, 842b, 843a and 843b of the lower element 850b. FIG. 38 illustrates a layout of the radially emitting fibers 860-867 inside the lower element 850b of the light disinfecting pad 850 with the lower element 850b removed.

As best seen in FIGS. 35C and 38, according to some implementations each of the eight radially emitting fibers 860-867 is optically coupled to a light source (not shown) via a respective eight transport fibers that each extends form a proximal optical connector 881 through a distal end of the optical fiber umbilical 880. The transport fibers represented by reference numerals 891a-d and 898a-d exit the distal end of the umbilical cord 880 and pass through a housing of the light disinfecting device 810 (formed in part by the cover 820). The transport fibers 891a and 891b pass through slotted opening 899a in the base 815 of the light disinfecting device 810 and through the slotted opening 897a of the upper element 850a of pad 850 and are respectively optically coupled to radially emitting fibers 866 and 867 via optical couplers 892. The transport fibers 891c and 891d pass through slotted opening 899b in the base 815 of the light disinfecting device 810 and through the slotted opening 897b of the upper element 850a of pad 850 and are respectively optically coupled to radially emitting fibers 864 and 865 via optical couplers 892. The transport fibers 898a and 899b pass through slotted opening 899c in the base 815 of the light disinfecting device 810 and through the slotted opening 897c of the upper element 850a of pad 850 and are respectively optically coupled to radially emitting fibers 860 and 861 via optical couplers 892. The transport fibers 891c and 891d pass through slotted opening 899d in the base 815 of the light disinfecting device 810 and through the slotted opening 897d of the upper element 850a of pad 850 and are respectively optically coupled to radially emitting fibers 862 and 863 via optical couplers 892.

Figure 36A:
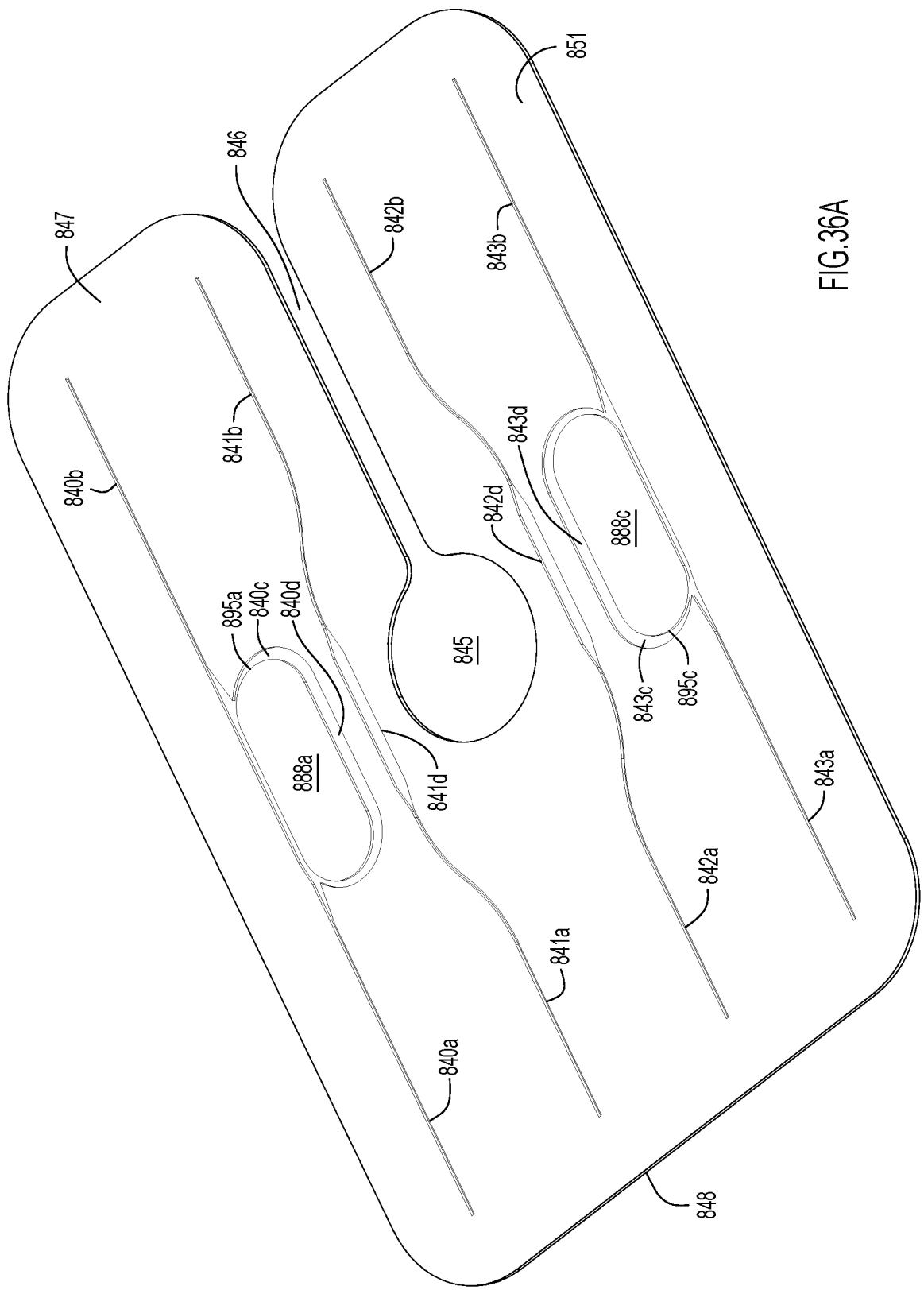
FIG. 36A is a top perspective view of a lower element of a disinfecting light pad according to one implementation.
Figure 36B:
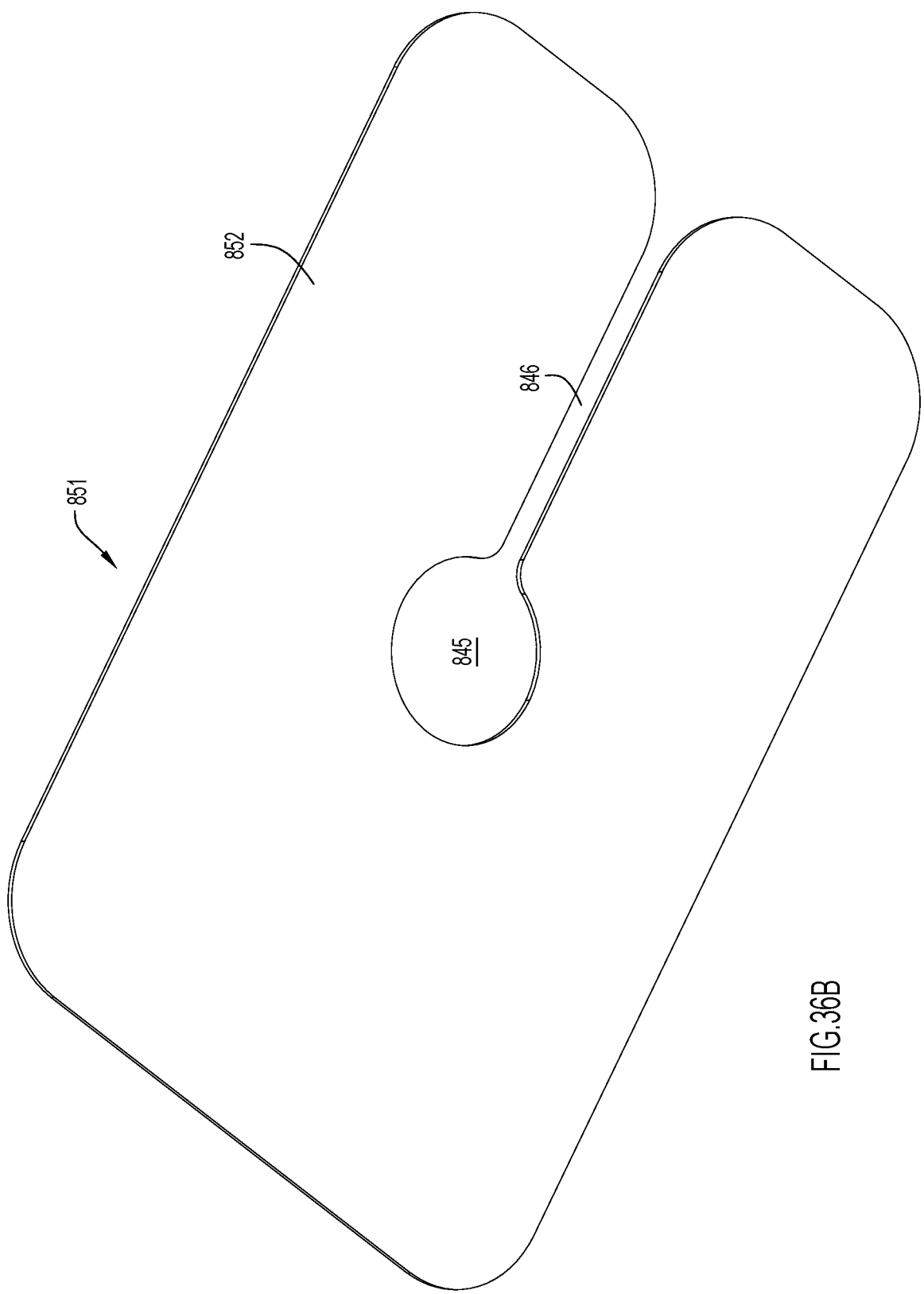
FIG. 36B is a bottom perspective view of the lower element of FIG. 36A.
Figure 37A:
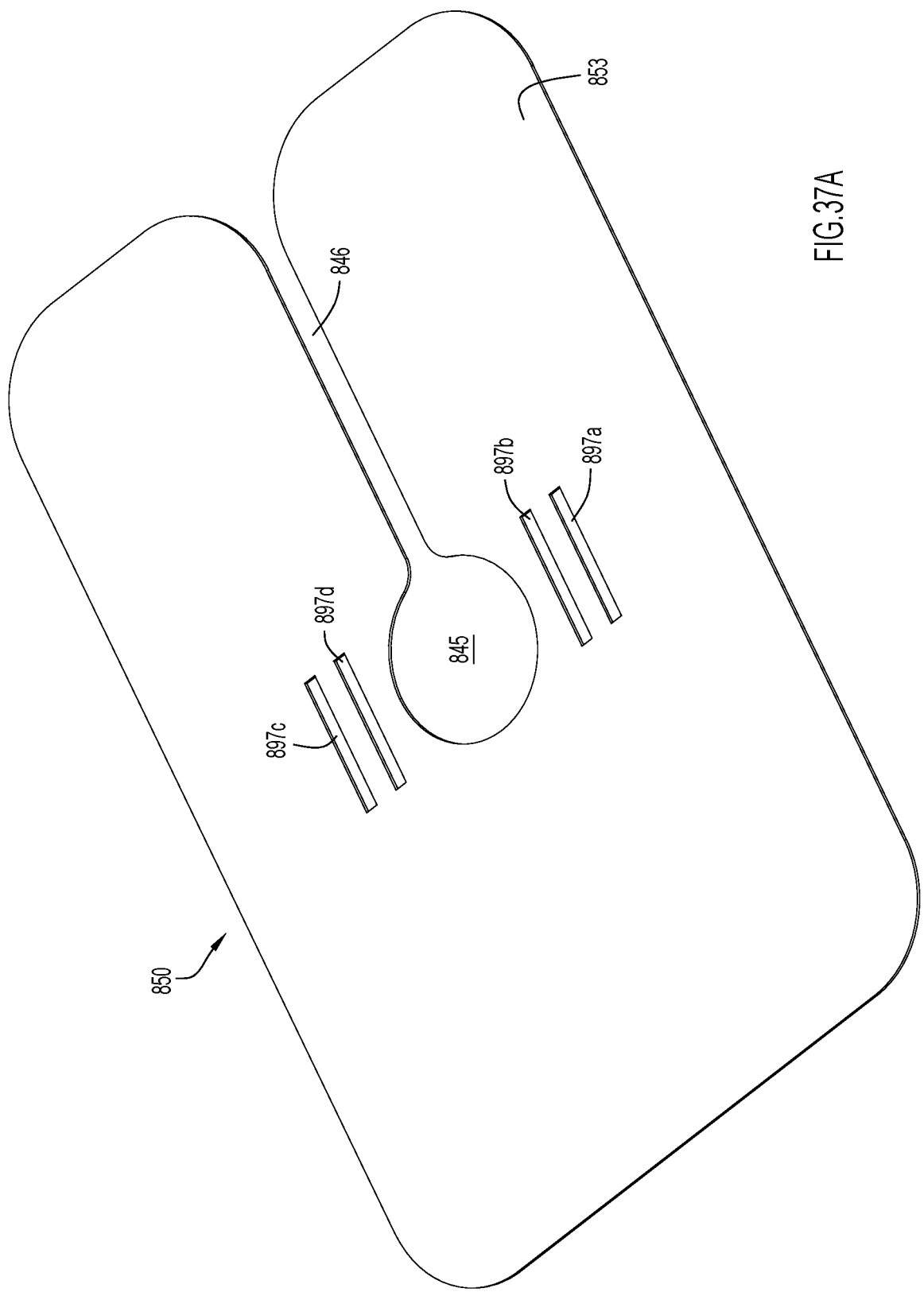
FIG. 37A is a top perspective view of an upper element of a disinfecting light pad according to one implementation.
Figure 37B:
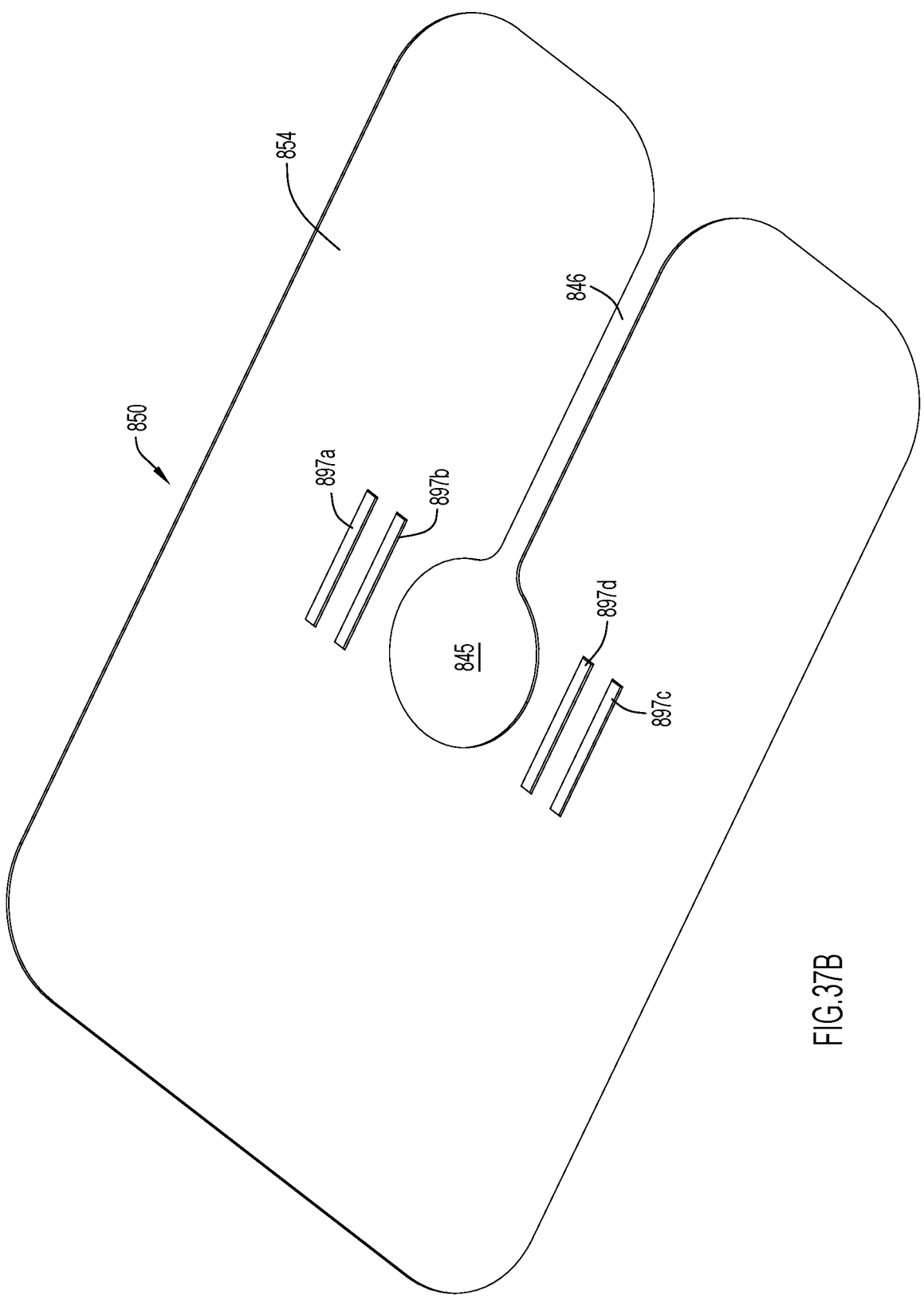
FIG. 37B is a bottom perspective view of the upper element of FIG. 37A.

According to some implementations each of the optical couplers 892 is housed in one of channels 840d, 841d, 842d and 843d. As best shown in FIG. 36A, the optical coupler channels 840d, 841d, 842d and 843d have a greater width and/or depth dimension of that of the radially emitting fiber channels 840a-b, 841a-b, 842a-b and 843a-b.

According to some implementations the distal end of each of the transport fibers is butt coupled to the proximal end of the radially emitting fibers inside the optical couplers 892. According to some implementations the optical couplers 892 comprise a capillary tubing of fused silica having a protective polyimide coating. According to some implementations the distal end of the transport fibers are coupled to the proximal end of the radial emitting fibers by an adhesive having an index of refraction between that of the core of the transport fibers and that of the core of the radially emitting fibers.

As shown best shown in FIGS. 35C and 38, according to some implementations the optical fibers 881a-d in which light is respectively transported into optical bodies 811-814 also extend through the umbilical 880 from the proximal optical connector 881. As explained above, according to some implementations the optical fibers 811a-d are end emitting optical fibers like, or similar in construction to a transport fiber. In the exemplary implementation of FIGS. 34-40, wherein disinfecting light is provided through the light disinfecting system 800 via twelve optical fibers, the umbilical cord proximal connector 881 has twelve ports that each receive and direct light from one or more light sources into a proximal end of a respective transport fiber and/or end emitting fiber 891a-d, 898a-d and 881a-d.

According to some implementations the upper and lower elements 850a and 850b of the light disinfecting pad 850 are each made of a material that enables the light disinfecting pad to flex so as to conform, or at least partially conform, to the surface on which it is applied.

As explained above, optical fibers typically comprise cylindrical glass or plastic cores through which light is transported. The core runs along the fiber's length and is surrounded by a medium with a lower index of refraction, typically a cladding of a different glass, or plastic. The core and cladding of an optical fiber are susceptible to breaking if excessively stressed. To address this issue, according to some implementations the channels in the light disinfecting pad 850 that house the radially emitting fibers are sized to have a width and/or depth that are larger than the outer diameter of the radially emitting optical fibers so that they are capable of sliding inside the channels when the light disinfecting pad is bent. This reduces or eliminates the occurrence of tensile stresses in the radial emitting optical fibers when the light disinfecting pad 850 is bent. To this end, according to some implementations the channels inside the light disinfecting pad 850 have a width and/or depth that is between about 5% to about 30% greater than the outer diameter of the radially emitting fibers.

According to some implementations, each of the optical couplers 892 is housed in one of channels 840d, 841d, 842d and 843d. As best shown in FIG. 36A, the optical coupler channels 840d, 841d, 842d and 843d have a greater width and/or depth dimension of that of the radially emitting fiber channels 840a-b, 841a-b, 842a-b and 843a-b.

As shown in FIGS. 36A, 38, 39B and 40, according to some implementations each of the proximal ends of radially emitting fibers 860, 861, 866 and 867 is disposed in one of tracks 840c or 843c. The tracks are respectively formed by an at least partially curved structure 888a and 888c that is each respectively defined by a perimeter wall 895a and 895c. According to some implementations, the optical couplers 892 associated with each of radially emitting fibers 860 and 861 are housed in the track formed by structure 888a and the optical couplers 892 associated with each of radially emitting fibers 866 and 867 are housed in the track formed by structure 888c. According to some implementations the portion of the track in which the optical couplers 892 reside is straight.

Figure 40:
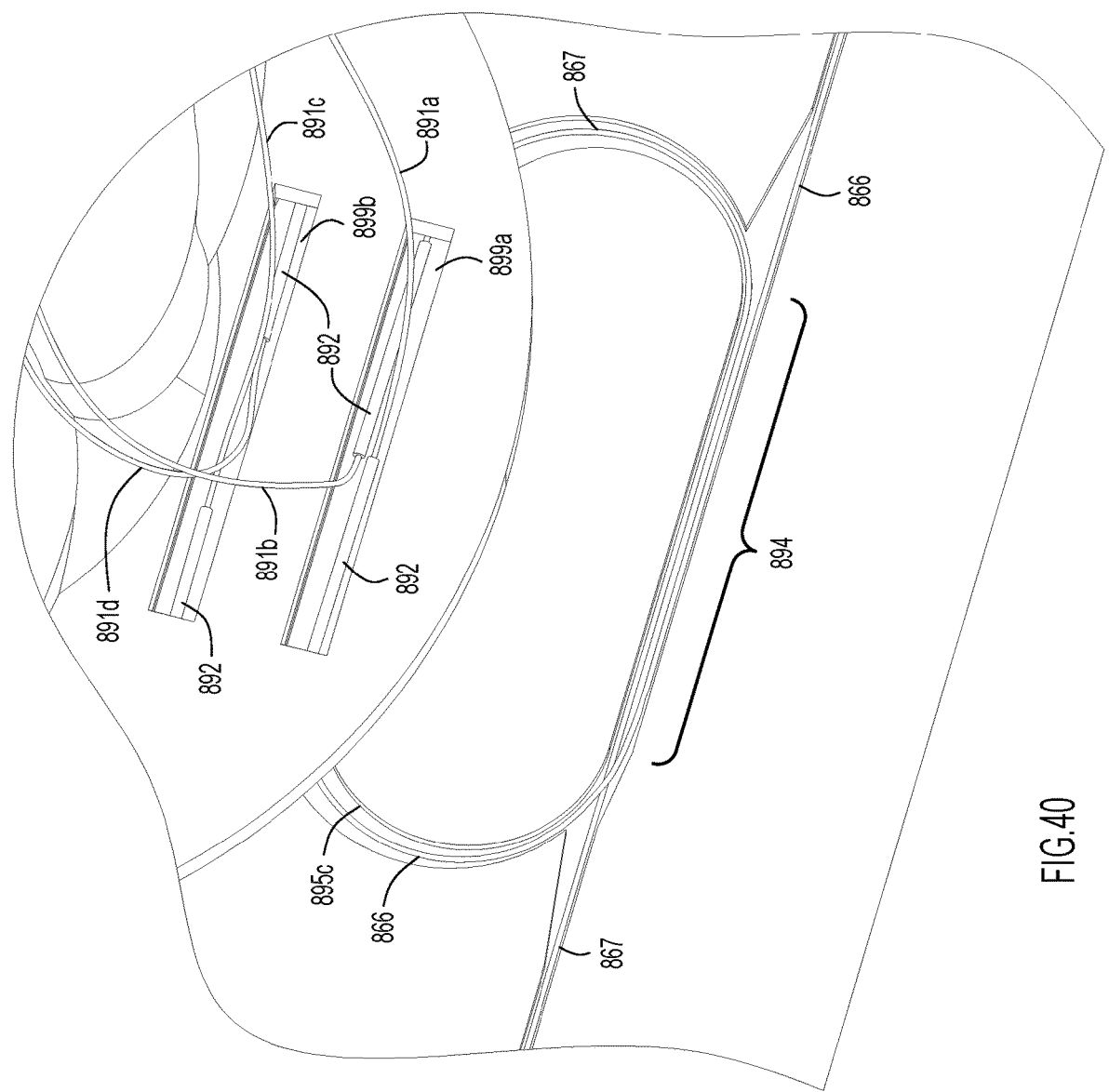
FIG. 40 is a top view of a light disinfecting assembly showing a routing of optical fibers inside a light disinfecting pad according to one implementation.

As shown in FIG. 40, each of radially emitting optical fiber 866 and 867 is routed in the track 843c so as not to be held taut inside the track when the light disinfecting pad 850 is positioned flat on a surface. In the implementation of FIG. 40 this provision of slack results in at least a portion of each of the radially emitting fibers 866 and 867 to be spaced away from the outer wall 895c of structure 888c when the light disinfecting pad 850 is laid flat on a surface. This provision of slack in the radially emitting optical fibers 866 and 867 inside the track 843c guards against excessive tensile forces being applied to the radially emitting optical fibers when the light disinfecting pad 850 is bent or pulled in tension as a result of the slack being taken up inside the track when the light disinfecting pad is bent. This is particularly important in implementations where at least a portion of the length of the radially emitting optical fiber is fixed inside a channel in which it is housed.

According to some implementations radially emitting fiber 886 follows a counter-clockwise path through the track 843c and radially emitting fiber 867 follows a clockwise path through the track 843c. According to some implementations one or both of the radially emitting fibers 866 and 867 change course inside the track by 180 degrees and overlap one another in at least a portion of the track 843c in the region labeled 894.

As seen in the accompanying figures, the layout of the radially emitting fibers 860 and 861 on the opposite side of the light disinfecting device 810 take a similar path through track 843a.

In the foregoing description the light disinfecting pad 850 is disclosed as being integrated with a light disinfecting device 810 of a light disinfecting system 800. It is appreciated, however, that the light disinfecting pad may comprise a standalone device apart from the light disinfecting systems disclosed above. According to such a standalone light disinfecting pad, light may be deliver to the radially emitting fibers disposed therein through the transport fibers via a dedicated optical fiber umbilical.

While specific implementations and applications have been illustrated and described, it is to be understood that the invention is not limited to the precise configuration and components disclosed herein. Various modifications, changes, and variations which will be apparent to those skilled in the art may be made in the arrangement, operation, and details of the methods and systems of the present invention disclosed herein without departing from the spirit and scope of the invention.

For example, the disclosure describes in detail various implementations of light disinfecting systems and of their individual components. It is appreciated, however, that the disclosed inventive features are applicable to a host of other types of devices inside and outside the medical field. As mentioned above, the apparatus and methods disclosed herein can also be applied to equipment or components of water processing plants, food processing plants, dairies, livestock habitation facilities, etc.

The following clauses disclose in an unlimited way additional implementations, with each clause representing an implementation. Additional implementations are represented by one or more of the implementations of one group or groups of clauses with one or more implementations of another group or groups of clauses. Group A through C clauses are provided.

Group A Clauses:

Clause 1. An assembly for bacterially disinfecting a designated target site, the assembly comprising:
   a first end emitting optical fiber having a terminal end configured to only end emit a first beam of bacterial disinfecting light from the terminal end;
   a first body including a plurality of optical surfaces that are configured to direct at least a portion of the first beam of bacterial disinfecting light to the target site, the plurality of optical surfaces including a first refractive optical surface, a second refractive optical surface and a first total reflective surface, the first total reflective optical surface being disposed between the first and second refractive optical surfaces in a designated optical pathway of the first beam of bacterial disinfecting light.

Clause 2. The assembly according to clause 1, wherein the first total reflective surface comprises a boundary between a first material having a first refractive index and a second material having a second refractive index less than the first refractive index, the second material being air.

Clause 3. The assembly according to clause 2, wherein the first material comprises a polymer.

Clause 4. The assembly according to clause 1, wherein the first total reflective surface comprises a light reflective metal.

Clause 5. The assembly according to clause 1, wherein the terminal end of the first end emitting optical fiber is located in a lumen or recess of the first body.

Clause 6. The assembly according to clause 5, wherein the first end emitting optical fiber comprises a core having an end, the assembly further comprising an index matching material disposed between the end of the core and the first refractive optical surface.

Clause 7. The assembly according to clause 6, wherein the index matching material is an adhesive that secures the first end emitting optical fiber to the first body.

Clause 8. The assembly according to clause 1, wherein the second refractive optical surface constitutes at least a portion of a bottom of the first body.

Clause 9. The assembly according to clause 8, wherein the second refractive optical surface is a concave surface.

Clause 10. The assembly according to clause 1, wherein the plurality of optical surfaces further comprises a second total reflective surface, the second total reflective surface being located between the first total reflective surface and the second refractive optical surface.

Clause 11. The assembly according to clause 10, wherein at least one of the first and second total reflective surfaces is a total internal reflection optical surface.

Clause 12. The assembly according to clause 10, wherein each of the first and second total reflective surfaces is a total internal reflection optical surface.

Clause 13. The assembly according to clause 11, wherein the terminal end of the first end emitting optical fiber is located at a first location in the first body and is configured to end emit the first beam of disinfecting light in a direction distal to the first location, the plurality of optical surfaces of the first body being arranged in or on the first body such that when the first beam of disinfecting light is emitted from the terminal end of the first end emitting optical fiber at least a portion of the first beam of bacterial disinfecting light is caused to exit the first body at a second location that is proximal to the first location.

Clause 14. The assembly according to clause 12, wherein the terminal end of the first end emitting fiber is located at a first location in the first body and is configured to end emit the first beam of disinfecting light in a direction distal to the first location, the plurality of optical surfaces of the first body being arranged in the first body such that when the first beam of disinfecting light is emitted from the terminal end of the first end emitting fiber at least a portion of the first beam of bacterial disinfecting light is caused to exit the first body at a second location that is proximal to the first location.

Clause 15. The assembly according to clause 1, wherein the first end emitting optical fiber comprises at an end thereof a power density lowering end cap.

Clause 16. The assembly according to clause 1, further comprising a first through opening located adjacent a side of the first body, the first through opening extending from a top surface of the assembly to a bottom surface of the assembly and being configured to accommodate the passage of a medical device.

Clause 17. The assembly according to clause 1, wherein the assembly further comprises a substrate, the substrate including one or more channels in which reside one or more radially emitting optical fibers that are configured to radially emit bacterial disinfecting light, the substrate being at least partially transparent to the bacterial disinfecting light, the first body being positioned above and physically coupled to the substrate.

Clause 18. The assembly according to clause 17, wherein the substrate is flexible and the one or more radially emitting optical fibers contain slack inside the one or more channels.

Clause 19. The assembly according to clause 18, wherein the substrate is flat.

Clause 20. The assembly according to clause 16, wherein the assembly further comprises a liquid absorbent pad that is at least partially transparent to the first beam of bacterial disinfecting light, the liquid absorbent pad being located beneath at least a portion of the first body and having a second through opening in communication with the first through opening.

Clause 21. The assembly according to clause 1, wherein the first end emitting optical fiber, first refractive surface and first reflective surface are configured such that when the first beam of bacterial disinfecting light is emitted from the terminal end of the first end emitting optical fiber a substantial portion of the first beam of bacterial disinfecting light is transported inside the first body from the first refractive optical surface to the first reflective surface.

Clause 22. The assembly according to clause 21, wherein the substantial portion is greater than or equal to 80%.

Clause 23. The assembly according to clause 21, wherein the first reflective surface and second refractive optical surface are arranged with respect to one another and configured such that a substantial portion of the first beam of bacterial disinfecting light received at the first reflective surface is reflected onto the second refractive optical surface through the first body.

Clause 24. The assembly according to clause 23, wherein the substantial portion is greater than or equal to 80%.

Clause 25. The assembly according to clause 23, wherein the first reflective surface is a total internal reflection optical surface.

Clause 26. The assembly according to clause 1 further comprising:

a second end emitting optical fiber having a terminal end configured to only end emit a second beam of bacterial disinfecting light from the terminal end;

a second body including a plurality of optical surfaces that are configured to direct at least a portion of the second beam of bacterial disinfecting light to the target site, the plurality of optical surfaces including a first refractive optical surface, a second refractive optical surface and a first total reflective surface, the first total reflective optical surface being disposed between the first and second refractive optical surfaces in a designated optical pathway of the second beam of bacterial disinfecting light.

Clause 27. The assembly according to clause 26, wherein the first body and second body comprise a unitary structure.

Clause 28. The assembly according to clause 27, wherein the unitary structure comprises a molded polymer.

Clause 29. The assembly according to clause 26, wherein the first reflective surface of each of the first and second body is a total internal reflection optical surface.

Clause 30. The assembly according to clause 26, wherein the first reflective surface of each of the first and second body comprises a light reflective metal.

Group B Clauses:

Clause 1. An assembly for bacterially disinfecting a designated target site, the assembly comprising:

a first end emitting optical fiber having a terminal end, the first end emitting optical fiber configured to end emit a first beam of bacterial disinfecting light from the terminal end;

a first body including a plurality of optical surfaces that are configured to direct at least a portion of the first beam of bacterial disinfecting light to the target site, the plurality of optical surfaces including a first refractive optical surface, a second refractive optical surface and a first total internal reflection optical surface, the first total internal reflection optical surface being disposed between the first and second refractive optical surfaces in a designated optical pathway of the first beam of bacterial disinfecting light.

Clause 2. The assembly according to clause 1, wherein the first total reflection optical surface comprises a boundary between a first material having a first refractive index and a second material having a second refractive index less than the first refractive index, the second material being air.

Clause 3. The assembly according to clause 2, wherein the first material comprises a polymer.

Clause 4. The assembly according to clause 1, wherein the terminal end of the first end emitting optical fiber is located in a lumen or recess of the first body.

Clause 5. The assembly according to clause 4, wherein the first end emitting optical fiber comprises a core having an end, the assembly further comprising an index matching material disposed between the end of the core and the first refractive optical surface.

Clause 6. The assembly according to clause 5, wherein the index matching material is an adhesive that secures the first end emitting optical fiber to the first body.

Clause 7. The assembly according to clause 1, wherein the second refractive optical surface constitutes at least a portion of a bottom of the first body.

Clause 8. The assembly according to clause 7, wherein the second refractive optical surface is a concave surface.

Clause 9. The assembly according to clause 1, wherein the plurality of optical surfaces further comprises a second total reflection optical surface, the second total reflection optical surface being located between the first total reflection optical surface and the second refractive optical surface.

Clause 10. The assembly according to clause 9, wherein the terminal end of the first end emitting optical fiber is located at a first location in the first body and is configured to end emit the first beam of disinfecting light in a direction distal to the first location, the plurality of optical surfaces of the first body being arranged in or on the first body such that when the first beam of disinfecting light is emitted from the terminal end of the first end emitting optical fiber at least a portion of the first beam of bacterial disinfecting light is caused to exit the first body at a second location that is proximal to the first location.

Clause 11. The assembly according to clause 1, wherein the first end emitting optical fiber comprises at an end thereof a power density lowering end cap.

Clause 12. The assembly according to clause 1, further comprising a first through opening located adjacent a side of the first body, the first through opening extending from a top surface of the assembly to a bottom surface of the assembly and being configured to accommodate the passage of a medical device.

Clause 13. The assembly according to clause 1, wherein the assembly further comprises a substrate, the substrate including one or more channels in which reside one or more radially emitting optical fibers that are configured to radially emit bacterial disinfecting light, the substrate being at least partially transparent to the bacterial disinfecting light, the first body being positioned above and physically coupled to the substrate.

Clause 14. The assembly according to clause 13, wherein the substrate is flexible and the one or more radially emitting optical fibers contain slack inside the one or more channels.

Clause 15. The assembly according to clause 14, wherein the substrate is flat.

Clause 16. The assembly according to clause 12, wherein the assembly further comprises a liquid absorbent pad that is at least partially transparent to the first beam of bacterial disinfecting light, the liquid absorbent pad being located beneath at least a portion of the first body and having a second through opening in communication with the first through opening.

Clause 17. The assembly according to clause 1, wherein the first end emitting optical fiber, first refractive surface and first total reflection optical surface are configured such that when the first beam of bacterial disinfecting light is emitted from the terminal end of the first end emitting optical fiber a substantial portion of the first beam of bacterial disinfecting light is transported inside the first body from the first refractive optical surface to the first total reflection optical surface.

Clause 18. The assembly according to clause 17, wherein the substantial portion is greater than or equal to 80%.

Clause 19. The assembly according to clause 17, wherein the first total reflection optical surface and second refractive optical surface are arranged with respect to one another and configured such that a substantial portion of the first beam of bacterial disinfecting light received at the first total reflection optical surface is reflected onto the second refractive optical surface through the first body.

Clause 20. The assembly according to clause 19, wherein the substantial portion is greater than or equal to 80%.

Clause 21. The assembly according to clause 1, further comprising:
    a second end emitting optical fiber having a terminal end, the second end emitting optical fiber configured to end emit a second beam of bacterial disinfecting light from the terminal end;
    a second body including a plurality of optical surfaces that are configured to direct at least a portion of the second beam of bacterial disinfecting light to the target site, the plurality of optical surfaces including a first refractive optical surface, a second refractive optical surface and a first total internal reflection optical surface, the first total internal reflection optical surface being disposed between the first and second refractive optical surfaces in a designated optical pathway of the second beam of bacterial disinfecting light.

Clause 22. The assembly according to clause 21, wherein the first body and second body comprise a unitary structure.

Clause 23. The assembly according to clause 22, wherein the unitary structure comprises a molded polymer.

Clause 24. The assembly according to clause 21, wherein the terminal end of the second end emitting optical fiber is located in a lumen or recess of the second body.

Clause 25. The assembly according to clause 24, wherein an index matching material is disposed between the terminal end of the second end emitting optical fiber and the first refractive optical surface of the second body.

Clause 26. The assembly according to clause 21, wherein the plurality of optical surfaces further comprises a second total reflection optical surface, the second total reflection optical surface being located between the first total reflection optical surface and the second refractive optical surface.

Clause 27. The assembly according to clause 26, wherein the terminal end of the second end emitting optical fiber is located at a first location in the first body and is configured to end emit the second beam of disinfecting light in a direction distal to the first location, the plurality of optical surfaces of the second body being arranged on or in the second body such that when the second beam of disinfecting light is emitted from the terminal end of the second end emitting optical fiber at least a portion of the second beam of bacterial disinfecting light is caused to exit the second body at a second location that is proximal to the first location.

Clause 28. The assembly according to clause 21, wherein the second end emitting optical fiber comprises at an end thereof a power density lowering end cap.

Group C Clauses:
    Clause 1. An assembly for bacterially disinfecting a designated target site, the assembly comprising:
    a first end emitting fiber having a terminal end configured to end emit a first beam of bacterial disinfecting light;

a second end emitting fiber having a terminal end configured to end emit a second beam of bacterial disinfecting light;

a first body including a plurality of optical surfaces that are configured to direct at least a portion of the first beam of bacterial disinfecting light to the target site, the plurality of optical surfaces including a first refractive optical surface, a second refractive optical surface and a first reflective surface, the first reflective surface being disposed between the first and second refractive optical surfaces in a designated optical pathway of the first beam of bacterial disinfecting light; and a second body including a plurality of optical surfaces that are configured to direct at least a portion of the second beam of bacterial disinfecting light to the target site, the plurality of optical surfaces including a first refractive optical surface, a second refractive optical surface and a first reflective surface, the first reflective surface being disposed between the first and second refractive optical surfaces in a designated optical pathway of the second beam of bacterial disinfecting light.

Clause 2. The assembly according to clause 1, wherein the first body and second body comprise a unitary structure.

Clause 3. The assembly according to clause 1, wherein each of the first and second bodies comprises a polymer.

Clause 4. The assembly according to clause 2, wherein the unitary structure comprises a molded polymer.

Clause 5. The assembly according to clause 1, wherein the first reflective surface of each of the first and second bodies is a total internal reflection optical surface.

Clause 6. The assembly according to clause 1, wherein the first reflective surface of each of the first and second bodies comprises a light reflective metal.

Clause 7. The assembly according to clause 1, wherein the terminal end of the first end emitting optical fiber is located in a lumen or recess of the first body and the terminal end of the second end emitting optical fiber is located in a lumen or recess of the second body.

Clause 8. The assembly according to clause 7, wherein an index matching material is disposed between the terminal end of the first end emitting optical fiber and the first refractive optical surface of the first body, and an index matching material is disposed between the terminal end of the second end emitting optical fiber and the first refractive optical surface of the second body.

Clause 9. The assembly according to clause 1, wherein the second refractive optical surface of the first body constitutes at least a portion of a bottom of the first body and the second refractive optical surface of the second body constitutes at least a portion of a bottom of the second body.

Clause 10. The assembly according to clause 9, wherein the second refractive surface of each of the first body and second body is a concave surface.

Clause 11. The assembly according to clause 1, wherein each of the plurality of optical surfaces of each of the first and second bodies further comprises a second reflective surface, the second reflective surface being located between the first reflective surface and the second refractive optical surface.

Clause 12. The assembly according to clause 11, wherein at least one of the first and second reflective surfaces of each of the first and second bodies is a total internal reflection surface.

Clause 13. The assembly according to clause 11, wherein each of the first and second reflective surfaces of each of the first and second bodies is a total internal reflection optical surface.

Clause 14. The assembly according to clause 13, wherein the terminal end of the first end emitting optical fiber is located at a first location in the first body and is configured to end emit the first beam of disinfecting light in a direction distal to the first location, the plurality of optical surfaces of the first body being arranged in or on the first body such that when the first beam of bacterial disinfecting light is emitted from the terminal end of the first end emitting optical fiber at least a portion of the light is caused to exit the first body at a second location proximal to the first location, and wherein the terminal end of the second end emitting optical fiber is located at a first location in the second body and is configured to end emit the second beam of bacterial disinfecting light in a direction distal to the first location, the plurality of optical surfaces of the second body being arranged in or on the second body such that when the second beam of disinfecting light is emitted from the terminal end of the second end emitting optical fiber at least a portion of the light is caused to exit the second body at a second location proximal to the first location.

Clause 15. The assembly according to clause 5, wherein the first total internal reflection optical surface of each of the first body and second body comprises a boundary between a first material having a first refractive index and a second material having a second refractive index less than the first refractive index, the second material being air.

Clause 16. The assembly according to clause 15, wherein the first material comprises a polymer.

Clause 17. The assembly according to clause 8, wherein the index matching material is an adhesive that secures the first end emitting optical fiber to the first body and the second end emitting optical fiber to the second body.

Clause 18. The assembly according to clause 1, wherein each of the first and second end emitting optical fibers comprises at an end thereof a power density lowering end cap.

Clause 19. The assembly according to clause 1, further comprising a first through opening located between a side of the first body and a side of the second body, the first through opening extending from a top surface of the assembly to a bottom surface of the assembly and being configured to accommodate the passage of a medical device.

Clause 20. The assembly according to clause 1, wherein the assembly further comprises a substrate, the substrate including one or more channels in which reside one or more radially emitting optical fibers that are configured to radially emit bacterial disinfecting light, the substrate being at least partially transparent to the bacterial disinfecting light, the first and second bodies being positioned above and physically coupled to the substrate.

Clause 21. The assembly according to clause 20, wherein the substrate is flexible and the one or more radially emitting optical fibers contain slack inside the one or more channels.

Clause 22. The assembly according to clause 21, wherein the substrate is flat.

Clause 23. The assembly according to clause 19, wherein the assembly further comprises a liquid absorbent pad that is at least partially transparent to the first and second beams of bacterial disinfecting light, the liquid absorbent pad being located beneath at least a portion of the first and second bodies and having a second through opening in communication with the first through opening.

Clause 24. The assembly according to clause 1, wherein the first end emitting optical fiber, first refractive optical surface and first reflective surface of the first body are configured such that when the first beam of bacterial disinfecting light is emitted from the terminal end of the first end emitting optical fiber a substantial portion of the first beam of bacterial disinfecting light is transported inside the first body from the first refractive optical surface to the first reflective surface.

Clause 25. The assembly according to clause 24, wherein the substantial portion is greater than or equal to 80%.

Clause 26. The assembly according to clause 24, wherein the first reflective surface and second refractive optical surface are arranged with respect to one another and configured such that a substantial portion of the first beam of bacterial disinfecting light received at the first reflective surface is reflected onto the second refractive optical surface through the first body.

Clause 27. The assembly according to clause 26, wherein the substantial portion is greater than or equal to 80%.

Clause 28. The assembly according to clause 24, wherein the second end emitting optical fiber, first refractive optical surface and first reflective surface of the second body are configured such that when the first beam of bacterial disinfecting light is emitted from the terminal end of the second end emitting optical fiber a substantial portion of the second beam of bacterial disinfecting light is transported inside the first body from the first refractive optical surface to the first reflective surface.

Clause 29. The assembly according to clause 28, wherein the substantial portion is greater than or equal to 80%.

Clause 30. The assembly according to clause 28, wherein the first reflective surface and second refractive optical surface are arranged with respect to one another and configured such that a substantial portion of the second beam of bacterial disinfecting light received at the first reflective surface is reflected onto the second refractive optical surface through the second body.

What is claimed is:

1. An assembly for bacterially disinfecting a designated target site, the assembly comprising:
    a first end emitting optical fiber having a terminal end configured to only end emit a first beam of bacterial disinfecting light from the terminal end;
    a first body including a plurality of optical surfaces that are configured to direct at least a portion of the first beam of bacterial disinfecting light to the target site, the plurality of optical surfaces including a first refractive optical surface, a second refractive optical surface and a first total reflective surface, the first total reflective optical surface being disposed between the first and second refractive optical surfaces in a designated optical pathway of the first beam of bacterial disinfecting light; and
    a substrate, the substrate including one or more channels in which reside one or more radially emitting optical fibers that are configured to radially emit bacterial disinfecting light, the substrate being at least partially transparent to the bacterial disinfecting light, the first body being positioned above and physically coupled to the substrate.

2. The assembly according to claim 1, wherein the substrate is flexible.

3. The assembly according to claim 2, wherein the one or more radially emitting optical fibers contain slack inside the one or more channels.

4. The assembly according to claim 1, wherein the substrate is flat.

5. The assembly according to claim 1, wherein the first total reflective surface comprises a boundary between a first material having a first refractive index and a second material having a second refractive index less than the first refractive index, the second material being air.

6. The assembly according to claim 5, wherein the first material comprises a polymer.

7. The assembly according to claim 1, wherein the terminal end of the first end emitting optical fiber is located in a lumen or recess of the first body.

8. The assembly according to claim 7, wherein the first end emitting optical fiber comprises a core having an end, the assembly further comprising an index matching material disposed between the end of the core and the first refractive optical surface, the index matching material being an adhesive that secures the first end emitting optical fiber to the first body.

9. The assembly according to claim 1, wherein the second refractive optical surface constitutes at least a portion of a bottom of the first body.

10. The assembly according to claim 9, wherein the second refractive optical surface is a concave surface.

11. The assembly according to claim 1, wherein the first total reflective surface is a total internal reflection optical surface.

12. The assembly according to claim 1, further comprising a first throughs opening located in a side of the first body, the first through opening extending from a top surface of the first body to a bottom surface of the first body and being configured to accommodate the passage of a medical device.

13. The assembly according to claim 1, wherein the one or more radially emitting optical fibers is/are located to a side of the first body.

14. The assembly according to claim 12, wherein at least a portion of the substrate is located beneath the first body, the at least portion of the substrate including a through opening in communication with the first through opening of the first body, the through opening of the substrate being configured to accommodate the passage of the medical device.

15. The assembly according to claim 1 further comprising:
    a second end emitting optical fiber having a terminal end configured to only end emit a second beam of bacterial disinfecting light from the terminal end; and
    a second body including a plurality of optical surfaces that are configured to direct at least a portion of the second beam of bacterial disinfecting light to the target site, the plurality of optical surfaces including a first refractive optical surface, a second refractive optical surface and a first total reflective surface, the first total reflective optical surface being disposed between the first and second refractive optical surfaces in a designated optical pathway of the second beam of bacterial disinfecting light.

16. The assembly according to claim 15, wherein the second body is positioned above and physically coupled to the substrate.

17. The assembly according to claim 15, wherein the first body and second body comprise a unitary structure.

18. The assembly according to claim 16, wherein the first body and second body comprise a unitary structure, the first and second bodies being unmovable with respect to one another.

19. The assembly according to claim 17, wherein the unitary structure comprises a molded polymer.

20. The assembly according to claim 15, wherein the first reflective surface of each of the first and second body is a total internal reflection optical surface.

* * * * *